United States Patent [19]
Lau et al.

[11] Patent Number: 5,639,780
[45] Date of Patent: Jun. 17, 1997

[54] N-BENZYL INDOL-3-YL BUTANOIC ACID DERIVATIVES AS CYCLOOXYGENASE INHIBITORS

[75] Inventors: Cheuk Kun Lau, Ile Bizard; Cameron Black, Pointe Claire; Daniel Guay, Ile Perrot; Jacques-Yves Gauthier, Laval; Yves LeBlanc, Kirkland; Patrick Roy, Dollard des Ormeaux; Yves Ducharme, Montreal; Pierre Hamel, Laval, all of Canada

[73] Assignee: Merck Frosst Canada, Inc., Kirkland, Canada

[21] Appl. No.: 445,838

[22] Filed: May 22, 1995

[51] Int. Cl.⁶ .................. A61K 31/405; A61K 31/44; A61K 31/395; C07D 209/18; C07D 401/12; C07D 209/04

[52] U.S. Cl. .................. 514/419; 514/339; 546/256; 546/277.4; 546/273; 548/495

[58] Field of Search .................. 548/495; 546/273; 514/339, 419

[56] References Cited

U.S. PATENT DOCUMENTS

| | | | |
|---|---|---|---|
| 3,161,654 | 12/1964 | Shen | 260/319 |
| 3,196,162 | 7/1965 | Sarett et al. | 260/319 |
| 3,242,163 | 3/1966 | Sarett et al. | 260/211 |
| 3,654,349 | 4/1972 | Shen et al. | 260/515 M |
| 3,725,548 | 4/1973 | Shen et al. | 424/303 |

FOREIGN PATENT DOCUMENTS

| | | |
|---|---|---|
| 709843 | 5/1965 | Canada. |
| 709844 | 5/1965 | Canada. |
| 957990 | 5/1964 | United Kingdom. |
| 2225012 | 5/1990 | United Kingdom. |
| WO94/06769 | 3/1994 | WIPO. |

OTHER PUBLICATIONS

Chem. Abstracts, vol. 61, p. 4320 (a) (1964) "Resolution of Substituted Indoles" 1-p-chlorobenzyl-2-methyl-5-methoxy-3-indolyl)propionic acid.

*Primary Examiner*—David B. Springer
*Attorney, Agent, or Firm*—Curtis C. Panzer; David L. Rose

[57] ABSTRACT

The invention encompasses the novel compound of Formula I useful in the treatment of cyclooxygenase-2 mediated diseases.

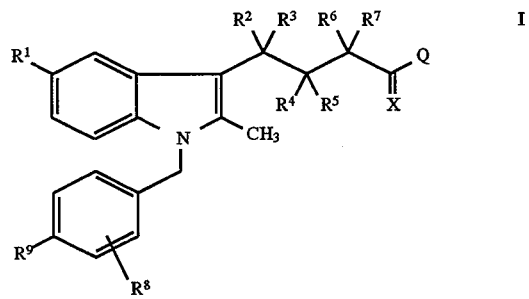

The invention also encompasses certain pharmaceutical compositions for treatment of cyclooxygenase-2 mediated diseases comprising compounds of Formula I.

13 Claims, No Drawings

N-BENZYL INDOL-3-YL BUTANOIC ACID DERIVATIVES AS CYCLOOXYGENASE INHIBITORS

BACKGROUND OF THE INVENTION

This invention relates to methods of treating cyclooxygenase mediated diseases and certain pharmaceutical compositions therefor.

Non-steroidal, anti-inflammatory drugs exert most of their anti-inflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 or the constitutive enzyme, as originally identified in bovine seminal vesicles. More recently the gene for a second inducible form of cyclooxygenase (cyclooxygenase-2) has been cloned, sequenced and characterized initially from chicken, murine and human sources. This enzyme is distinct from the cyclooxygenase-1 which has been cloned, sequenced and characterized from various sources including the sheep, the mouse and man. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar anti-inflammatory, antipyretic and analgesic properties to a conventional non-steroidal anti-inflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

Such a compound would also be of use in the treatment of Alzheimers disease and to inhibit bone resorption (for use in the treatment of osteoporosis).

A brief description of the potential utility of cyclooxygenase-2 is given in an article by John Vane, Nature, Vol. 367, pp. 215–216, 1994.

SUMMARY OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I.

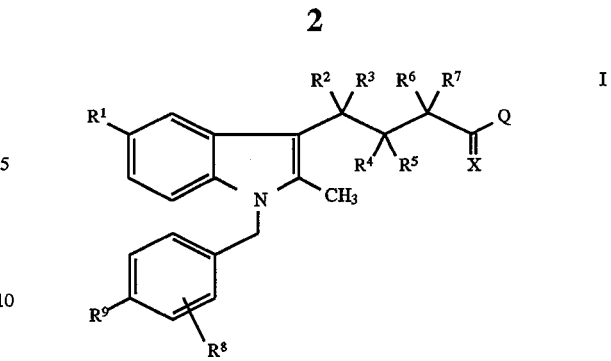

The invention also encompasses certain pharmaceutical compositions for treatment of cyclooxygenase-2 mediated diseases comprising compounds of Formula I.

DETAILED DESCRIPTION OF THE INVENTION

In one embodiment the invention encompasses the novel compound of Formula I as well as a method of treating cyclooxygenase-2 mediated diseases comprising administration to a patient in need of such treatment of a non-toxic therapeutically effective amount of a compound of Formula I.

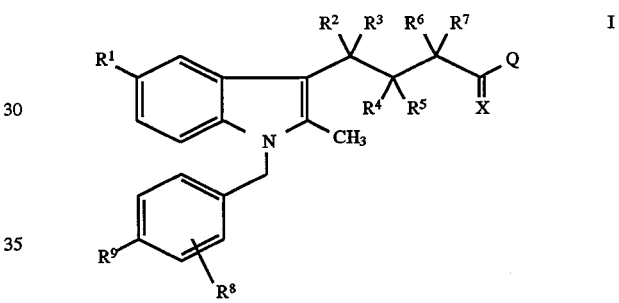

or a pharmaceutically acceptable salt thereof, wherein:

Q is
  (a) —OR or
  (b) —$NR^{11}R^{12}$;

X is
  (a) —O or
  (b) —S;

R is
  (a) —H or
  (b) —$C_{1-4}$ alkyl or momo, di or tri-substituted —$C_{1-4}$ alkyl, where the substituent is selected from F, Cl, Br and I;

$R^1$ is
  (a) —$OCH_3$ or $OCH_2CH_3$,
  (b) —$OCH_2F$,
  (c) —$OCHF_2$,
  (d) —$OCF_3$,
  (e) —$CF_3$,
  (f) —F, Cl, Br or I,
  (g) methyl or ethyl;

$R^2$, $R^3$, $R^4$, $R^5$, $R^6$ and $R^7$ are each independently
  (a) —H,
  (b) —F or Cl,
  (c) —$C_{1-5}$ alkyl or haloalkyl,
  (d) —$C_{3-6}$ cycloalkyl,
  (e) —$CF_3$, $CF_2H$ or $CFH_2$,
  (f) —OH, $OR^{10}$, $SR^{10}$, $S(O)R^{10}$ or $S(O)_2R^{10}$,
  (g) nonsubstituted, mono- or di-substituted benzyl, wherein the substituent is selected from (1) $CF_3$,
(2) $CN$,
(3) F, Cl, Br or I,
(4) $C_{1-6}$ alkyl,
(5) $OR^{10}$, $SR^{10}$, $S(O)R^{10}$ or $S(O)_2R^{10}$,
(h) phenyl or mono- or di-substituted phenyl, wherein the substituent is selected from
(1) CF3,
(2) $CN$,
(3) F, Cl, Br, I,
(4) $C_{1-6}$ alkyl,
(5) $OR^{10}$, $SR^{10}$, $S(O)R^{10}$ or $S(O)_2R^{10}$,
or $R^2$ together with $R^3$ form an oxo group;
or $R^4$ together with $R^5$ form an oxo group;
or $R^6$ together with $R^7$ form an oxo group;
or $R^2$ and $R^3$ are joined so that together with the carbon atom to which they are attached there is formed a saturated monocyclic ting of 3, 4, 5, 6 or 7 members, optionally one hetero atom which is oxygen;
or $R^3$ and $R^4$ are joined so that together with the carbon atoms to which they are attached there is formed a saturated or aromatic monocyclic ring of 3, 4, 5, 6 or 7 members;
or $R^3$ and $R^6$ are joined so that together with the carbon atoms to which they are attached there is formed a saturated or aromatic monocyclic ring of 3, 4, 5, 6 or 7 members;
or $R^4$ and $R^5$ are joined so that together with the carbon atom to which they are attached there is formed a saturated monocyclic ting of 3, 4, 5, 6 or 7 members, optionally containing one hetero atom which is oxygen;
or $R^4$ and $R^6$ are joined so that together with the carbon atoms to which they are attached there is formed a saturated or aromatic monocyclic ring of 3, 4, 5, 6 or 7 members;
or $R^6$ and $R^7$ are joined so that together with the carbon atom to which they are attached there is formed a saturated monocyclic ring of 3, 4, 5, 6 or 7 members, optionally containing an oxygen atom;

$R^8$ is
(a) hydrogen or
(b) F, Cl or Br, $R^9$ is
(a) Br, Cl or I,
(b) SMe, S(O)Me, SEt, $SCF_2H$ or $SCF_3$;

$R^{10}$ is methyl, ethyl or, benzyl optionally mono- or di-substituted,
wherein the substituent is selected from
(1) $CF_3$,
(2) $CN$,
(3) F, Cl, Br, I, and
(4) $C_{1-6}$ alkyl;

$R^{11}$ and $R^{12}$ are each independently
(a) —H,
(b) —$C_{1-4}$ alkyl,
(c) —$C_{3-6}$ cycloalkyl,
(d) —OR,
(e) —$C(O)R^{13}$,
(f) —$S(O)_2R^{14}$,
(g) mono-substituted $C_{2-4}$ alkyl wherein the substituent is selected from
(1) hydroxy,
(2) amino,
(3) methylamino, and
(4) dimethylamino,
(h) phenyl, benzyl or pyridyl optionally mono- or di-substituted, the substituents being selected from the group consisting of
(1) $CF_3$,
(2) $CN$,
(3) F, Cl, Br or I,
(4) $C_{1-6}$ alkyl;

or $R^{11}$ and $R^{12}$ are joined so that together with the nitrogen atom to which they are attached there is formed a saturated or unsaturated monocyclic ring of 3, 4, 5, 6, or 7 members, optionally containing one or two additional heteroatoms, said heteroatoms independently selected from N, O and S, wherein a carbon atom may optionally substituted with an oxo group and a sulfur atom of the ring may optionally substituted with two oxo groups;

$R^{13}$ is
(a) —H,
(b) —$C_{1-4}$ alkyl,
(c) —$CF_3$,
(d) phenyl or benzyl optionally mono- or di-substituted, the substituents being selected from the group consisting of
(1) $CF_3$,
(2) $CN$,
(3) F, Cl, Br or I,
(4) $C_{1-6}$ alkyl;

$R^{14}$ is
(a) —$C_{1-4}$ alkyl,
(b) —$CF_3$,
(c) phenyl or benzyl optionally mono- or di-substituted, the substituents being selected from the group consisting of
(1) $CF_3$,
(2) $CN$,
(3) F, Cl, Br or I,
(4) $C_{1-6}$ alkyl.

Within the definition of Q, some representative radicals are:

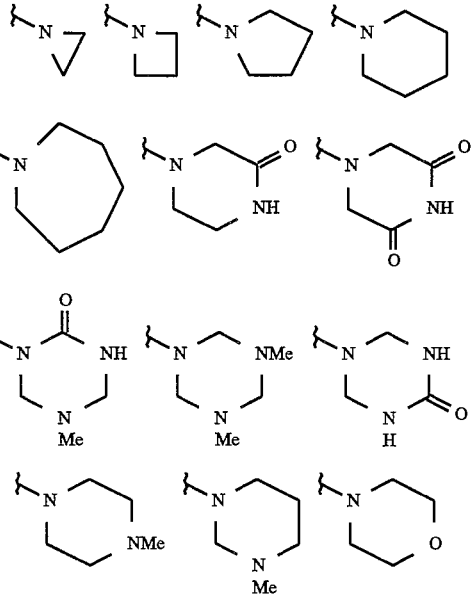

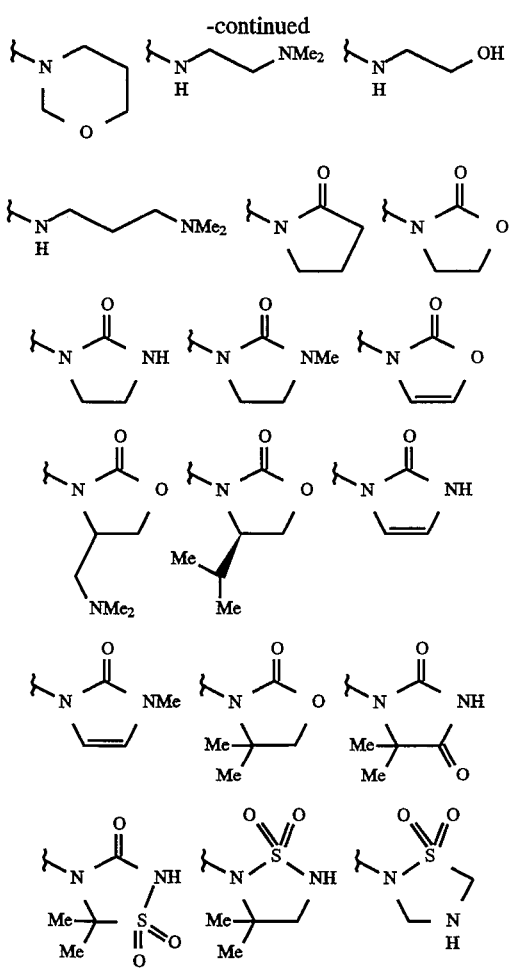

Within this embodiment there is a genus of compounds of formula I wherein

Q is
(a) —OR or
(b) —NR$^{11}$R$^{12}$;

X is
(a) —O or
(b) —S;

R is
(a) —H or
(b) —C$_{1-4}$ alkyl;

R$^1$ is
(a) —OCH$_3$,
(b) —OCF$_3$,
(c) —CF$_3$,
(d) Cl or Br,
(e) methyl;

R$^2$, R$^3$, R$^4$, R$^5$, R$^6$ and R$^7$ are independently
(a) —H,
(b) —F or Cl,
(c) —C$_{1-3}$ alkyl or haloalkyl,
(d) —C$_{3-6}$ cycloalkyl,
(e) —CF$_3$,
(f) —OH,
(g) nonsubstituted, mono- or di-substituted benzyl, wherein the substituent is selected from
(1) F, Cl, Br or I,
(2) C$_{1-3}$ alkyl or R$^2$ together with R$^3$ form an oxo group;

or R$^2$ and R$^3$ are joined so that together with the carbon atom to which they are attached there is formed a saturated monocyclic ring of 3, 4, 5, 6 or 7 members;

or R$^3$ and R$^4$ are joined so that together with the carbon atoms to which they are attached there is formed a saturated or aromatic monocyclic ring of 3, 4, 5, 6 or 7 members;

or R$^3$ and R$^6$ are joined so that together with the carbon atoms to which they are attached there is formed a saturated or aromatic monocyclic ring of 3, 4, 5, 6 or 7 members;

or R$^4$ and R$^5$ are joined so that together with the carbon atom to which they are attached there is formed a saturated monocyclic ring of 3, 4, 5, 6 or 7 members;

or R$^4$ and R$^6$ are joined so that together with the carbon atoms to which they are attached there is formed a saturated or aromatic monocyclic ring of 3, 4, 5, 6 or 7 members;

or R$^6$ and R$^7$ are joined so that together with the carbon atom to which they are attached there is formed a saturated monocyclic ring of 3, 4, 5, 6 or 7 members;

R$^8$ is
(a) hydrogen or
(b) F or Cl;

R$^9$ is
(a) Br, Cl or I,
(b) SMe, S(O)Me, SEt;

R$^{11}$ and R$^{12}$ are independently
(a) —H,
(b) —C$_{1-4}$ alkyl,
(c) —OR,
(d) —S(O)$_2$R$^{14}$,
(e) mono-substituted C$_{2-4}$ alkyl wherein the substituent is selected from
(1) hydroxy,
(2) amino,
(3) methylamino, and
(4) dimethylamino,
(f) phenyl, benzyl or pyridyl optionally mono- or di-substituted, the substituents being selected from the group consisting of
(1) CF$_3$,
(2) F, Cl, Br, or
(3) C$_{1-3}$ alkyl;

or R$^{11}$ and R$^{12}$ are joined so that together with the nitrogen atom to which they are attached there is formed a saturated or unsaturated monocyclic ring of 3, 4, 5, 6, or 7 members, optionally containing one or two additional heteroatoms, said heteroatoms independently selected from N, O and S, said ring optionally containing one or two carbonyl or sulfonyl groups;

R$^{14}$ is
(a) —C$_{1-4}$ alkyl,
(b) —CF$_3$,
(c) phenyl optionally mono- or di-substituted, the substituents being selected from the group consisting of
(1) CF$_3$,
(2) F, Cl, Br or I,
(3) C$_{1-3}$ alkyl;

Within the definition of Q, some representative radicals are:

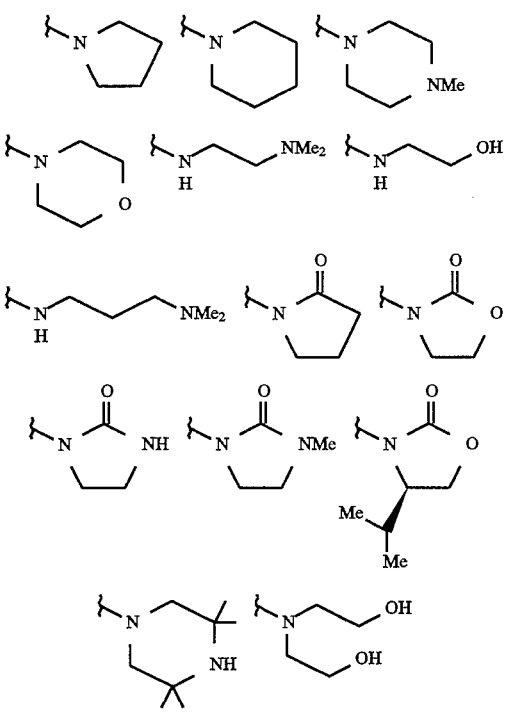

Within this genus is a class of compounds wherein
Q is
(a) —OR or
(b) —NR$^{11}$R$^{12}$;
X is
(a) —O or
(b) —S;
R is
(a) —H or
(b) methyl;
R$^1$ is
(a) —OCH$_3$,
(b) —OCF$_3$,
(c) Cl or Br,
(d) methyl;
R$^2$, R$^3$, R$^4$, R$^5$, R$^6$ and R$^7$ are independently
(a) —H,
(b) —F,
(c) —C$_{1-3}$ alkyl or substituted —C$_{1-3}$ alkyl wherein the substituent is F or Cl,
(d) —CF$_3$,
(e) —OH,
or R$^2$ together with R$^3$ form an oxo group;
or R$^2$ and R$^3$ are joined so that together with the carbon atom to which they are attached there is formed a saturated monocyclic ring of 4, 5 or 6 members;
or R$^3$ and R$^4$ are joined so that together with the carbon atoms to which they are attached there is formed a saturated or aromatic monocyclic ring of 4, 5 or 6 members;
or R$^3$ and R$^6$ are joined so that together with the carbon atoms to which they are attached there is formed a saturated or aromatic monocyclic ring of 4, 5 or 6 members;
or R$^4$ and R$^5$ are joined so that together with the carbon atom to which they are attached there is formed a saturated monocyclic ring of 4, 5 or 6 members;

R$^8$ is hydrogen;
R$^9$ is
(a) Br, Cl or I,
(b) SMe, S(O)Me;
R$^{11}$ and R$^{12}$ are independently
(a) —H,
(b) -methyl,
(c) —OR,
(d) —S(O)$_2$CH$_3$,
(e) mono-substituted C$_{2-4}$ alkyl wherein the substituent is selected from
(1) hydroxy, and
(2) amino,
(f) phenyl, benzyl or pyridyl optionally mono- or di-substituted, the substituents being selected from the group consisting of
(1) CF$_3$,
(2) F, Cl, Br, or
(3) C$_{1-3}$ alkyl;
or R$^{11}$ and R$^{12}$ are joined so that together with the nitrogen atom to which they are attached there is formed a saturated or unsaturated monocyclic ting of 4, 5 or 6 members, optionally containing one or two additional heteroatoms, said heteroatoms independently selected from N, O and S, wherein a carbon atom may optionally substituted with an oxo group and a sulfur atom of the ting may optionally substituted with two oxo groups;
R$^{14}$ is
(a) methyl,
(b) —CF$_3$,
(c) phenyl optionally mono- or di-substituted, the substituents being selected from the group consisting of
(1) CF$_3$,
(2) F, Cl or Br,
(3) methyl.
Within this class is a sub-class of compounds wherein
Q is
(a) —OR or
(b) —NR$^{11}$R$^{12}$;
X is
(a) —O or
—S;
R is
(a) —H or
(b) methyl;
R$^1$ is
(a) —OCH$_3$,
(b) —OCF$_3$,
(c) Cl or Br,
(d) methyl;
R$^2$, R$^3$, R$^4$, R$^5$, R$^6$ and R$^7$ are independently
(a) —H,
(b) —F,
(c) —C$_{1-3}$ alkyl or substituted —C$_{1-3}$ alkyl wherein the substituent is F or Cl,
(d) —CF$_3$,
(e) —OH,
or R$^2$ together with R$^3$ form an oxo group;
R$^8$ is hydrogen;
R$^9$ is
(a) Br, Cl or I,
(b) SMe, S(O)Me;
R$^{11}$ and R$^{12}$ are independently
(a) —H, (b) -methyl,
(c) —OR,
(d) —S(O)$_2$CH$_3$,
(e) mono-substituted C$_{2-4}$ alkyl wherein the substituent is selected from
  (1) hydroxy, and
  (2) amino,
(f) phenyl, benzyl or pyridyl optionally mono- or di-substituted, the substituents being selected from the group consisting of
  (1) CF$_3$,
  (2) F, Cl, Br, or
  (3) C$_{1-3}$ alkyl;

R$^{14}$ is
(a) methyl,
(b) —CF$_3$,
(c) phenyl optionally mono- or di-substituted, the substituents being selected from the group consisting of
  (1) CF$_3$,
  (2) F, Cl or Br,
  (3) methyl.

Illustrating the invention are the compounds of Examples 1 through 136.

The following are illustrative of the group

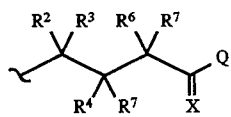

R$^2$ and R$^3$ are joined

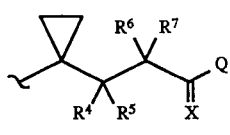
Example 1

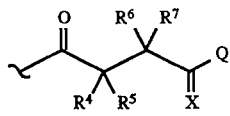
Example 16

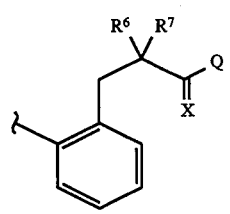
Example 20

R$^3$ and R$^6$ are joined

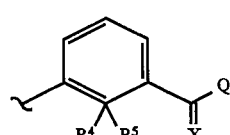
Example 22

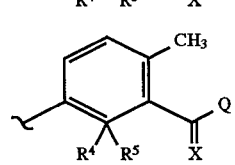
Example 64

R$^2$ and R$^3$ are together =O, and R$^5$ and R$^6$ are joined

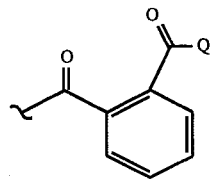
Example 63

R$^4$ and R$^5$ are joined

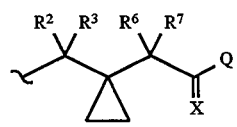
Example 31

R$^3$ and R$^4$ are joined

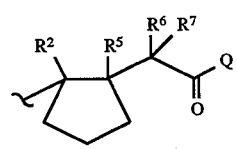
Example 81

Optical Isomers—Diastereomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof. Moreover, as appreciated by those of skill in the art, the generic graphical presentation of of such paired variables as R$^2$ and R$^3$, R$^4$ and R$^5$, R$^6$ and R$^7$, R$^8$ and R$^9$ are not intended to a represent a particular orientation of the paired members (eg R$^2$ and R$^3$). Thus, situations such as that wherein R$^3$ and R$^4$ are jioned together, or R$^3$ and R$^6$ are joined together. are equivalent to that wherein or wherein R$^2$ and R$^4$ are joined together. or R$^2$ and R$^6$, are joined together, respectively.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutically acceptable salts.

The Compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compound I may also be of use in the treatment and/or prevention of cyclooxygenase-mediated proliferative disorders such as may occur in diabetic retinopathy and tumour angiogenesis.

Compound I will also inhibit prostanoid-induced smooth muscle contraction by preventing the synthesis of contractile prostanoids and hence may be of use in the treatment of dysmenorrhea, premature labor, asthma and eosinophil related disorders. It will also be of use in the treatment of Alzheimer's disease and for decreasing bone loss in postmenopausal women (that is, treatment of osteoporosis).

By virtue of its high cyclooxygenase-2 (COX-2) activity and/or its specificity for cyclooxygenase-2 over cyclooxygenase-1 (COX-1), compound I will prove useful as an alternative to conventional non-steroidal anti-inflammatory drugs (NSAID'S) particularly where such non-steroidal anti-inflammatory drags may be contraindicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, compound I will be useful as a partial or complete substitute for conventional NSAID'S in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the compound of Formula I as defined above and one or more ingredients such as another pain reliever including acetominophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levodesoxyephedrine; an antiitussive including codeine, hydrocodone, caramiphen, carbetapentane, or dextramethorphan; a diuretic; a sedating or non-sedating antihistamine. In addition the invention encompasses a method of treating cyclooxygenase mediated diseases comprising: administration to a patient in need of such treatment a non-toxic therapeutically effect amount of the compound of Formula I, optionally co-administered with one or more of such ingredients as listed immediately above.
Pharmaceutical Compositions For the treatment of any of these cyclooxygenase mediated diseases compound I may be administered orally, topically, parenterally, by inhalation spray or rectally in dosage unit formulations containing conventional non-toxic pharmaceutically acceptable carders, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. No. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example, peanut oil, liquid paraffin, or olive oil.

Aqueous suspensions contain the active material in admixture with excipients suitable for the manufacture of aqueous suspensions. Such excipients are suspending agents, for example, sodium carboxymethyl-cellulose, methylcellulose, hydroxypropylmethycellulose, sodium alginate, polyvinyl-pyrrolidone, gum tragacanth and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of an oil-in-water emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carder material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drag combination and the severity of the particular disease undergoing therapy.

Methods of Synthesis

The compounds of the present invention can be prepared according to the following methods:

Method A

An aryl hydrazine II and a methyl ketone III are coupled via a Fischer indole synthesis in acetic acid at 60° C. to 100° C. or alternatively in 4M HCl in dioxane at 60° C. or alternatively in ethanolic HCl at reflux. The indole IV thus obtained may be benzylated by first deprotonating with KHMDS in THF/HMPA at −78° C. to 0° C. or alternatively with sodium hydride in DMF at room temperature, followed by treatment with a benzyl halide V to provide N-benzylated indole Ib. In the case of R═H in compound IV, the benzylation may be accomplished by treatment of IV in THF/HMPA at −780C with two equivalents of n-BuLi followed by addition of benzyl halide V, to directly afford examples of compound Ia. In the case of a benzylated indole VI without a-substituents (a special case of Ib in which $R^4=R^5=H$), an a-substituent may be introduced by enolization with LDA at −78° C. to 0° C. followed by treatment with an alkyl halide to provide VII. A second substituent may be similarly introduced to compound VII by sequential treatment with LDA and an alkyl halide to provide Ib. Compounds Ib and VII are examples of the present invention. Alkaline hydrolysis of esters Ib or VII provide examples of compound Ia of the present invention. Alternatively, hydrazine II may be benzylated by treatment with benzyl bromide V in the presence of a base such as potassium carbonate in DMF to provide N-benzyl hydrazine VIII. This hydrazine may be isolated as its free base or as its hydrochloride salt. This hydrazine may be reacted with ketone III via a Fischer indole synthesis as described above providing Ib directly.

Method B

An aryl hydrazine II may be coupled with a different methyl ketone such as IX via a Fischer indole synthesis as described in method A to produce indole X. This compound can be benzylated as described also in method A to give compound XI. This ester may then be reduced by treatment with reagents such as DIBAH to give indole aldehyde XII ($R^4=H$). Alternatively, ester XI may be transformed into an indole ketone ($R^4$=alkyl, aryl) by treatment first with the magnesium salt of N-methoxy-N-methylamine followed by an alkyl or aryl grignard reagent ($R^4MgX$). Compound XII may be reacted with a stabilized Wittig reagent XIII in refluxing toluene to provide compound XIV. For certain $R^2$, $R^3$ and $R^4$ groups, a higher temperature (>140° C.) may be required for this reaction to proceed. Some cases may even require the use of a more reactive olefination reagent such as in the Peterson reaction (e.g. TMSCHR$^6$COOR+LDA). Treatment of XIV with a lithium dialkyl cuprate in the presence of TMSCl provides the alkylated product XV which is an example of compound Ib of this invention. Hydrolysis of ester XV provides examples of acid Ia of the present invention. Ester XV may also be modified as in method A to give acid Ia.

Method C

The indole-unsaturated ester XIV may be treated with 50 psi H$_2$ in the presence of Pd/C or PtO$_2$ to provide compound XVI. Alternatively, this transformation may be accomplished by reacting ester XIV with magnesium turnings in methanol. Ester XVI may be transformed as in method A into acid XVII. Ester XVI and acid XVII are both examples of Ib and Ia of the present invention.

Method D

The indole-unsaturated ester XIV may be reacted with diazomethane in the presence of palladium acetate to provide compound XVIII which upon hydrolysis gives compound XIX. Both ester XVIII and acid XIX are representative examples of Ib and Ia.

Method E

Indole acetaldehyde XII ($R^4$=H) may be homolgated into cis-unsaturated ester XXI by treatment with a mixture of phosphonate XX, a base such as KHMDS and 18-crown-6 in THF at −78° C. As described in method D, this Z-olefinic ester may be converted into (cis) cyclopropane compound XXII which is an example of Ia of the present invention.

Method F

Indole XII may be reacted with an enolate obtained by treatment of ester XXIII with LDA at −78° C. to provide the aldol adduct XXIV. The hydroxyl group of this aldol adduct may be alkylated by treatment with electrophilic agents such as Me$_3$OBF$_4$ and a substituted benzyl trichloroacetamidate XXV to give the methyl ether XXVI($R^{10}$=Me) and the benzyl ether XXVI ($R^{10}$=benzyl) respectively. Subsequent alkaline hydrolysis of ester XXVI produces the acid XXVIII. In addition, direct hydrolysis of the aldol adduct XXIV gives the acid XXVII. Both compounds XXVII and XXVIII are examples of Ia.

Method G

It will be obvious to one skilled in the art that asymmetrically substituted compounds Ia may be synthesized as pure enantiomers or may be resolved into their pure enantiomers. For example, racemic Ia may be treated with KHMDS followed by pivaloyl chloride to form a mixed anhydride. The lithium salt of a chiral oxazolidinone may then be added to form a diastereotopic mixture of chiral imides XXIX and XXX, which are examples of compound I (where X=O) of the present invention. These two compounds may then be separated by chromatography or crystalization to provide the pure diastereomers. In the case of chiral imides XXIX and XXX without a-substitutents ($R^6$=$R^7$=H), it will be obvious again to one skilled in the art that an a-substituent may be introduced by enolization with a base such as LDA or KHMDS at −78° C. followed by treatment with an alkyl halide to provide XXIX and XXX (where $R^6$ or $R^7$=alkyl). Each pure diastereomer may then be hydrolyzed independently with lithium hydroperoxide to generate the pure enantiomers XXXI and XXXII which are examples of compound Ia of the present invention.

Method H

The cyclopropyl alcohol XXXIII (Eur. Pat. 604,114, Example 1, Step 7,) may be oxidized under the conditions of Swern to aldehyde XXXIV. Treatment of this aldehyde with Ph$_3$P=CHOMe, followed by hydrolysis of the resulting vinyl methyl ether will provide aldehyde XXXV. Addition of methyl magnesium bromide to this compound followed by Swern oxidation of the resulting alcohol will produce methyl ketone XXXVI. This ketone may be reacted with hydrazine VIII to provide indole XXXVII by first treating with acetic acid in toluene followed by heating the resulting hydrazone at 60° C. in 4M HCl/dioxane. The nitrile functionality of indole XXXVII may be converted to the methyl ester XXXVIII by treating with methanolic HCl. Introduction of a-substituents may be accomplished as described in method A to give compound XXXIX. This ester may be homolgated into nitrile XL according to the following sequence: treatment of XXXIX with DIBAH will produce an alcohol that may be converted to a bromide with Br$_2$/PPh$_3$ or to a mesylate with MsCl/Et$_3$N, both of which may be displaced with cyanide compound with give nitrile XL. Treatment of this compound with methanolic HCl will provide ester XLI. Possible introduction of a-substituents and hydrolysis may be accomplished according to method A to give acid XLII which is an example of compound Ia of the present invention.

Method I

Cyclopropyl aldehyde XXXIV when treated with Ph$_3$P=CHCOCH$_3$ will give methyl vinyl ketone XLIII. Hydrogenation of this olefin with H$_2$ and Pd/C as catalyst will provide ketone XLIV. This compound may be reacted with hydrazine VIII as described in methods A and H to give indole XLV. Conversion of the nitrile functionality of XLV into an ester, introduction of a-substituents, and hydrolysis may all be accomplished according to method H to give acid XLVI. Compound XLVI is an example of Ia of the present invention.

Method J

Phenyl acetonitrile XLVII can be treated with trimethylaluminium to produce benzyl methyl ketone XLVIII. This compound may be reacted with hydrazine II as described in method A to give indole XLIX. Metal halogen exchange using n-BuLi will produce a dianion that may be quenched with carbon dioxide followed by diazomethane treatment to give idole-benzoate ester L. N-benzylation of this compound and subsequent hydrolysis may be accomplished according to method A to give acid LI which is an example of Ia of the present invention.

Method K

A substituted indole LII may be acylated in the 3-position to give compound LIV by preforming its magnesium salt with EtMgBr and allowing it to react with an appropriate acid chloride LIII in the presence of a Lewis acid such as zinc chloride or aluminium chloride. This 3-acyl indole LIV can be N-benzylated and converted to the acid LV by the procedures described in method A. Compound LV is an example of Ia of the present invention.

Method L

An indolebutanoic acid of the type Ia may be treated with 1,1¢???-carbonyldiimidazole or with diethyl cyanophosphonate to form an active ester, or with oxalyl chloride to form an acid chloride. Subsequent treatment with an amine, acetamide, or sulfonamide of structure HNR$^{11}$R$^{12}$ and DMAP provides the desired amide, imide or acylsulfonamide which are examples of compound Ic of the present invention. Alternatively, the coupling may be performed by reacting the lithium salt LiNR$^{11}$R$^{12}$ with the mixed anhydride described in method G, thus providing examples of compound Ic of the present invention.

Method M

An indole ester of the type 1b may be treated with a thiation reagent such as Lawesson's reagent (LVI) in a solvent such as toluene or dioxane with or without reflux to produce the corresponding thionoester 1d (Q=OR). Similarly, an indole-amide of the type 1c will give the corresponding thioamide 1d (Q=NR$^{11}$R$^{12}$) when subjected to the same reaction conditions.
METHOD A
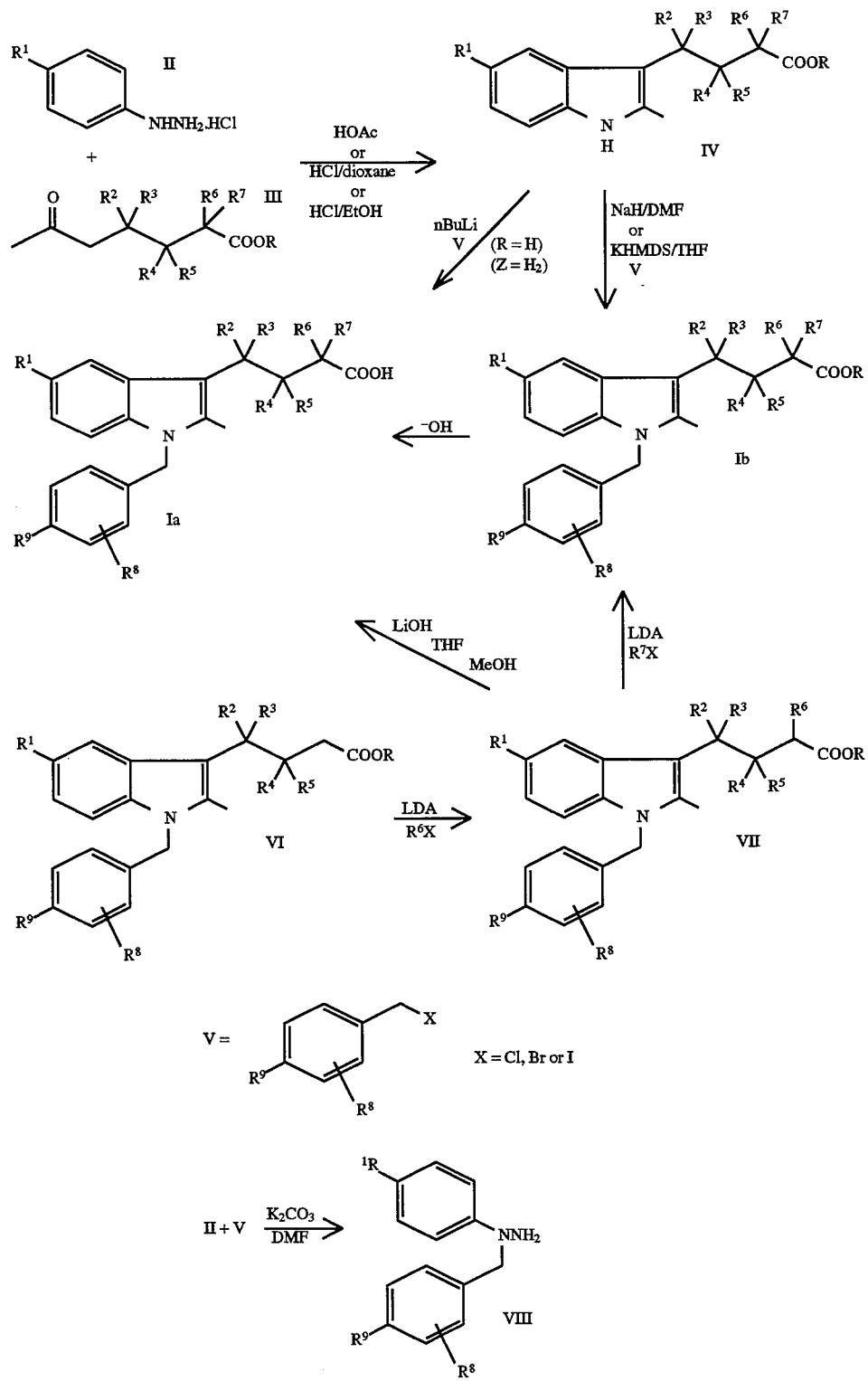

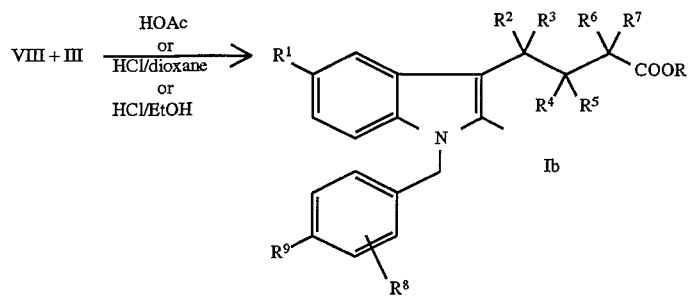
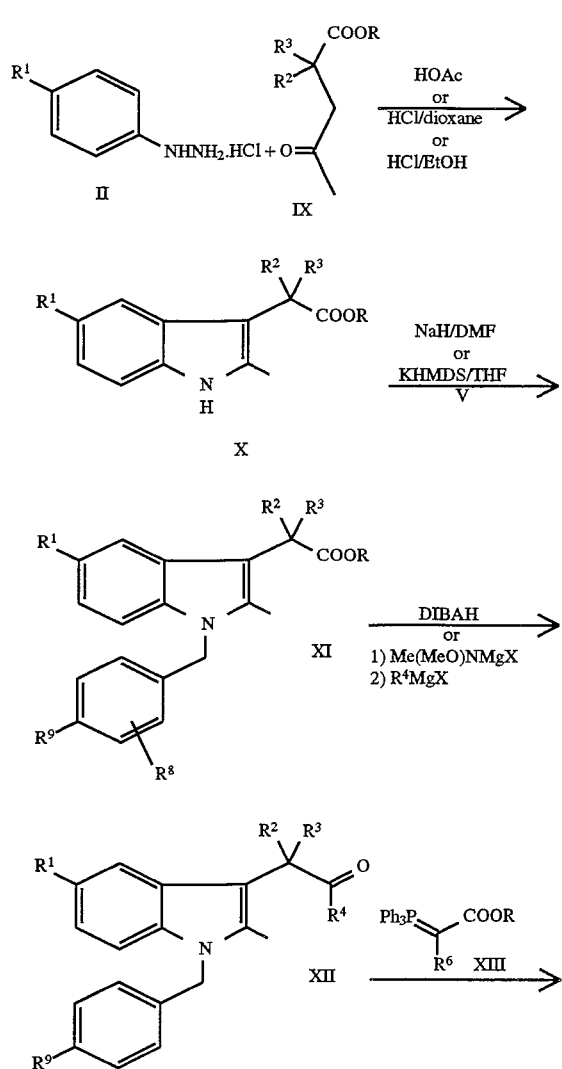
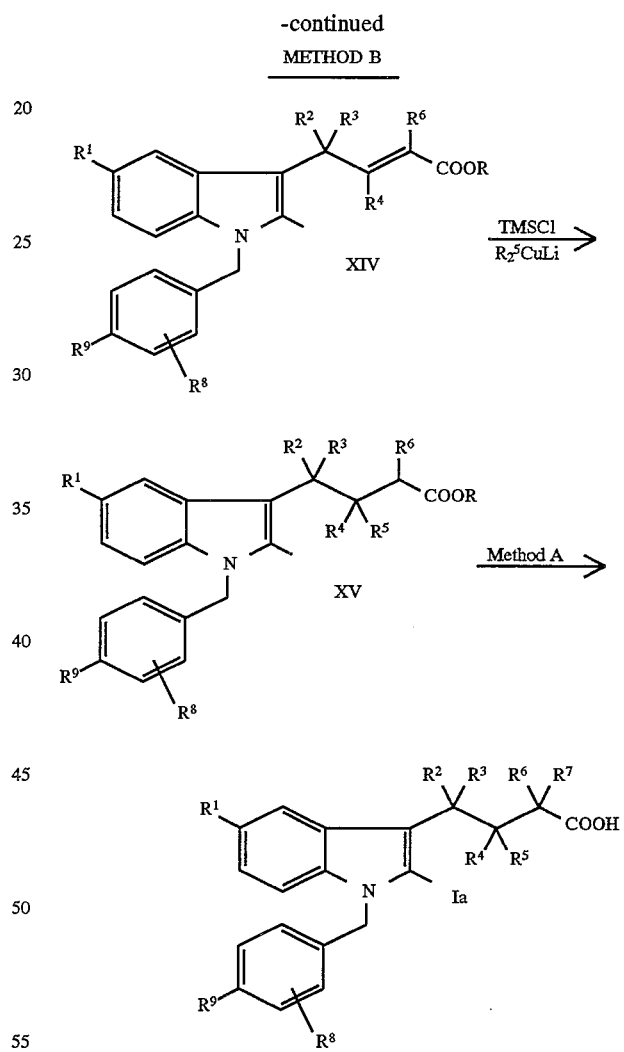

METHOD C
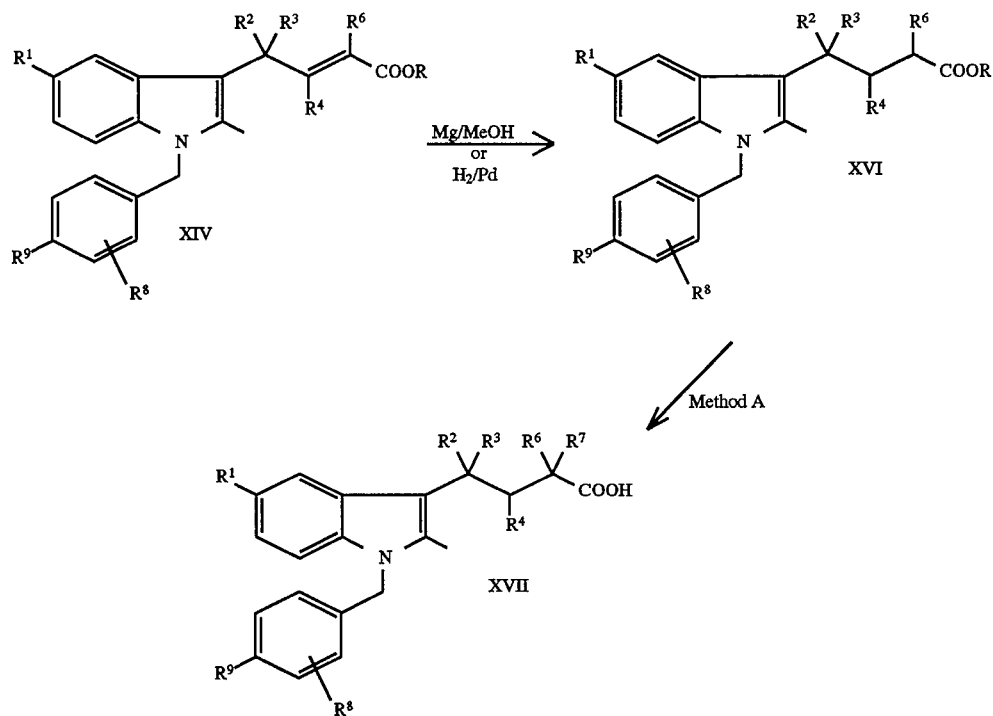
METHOD D
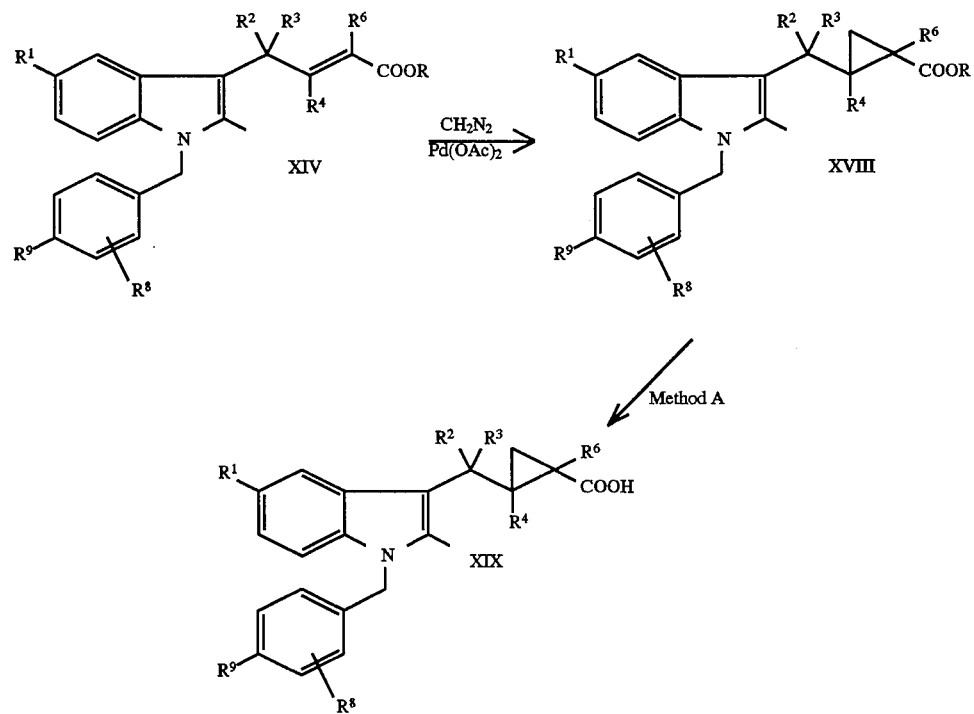

METHOD E
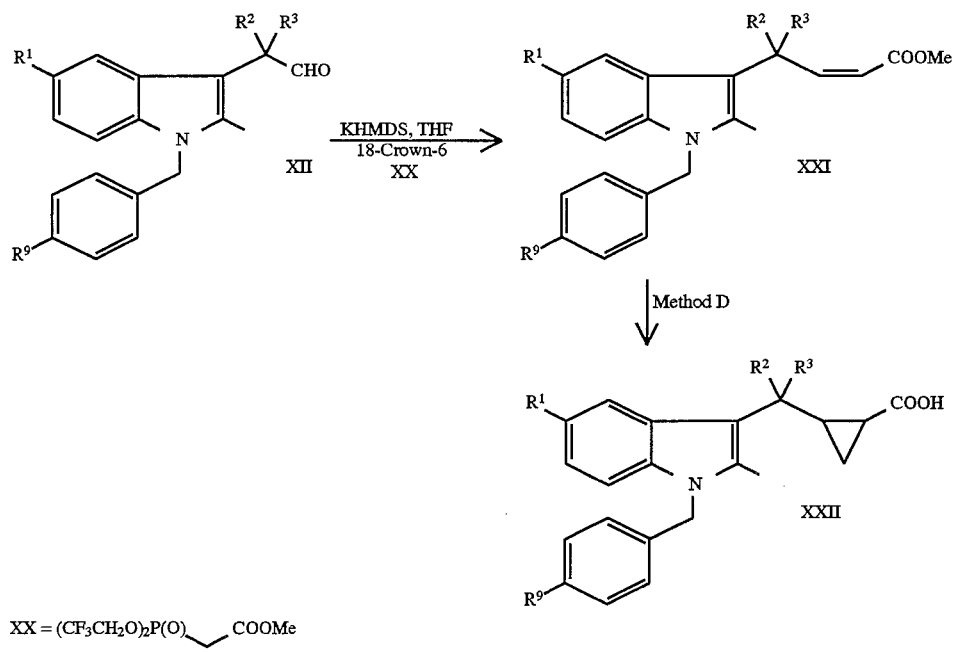
XX = (CF$_3$CH$_2$O)$_2$P(O)CH$_2$COOMe
METHOD F
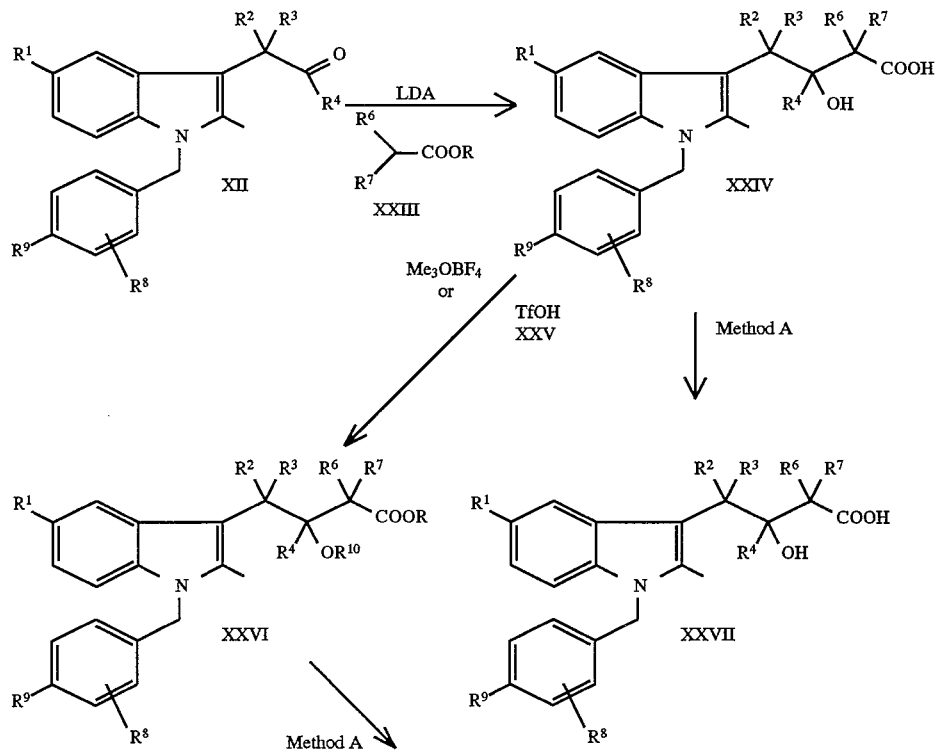

METHOD F
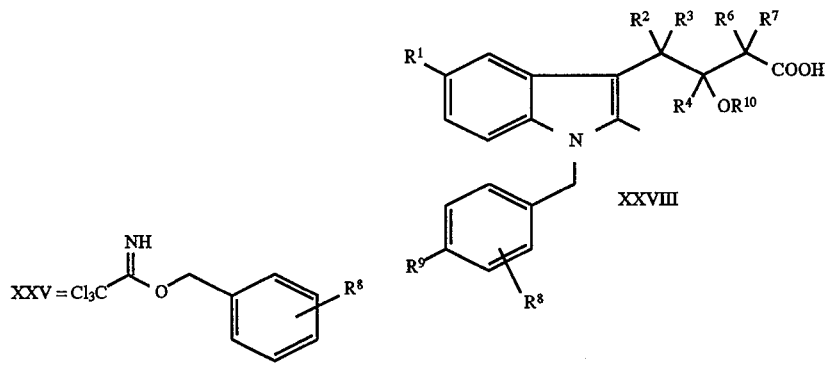
METHOD G
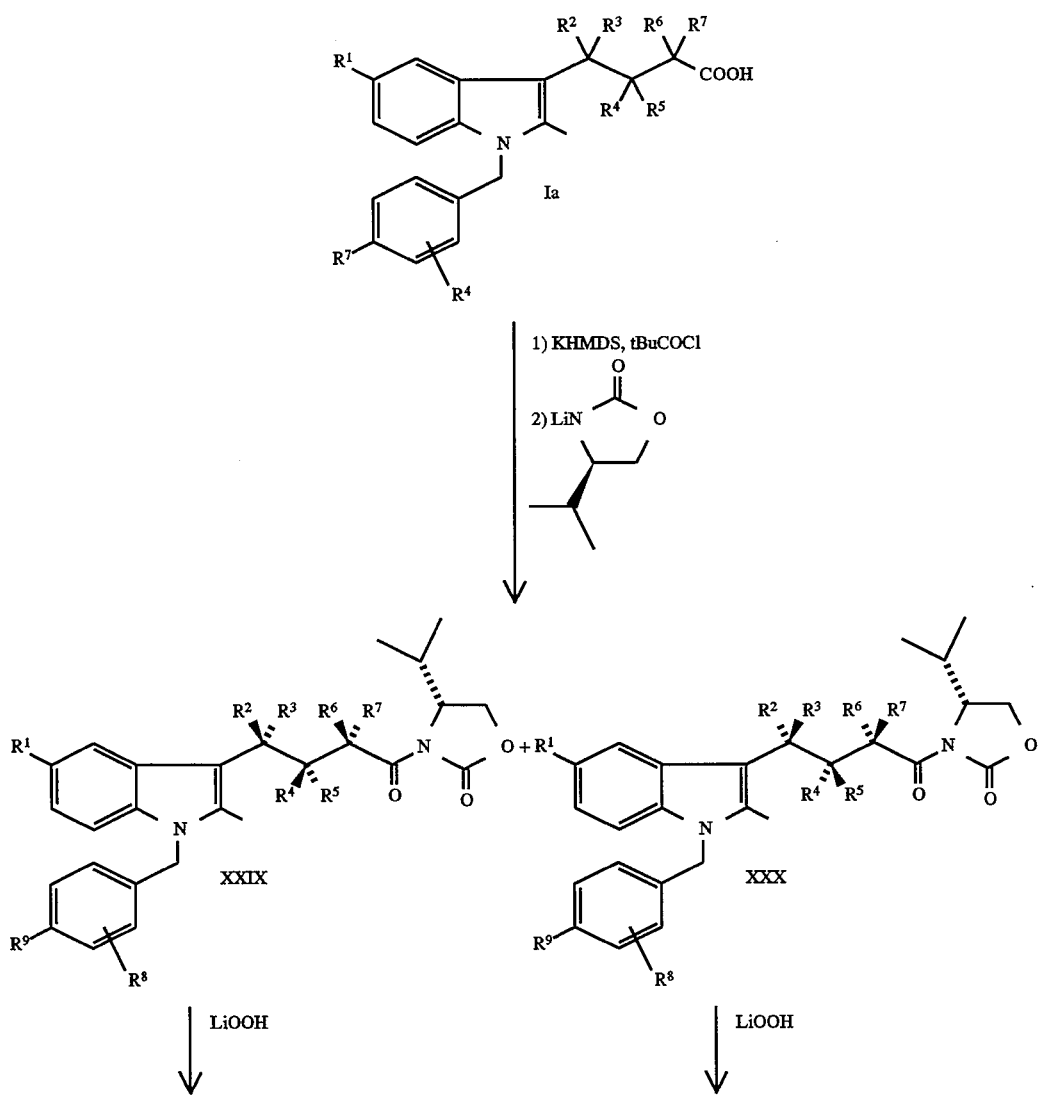

-continued
METHOD G
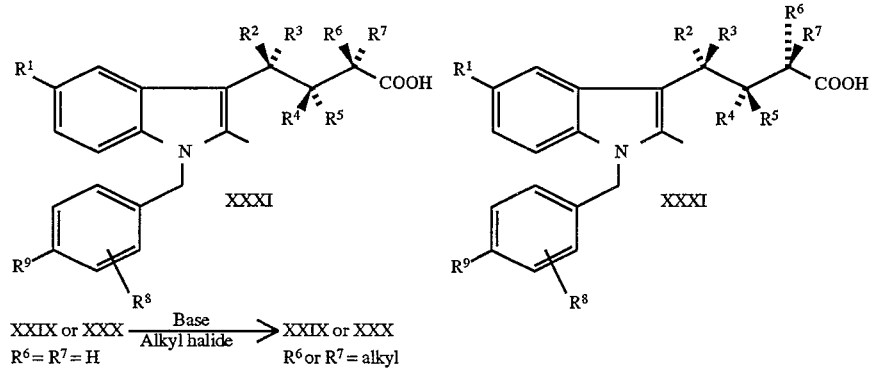
METHOD H
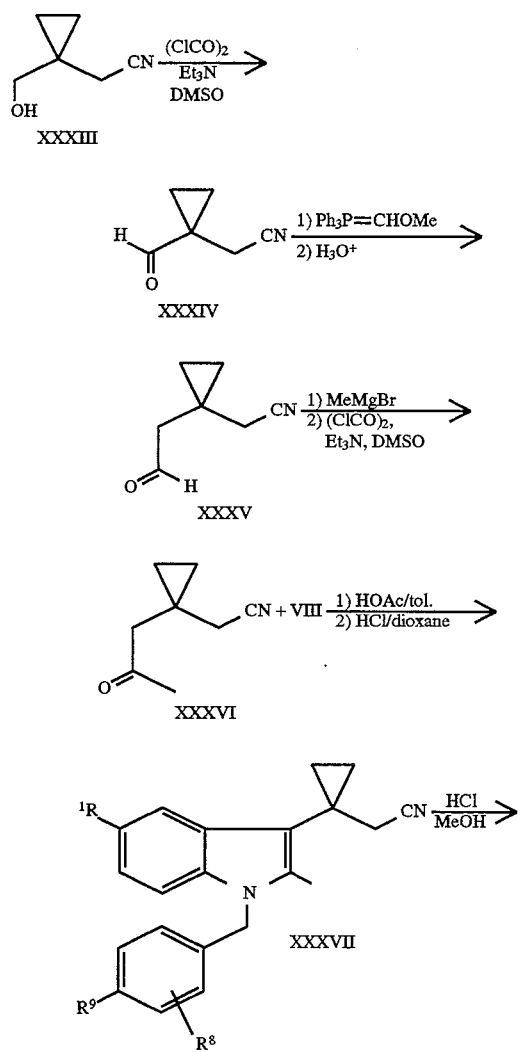
-continued
METHOD H
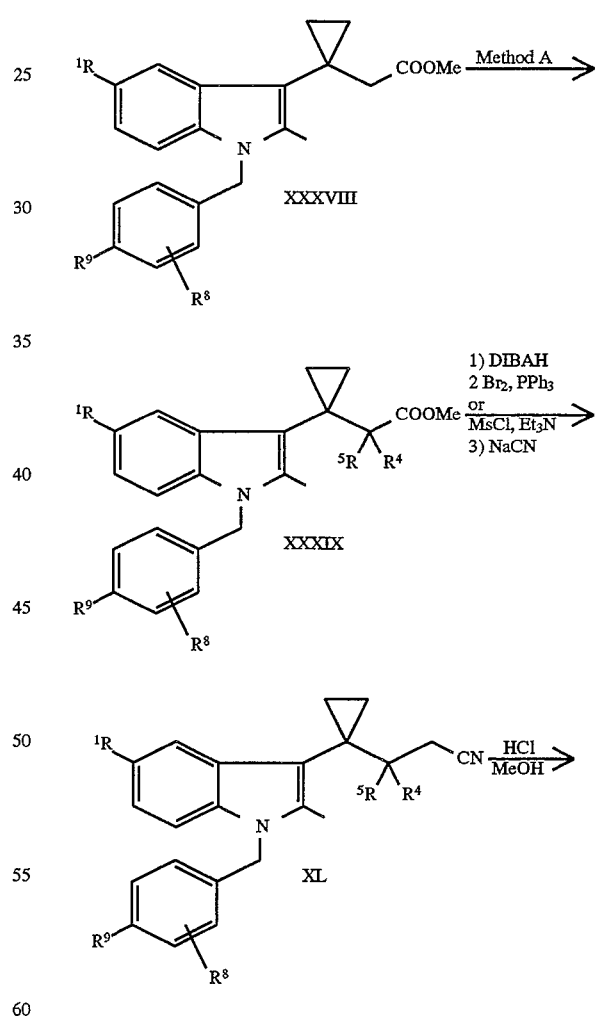

METHOD H
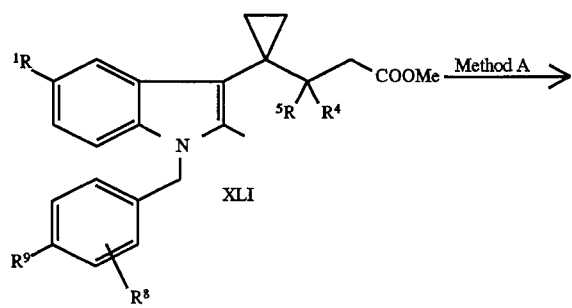
METHOD I
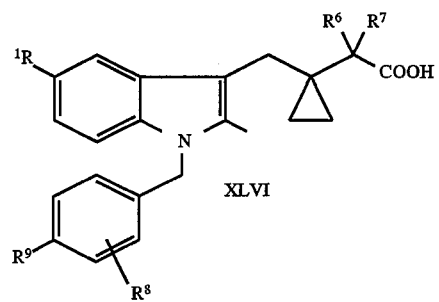
METHOD I
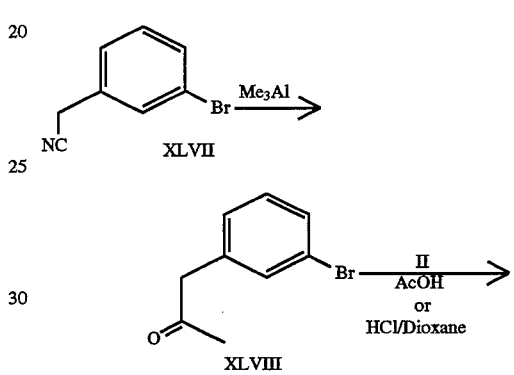
METHOD J
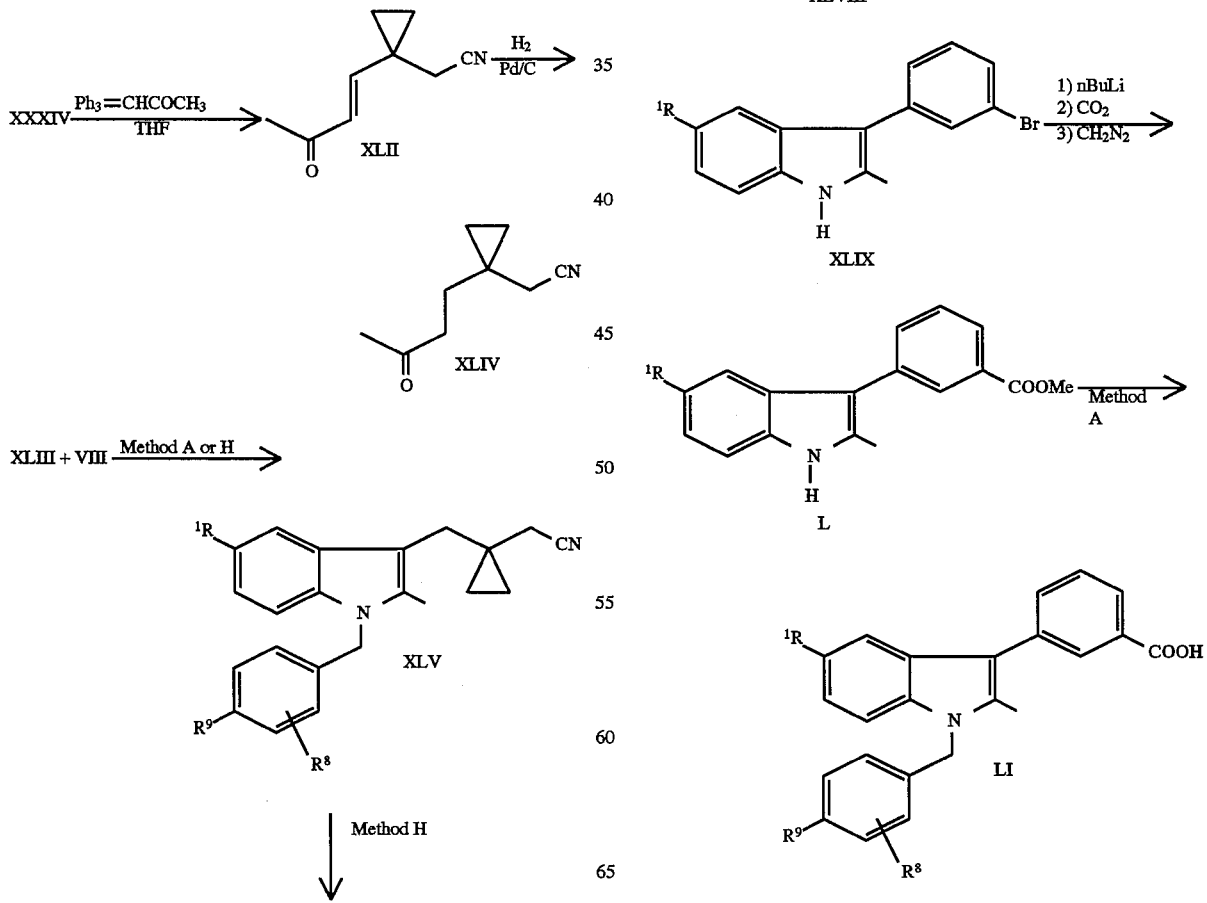

METHOD K
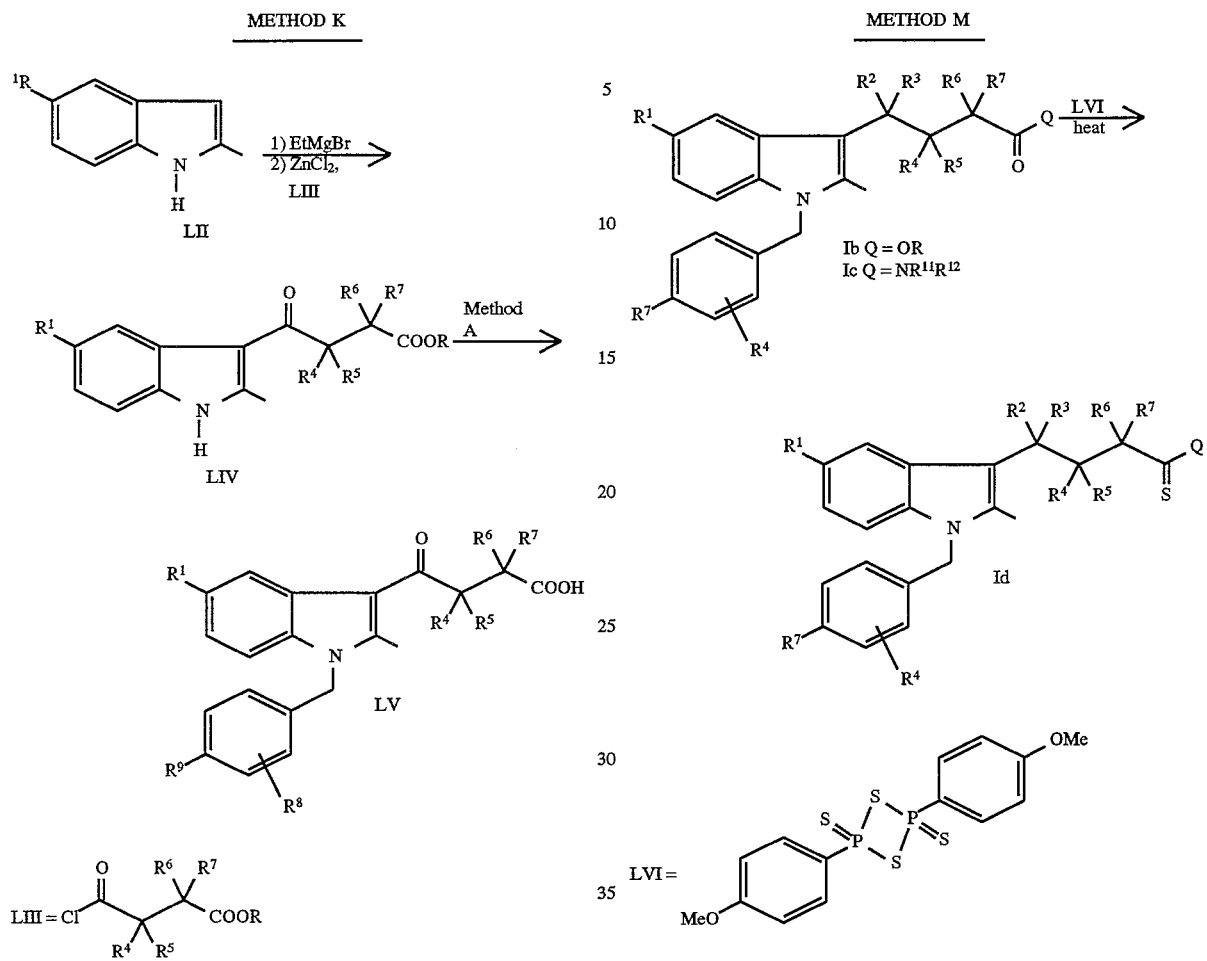
METHOD M
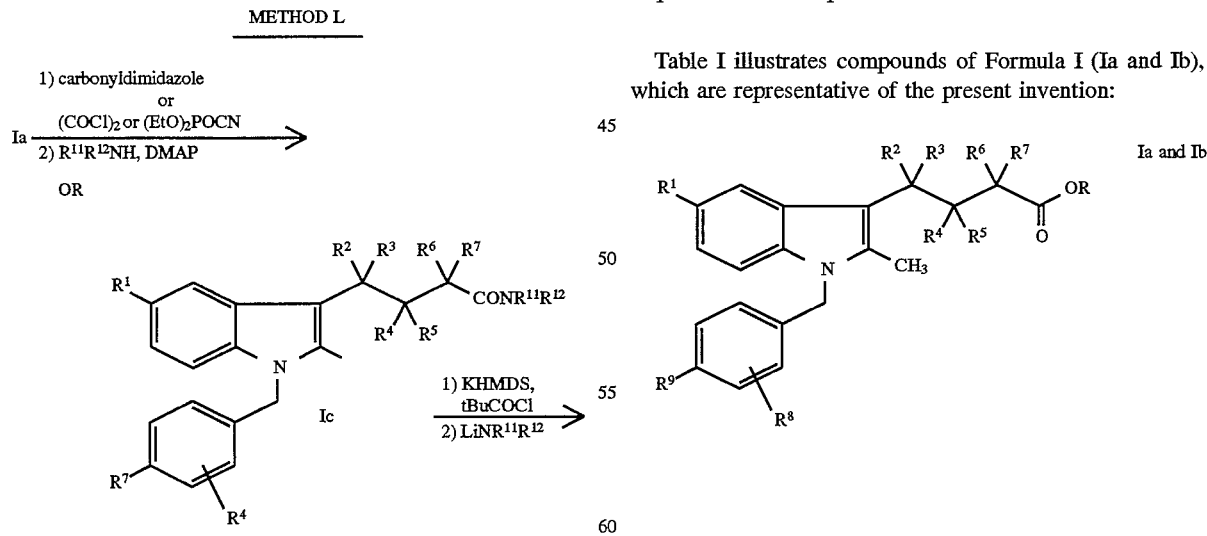
Representative Compounds
Table I illustrates compounds of Formula I (Ia and Ib), which are representative of the present invention:

TABLE I

| Example | Stereo | R | R¹ | R² | R³ | R⁴ | R⁵ | R⁶ | R⁷ | R⁸ | R⁹ |
|---|---|---|---|---|---|---|---|---|---|---|---|
| 1 | N/A | H | MeO | —CH₂CH₂— | | H | H | H | H | H | Br |
| 2 | N/A | H | MeO | H | H | —CH₂CH₂— | | H | H | H | Br |
| 3 | rac | H | MeO | H | H | H | H | H | CH₃ | H | Br |
| 4 | N/A | H | MeO | H | H | H | H | H | H | H | Br |
| 5 | N/A | H | MeO | H | H | H | H | CH₃ | CH₃ | H | Br |
| 6 | rac | H | MeO | H | H | H | H | OH | CH₃ | H | Br |
| 7 | S | H | MeO | H | H | H | CH₃ | H | H | H | Br |
| 8 | R | H | MeO | H | H | CH₃ | H | H | H | H | Br |
| 9 | rac | H | MeO | H | H | H | CH₃ | H | H | H | MeS |
| 10 | trans, rac | H | MeO | H | H | H | —CH₂— | | H | H | Br |
| 11 | 2R, 3S | H | MeO | H | H | H | CH₃ | H | CH₃ | H | Br |
| 12 | 2R, 3R | H | MeO | H | H | CH₃ | H | H | CH₃ | H | Br |
| 13 | 2S, 3R | H | MeO | H | H | CH₃ | H | CH₃ | H | H | Br |
| 14 | 2S, 3S | H | MeO | H | H | H | CH₃ | CH₃ | H | H | Br |
| 15 | syn, anti, rac | H | MeO | CH₃ | H | H | H | CH₃ | H | H | Br |
| 16 | N/A | H | MeO | —O— | | H | H | H | H | H | Br |
| 17 | cis, rac | H | MeO | H | H | H | —CH₂— | | H | H | Br |
| 18 | R | H | MeO | H | H | CH₃ | H | H | H | H | Br |
| 19 | N/A | H | Br | H | H | — | —CH=CH—CH=CH— | | — | H | Br |
| 20 | N/A | H | MeO | — | —CH=CH—CH=CH— | | — | H | H | H | Br |
| 21 | N/A | H | MeO | H | H | — | —CH=CH—CH=CH— | | — | H | Br |
| 22 | N/A | H | MeO | — | CH | H | — | CH=CH | — | H | Br |
| 23 | N/A | H | CH₃ | H | H | H | H | H | H | H | Br |
| 24 | N/A | H | Br | H | H | H | H | H | H | H | Br |
| 25 | N/A | H | MeO | H | H | —CH₂CH₂— | | H | H | H | Cl |
| 26 | N/A | H | Cl | H | H | H | H | H | H | H | Br |
| 27 | N/A | H | Br | H | H | H | H | H | H | H | Cl |
| 28 | N/A | H | Cl | H | H | H | H | H | H | H | Cl |
| 29 | N/A | H | Cl | H | H | H | H | H | H | 2-F | Br |
| 30 | rac | H | Cl | H | H | H | H | CH₃ | H | 2-F | Br |
| 31 | N/A | H | MeO | H | H | —CH₂CH₂— | | H | H | H | MeS |
| 32 | N/A | H | Br | H | H | —CH₂CH₂— | | H | H | H | Br |
| 33 | trans, rac | H | Cl | H | H | H | —CH₂— | | H | H | Br |
| 34 | rac | H | Cl | H | H | CH₃ | H | H | H | H | Br |
| 35 | rac | H | Cl | H | H | H | H | CH₃ | H | H | Br |
| 36 | syn, anti, rac | H | Cl | H | H | CH₃ | H | CH₃ | H | H | Br |
| 37 | rac | H | Cl | H | CH₃ | H | H | H | H | H | H |
| 38 | rac | H | Cl | H | CH₃ | H | H | H | H | H | Br |
| 39 | rac | H | MeO | H | H | CH₃ | H | H | H | H | Br |
| 40 | N/A | H | MeO | H | H | —CH₂CH₂— | | H | H | H | CH₃S(O) |
| 41 | rac | H | MeO | H | CH₃ | H | H | H | H | H | Br |
| 42 | syn, anti, rac | H | MeO | H | H | CH₃ | H | CH₃ | H | H | Br |
| 43 | S | H | Cl | H | H | CH₃ | H | H | H | H | Br |
| 44 | R | H | Cl | H | H | H | CH₃ | H | H | H | Br |
| 45 | rac | H | MeO | H | H | —CH₂CH₂— | | H | CH₃ | H | Br |
| 46 | rac | H | MeO | H | H | CH₃CH₂ | H | H | H | H | Br |
| 47 | syn, anti, rac | H | MeO | H | CH₃ | H | CH₃ | H | H | H | Br |
| 48 | N/A | H | MeO | H | H | CH₃ | CH₃ | H | H | H | Br |
| 49 | N/A | H | CF₃ | H | H | H | H | H | H | H | Br |
| 50 | R | H | Cl | H | H | H | H | CH₃ | H | H | Br |
| 51 | S | H | Cl | H | H | H | H | H | CH₃ | H | Br |
| 52 | rac | H | MeO | H | H | H | H | PhCH₂ | H | H | Br |
| 53 | N/A | H | Cl | H | H | H | H | H | H | H | I |
| 54 | rac | H | MeO | H | H | H | H | H | CH₃CH₂ | H | Br |
| 55 | N/A | H | Br | H | H | CH₃ | CH₃ | H | H | H | Br |
| 56 | N/A | H | Cl | H | H | CH₃ | CH₃ | H | H | H | Br |
| 57 | 2R, 3R | H | Cl | H | H | H | CH₃ | H | CH₃ | H | Br |
| 58 | 2S, 3R | H | Cl | H | H | H | CH₃ | CH₃ | H | H | Br |
| 59 | R | H | MeO | H | H | CH₃ | H | H | H | H | I |
| 60 | N/A | H | Cl | H | H | —CH₂CH₂— | | H | H | H | Br |
| 61 | R | H | MeO | H | H | CH₃ | H | H | H | H | CH₃CH₂S |
| 62 | N/A | Me | MeO | H | H | H | H | H | H | H | Br |
| 63 | N/A | H | MeO | —O— | | — | —CH=CH—CH=CH— | | — | H | Br |
| 64 | N/A | H | MeO | — | CH=CH | H | — | CH(CH₃) | — | H | Br |

TABLE I-continued

| Example | Stereo | R | R¹ | R² | R³ | R⁴ | R⁵ | R⁶ | R⁷ | R⁸ | R⁹ |
|---|---|---|---|---|---|---|---|---|---|---|---|
| 65 | rac | H | Cl | H | OH | H | H | H | H | 3-F | Br |
| 66 | N/A | Me | CH₃ | H | H | —O— | | H | H | H | MeO |
| 67 | N/A | H | CF₃O | H | H | —CH₂CH₂CH₂— | | H | H | H | Br |
| 68 | cis, rac | H | MeO | H | H | H | | —CH₂CH₂— | H | 2-F | MeS |
| 69 | trans, rac | H | MeO | H | —CH₂CH₂CH₂— | | H | H | MeO | H | Br |
| 70 | rac | H | MeO | PhCH₂ | H | H | H | F | F | H | Br |
| 71 | N/A | H | CH₂FO | H | H | Et | Et | H | H | 2-Cl | Cl |
| 72 | rac | H | Cl | H | H | 4-ClPh | H | H | H | H | Br |
| 73 | rac | H | MeO | H | PhCH₂O | H | H | —CH₂— | | H | Br |
| 74 | N/A | CH(CH₂CH₂) | MeO | H | H | H | H | H | H | H | Br |
| 75 | rac | H | MeO | Et | H | H | H | Cl | H | H | Br |
| 76 | N/A | Et | MeO | H | H | —CH₂CH₂CH₂— | | H | H | H | Br |
| 77 | N/A | H | MeO | F | F | H | H | H | H | H | SCF₃ |
| 78 | cis, rac | H | CH₃ | H | —CH₂ | H | H | CH₂CH₂ | H | 2-F | Cl |
| 79 | N/A | H | MeO | H | H | CH₃ | CH₃ | F | F | H | Br |
| 80 | cis, trans rac | H | MeO | CH₃ | —CH₂— | | CH₃ | H | H | H | Br |
| 81 | cis, rac | H | F | H | —CH₂CH₂CH₂— | | OH | H | H | H | OCF₃ |
| 82 | rac | H | Br | H | H | 4-MeS(O)PhCH₂ | H | H | H | H | SMe |
| 83 | rac | H | MeO | H | CH₃ | H | H | MeSO₂ | H | H | Br |
| 84 | rac | CF₃CF₂ | MeO | H | H | —CH₂—O— | | H | H | H | Br |
| 85 | rac | H | MeO | H | —CH₂OCH₂— | | H | H | H | H | Br |
| 86 | rac | H | MeO | — | —CH=CH —CH=CH— | | — | H | CH₃ | H | Br |
| 87 | rac | H | I | H | H | CH₃ | CH₃ | Cl | H | 2-Br | Br |
| 88 | rac | H | MeO | OH | CH₃ | OH | CH₃ | H | H | H | Br |
| 89 | rac | H | MeO | H | CH₃ | H | H | CF₃ | CF₃ | H | Br |

Table II illustrates compounds of Formula Ic, which are representative of the present invention:

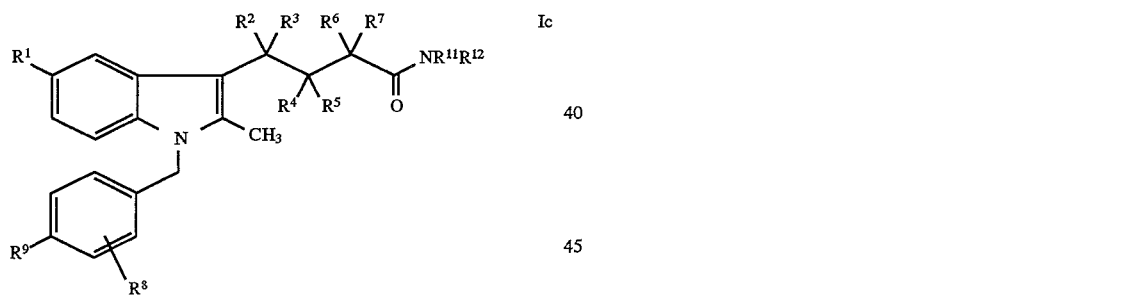

Ic

TABLE II

| Example | Stereo | R¹ | R² | R³ | R⁴ | R⁵ | R⁶ | R⁷ | R⁸ | R⁹ | R¹¹ | R¹² |
|---|---|---|---|---|---|---|---|---|---|---|---|---|
| 90 | rac | MeO | H | H | H | CH₃ | H | H | H | Br | H | H |
| 91 | N/A | MeO | H | H | H | H | H | H | H | Br | H | 2-Pyridyl |
| 92 | N/A | MeO | H | H | —CH₂CH₂— | | H | H | H | Br | H | SO₂CH₃ |
| 93 | R | MeO | H | H | H | CH₃ | H | H | H | Br | H | H |
| 94 | R | MeO | H | H | H | CH₃ | H | H | H | Br | CH₃ | CH₃ |
| 95 | rac | MeO | H | H | H | CH₃ | H | H | H | Br | H | —CH₂CH₂OH |
| 96 | R | MeO | H | H | H | CH₃ | H | H | H | Br | H | —CH₂CH₂NMe₂ |
| 97 | N/A | MeO | — | CH | H | — | CH=CH | — | H | Br | H | —CH₂CH₂OH |
| 98 | N/A | MeO | — | CH | H | — | CH=CH | — | H | Br | CH₂CH₂OH | —CH₂CH₂OH |
| 99 | N/A | MeO | — | CH | H | — | CH=CH | — | H | Br | H | H |
| 100 | N/A | MeO | H | H | H | H | H | H | H | Br | H | 4-Pyridyl |
| 101 | rac | MeO | H | H | H | CH₃ | H | H | H | Br | H | —CH₂CH₂—N(CH₂)₄ |
| 102 | N/A | MeO | H | H | H | H | H | H | H | Br | H | 3-Pyridyl |
| 103 | N/A | MeO | H | H | H | H | H | H | H | Br | H | H |
| 104 | N/A | MeO | H | H | H | H | H | H | H | Br | H | CH₃ |

TABLE II-continued

| | | | | | | | | | | | | |
|---|---|---|---|---|---|---|---|---|---|---|---|---|
| 105 | N/A | MeO | — | CH | H | — | CH=CH | — | H | Br | H | SO$_2$CH$_3$ |

| Example | Stereo | R$^1$ | R$^2$ | R$^3$ | R$^4$ | R$^5$ | R$^6$ | R | R | R$^8$ | R$^{11}$ | R$^{12}$ |
|---|---|---|---|---|---|---|---|---|---|---|---|---|
| 106 | N/A | MeO | H | H | — | —CH=CH—CH=CH— | | — | H | Br | H | SO$_2$CH$_3$ |
| 107 | rac | Cl | H | H | —CH$_2$CH$_2$CH$_2$— | | H | F | H | Cl | H | C(O)CH$_3$ |
| 108 | cis | MeO | H | —CH$_2$CH$_2$— | | H | H | H | 2-F | Br | H | SO$_2$Ph |
| 109 | rac | MeO | H | CF$_3$ | H | H | Cl | Cl | H | Br | H | CH$_3$ |
| 110 | trans, rac | Br | H | —CH$_2$— | | H | H | H | H | F | H | —CH$_2$CH$_2$SMe |
| 111 | rac | MeO | H | H | H | Ph | H | H | H | Br | Me | MeO— |
| 112 | rac | MeO | H | PhCH$_2$— | H | H | SO$_2$Me | H | H | Br | H | —CH(CH$_2$)$_2$ |
| 113 | rac | MeO | H | H | H | —O— | | H | H | Cl | H | SO$_2$CF$_3$ |
| 114 | N/A | MeS | H | H | H | H | CH$_3$ | CH$_3$ | H | Br | H | C(O)CF$_3$ |
| 115 | rac | MeO | H | H | H | —CH(CH$_2$)$_2$ | H | H | H | Br | H | (CH$_2$)$_3$SO$_2$Me |

Table III illustrates compounds of Formula I, which are representative of the present invention

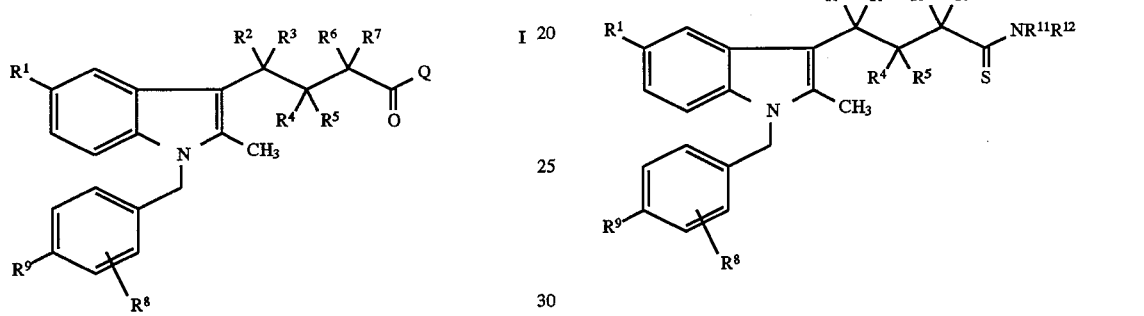

TABLE III

| Example | Stereo | R$^1$ | R$^2$ | R$^3$ | R$^4$ | R$^5$ | R$^6$ | R$^7$ | R$^8$ | R$^9$ | Q |
|---|---|---|---|---|---|---|---|---|---|---|---|
| 116 | rac | MeO | H | H | H | CH$_3$ | H | H | H | Br | 1-(4-methyl-piperazinyl) |
| 117 | N/A | MeO | H | H | —CH$_2$CH$_2$— | | H | H | H | Br | 1-imidazolyl |
| 118 | R | MeO | H | H | H | CH$_3$ | H | H | H | Br | N-morpholinyl |
| 119 | S, R | MeO | H | H | CH$_3$ | H | H | H | H | Br | N-(4(R)-isopropyl-2-oxazolidinone) |
| 120 | R, R | MeO | H | H | H | CH$_3$ | H | H | H | Br | N-(4(R)-isopropyl-2-oxazolidinone) |
| 121 | rac | MeO | H | CH$_3$ | H | H | H | H | H | Br | N-(2-oxazolidinone) |
| 122 | rac | MeO | H | CH$_3$ | H | H | H | CH$_3$ | H | Br | N-(2-oxazolidinone) |
| 123 | cis, rac | MeO | H | H | H | —CH$_2$— | | H | 2-F | Br | N-aziridinyl |
| 124 | N/A | CH$_3$ | H | H | —CH$_2$CH$_2$— | | H | H | H | MeS | 1,2,4-triazol-1-yl |
| 125 | | MeO | H | H | H | H | MeO | H | H | Br | N-thiazolidinyl |

Table IV illustrates compounds of Formula Id, which are representative of the present invention

TABLE IV

| Example | Stereo | R$^1$ | R$^2$ | R$^3$ | R$^4$ | R$^5$ | R$^6$ | R$^7$ | R$^8$ | R$^9$ | R$^{11}$ | R$^{12}$ |
|---|---|---|---|---|---|---|---|---|---|---|---|---|
| 126 | rac | MeO | H | H | H | CH$_3$ | H | H | H | Br | H | H |
| 127 | rac | MeO | H | H | H | CH$_3$ | H | H | H | Br | H | CH$_3$ |
| 128 | rac | Cl | H | H | H | CH$_3$ | H | H | H | Br | H | H |
| 129 | N/A | MeO | H | H | H | H | H | H | H | Br | H | H |
| 130 | N/A | MeO | H | H | H | H | H | H | H | Br | H | CH$_3$ |

TABLE IV-continued

| Example | Stereo | R¹ | R² | R³ | R⁴ | R⁵ | R⁶ | R⁷ | R⁸ | R⁹ | R¹¹ | R¹² |
|---|---|---|---|---|---|---|---|---|---|---|---|---|
| 131 | R | MeO | H | H | H | CH₃ | H | H | H | Br | H | H |
| 132 | N/A | MeO | H | H | — | CH=CH—CH=CH | | — | H | Br | H | H |
| 133 | rac | CH₃ | —CH₂— | | H | H | H | Ph | H | Br | H | SO₂CH₃ |
| 134 | N/A | MeO | H | H | H | H | Cl | Cl | 2-F | Br | H | H |
| 135 | trans | MeO | H | —CH₂CH₂— | | H | H | H | H | MeS | H | CH(CH₂)₂ |
| 135 | N/A | Br | H | H | H | H | —CH₂CH₂— | | H | Br | H | Ph |
| 136 | N/A | MeO | H | H | | —CH—CH—O— | | | H | Br | H | OCH₃ |

Assays for Determining Biological Activity

The compound of Formula I can be tested using the following assays to determine their cyclooxygenase-2 inhibiting activity.

Inhibition of Cyclooxygenase Activity

Compounds were tested as inhibitors of cyclooxygenase activity in whole cell cyclooxygenase assays. Both of these assays measured prostaglandin E₂ synthesis in response to arachidonic acid, using a radioimmunoassay. Cells used for these assays were human osteosarcoma 143 cells (which specifically express cyclooxygenase-2) and human U-937 cells (which specifically express cyclooxygenase-1). In these assays, 100% activity is defined as the difference between prostaglandin E₂ synthesis in the absence and presence of arachidonate addition.

Assay

For cyclooxygenase assays, osteosarcoma cells are cultured in 1 mL of media in 24-well multidishes (Nunclon) until confluent (1–2×10⁵ cells/well). U-937 cells are grown in spinner flasks and resuspended to a final density of 1.5×10⁶ cells/mL in 24-well multidishes (Nunclon). Following washing and resuspension of osteosarcoma and U-937 cells in 1 mL of Hanks balanced salts solution (HBSS), 2 mL of a DMSO solution of test compound or DMSO vehicle is added, and samples gently mixed. All assays are performed in triplicate. Samples are then incubated for 5 or 15 minutes at 37° C., prior to the addition of arachidonic acid. Arachidonic acid (peroxide-free, Cayman Chemical) is prepared as a 10 mM stock solution in ethanol and further diluted 10-fold in HBSS. An aliquot of 10 mL of this diluted solution is added to the cells to give a final arachidonic acid concentration of 10 mM. Control samples are incubated with ethanol vehicle instead of arachidonic acid. Samples are again gently mixed and incubated for a further 10 rain at 37° C. For osteosarcoma cells, reactions are then stopped by the addition of 100 mL of 1N HCl, with mixing and by the rapid removal of the solution from cell monolayers. For U-937 cells, reactions are stopped by the addition of 100 mL of 1N HCl, with mixing. Samples are then neutralized by the addition of 100 mL of 1N NaOH and PGE₂ levels measured by radioimmunoassay.

Rat Paw Edema Assay-Protocol

Male Sprague-Dawley rats (150–200 g) are fasted overnight and are given po either vehicle (1% methocel or 5% Tween 80) or a test compound. One hr later, a line is drawn using a permanent marker at the level above the ankle in one hind paw to define the area of the paw to be monitored. The paw volume (V₀) is measured using a plethysmometer (Ugo-Basile, Italy) based on the principle of water displacement. The animals are then injected subplantarly with 50 ml of 1% carrageenan solution in saline (FMC Corp, Maine) into the paw using an insulin syringe with a 25-gauge needle (i.e., 500 mg carrageenan per paw). Three hr later, the paw volume (V₃) is measured and the increases in paw volume (V₃–V₀) are calculated. The animals are sacrificed by CO₂ asphyxiation and the absence or presence of stomach lesions scored. Data is compared with the vehicle-control values and percent inhibition calculated. All treatment groups are coded to eliminate observer bias.

NSAID-Induced Gastrophathy in Rats

Rationale

The major side effect of conventional NSAIDs is their ability to produce gastric lesions in man. This action is believed to be caused by inhibition of Cox-1 in the gastrointestinal tract. Rats are particularly sensitive to the actions of NSAIDs. In fact, rat models have been used commonly in the past to evaluate the gastrointestinal side effects of current conventional NSAIDs. In the present assay, NSAID-induced gastrointestinal damage is observed by measuring fecal $^{51}$Cr excretion after systemic injection of $^{51}$Cr-labeled red blood cells. Fecal $^{51}$Cr excretion is a well-established and sensitive technique to detect gastrointestinal integrity in animals and man.

Methods

Male Sprague Dawley rats (150–200 g) are administered orally a test compound either once (acute dosing) or b.i.d. for 5 days (chronic dosing). Immediately after the administration of the last dose, the rats are injected via a tail vein with 0.5 mL of $^{51}$Cr-labeled red blood cells from a donor rat. The animals are placed individually in metabolism cages with food and water ad lib. Feces are collected for a 48 h period and $^{51}$Cr fecal excretion is calculated as a percent of total injected dose. $^{51}$Cr-labeled red blood cells are prepared using the following procedures. Ten mL of blood is collected in heparinized tubes via the vena cava from a donor rat. Plasma is removed by centrifugation and replenished with equal volume of Hanks' balanced salt solution (HBSS). The red blood cells are incubated with 400 mCi of sodium $^{51}$chromate for 30 rain at 37° C. At the end of the incubation, the red blood cells are washed twice with 20 mL HBSS to remove free sodium $^{51}$chromate. The red blood cells are finally reconstituted in 10 mL HBSS and 0.5 mL of the solution (about 20 mCi) is injected per rat.

Protein-Losing Gastropathy in Squirrel Monkeys

Rationale

Protein-losing gastropathy (manifested as appearance of circulating cells and plasma proteins in the GI tract) is a significant and dose-limiting adverse response to standard non-steroidal anti-inflammatory drags (NSAIDs). This can be quantitatively assessed by intravenous administration of 51CrCl3 solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods

Groups of male squirrel monkeys (0.8 to 1.4 kg) are treated by gavage with either 1% methocell or 5% Tween 80 in H₂O vehicles, (3 mL/kg b.i.d.) or test compounds at doses from 1–100 mg/kg b.i.d. for 5 days. Intravenous $^{51}$Cr (5 mCi/kg in 1 ml/kg phosphate buffer saline (PBS)) is administered 1 h after the last drug/vehicle dose, and feces collected for 24 h in a metabolism cage and assessed for excreted $^{51}Cr$ by gamma-counting. Venous blood is sampled 1 h and 8 h after the last drug dose, and plasma concentrations of drug measured by RP-HPLC.

Representative Biological Data

Compounds of the present invention are inhibitors of cyclooxygenase-2 and are thereby useful in the treatment of cyclooxygenase-2 mediated diseases as enumerated above. The activities of the compounds against cyclooxygenase may be seen in the representative results shown below. In the assay, inhibition is determined by measuring the amount of prostaglandin $E_2$ ($PGE_2$) synthesized in the presence of arachidonic acid, cyclooxygenase-1 or cyclooxygenase-2 and a putative inhibitor. The $IC_{50}$ values represent the concentration of putative inhibitor required to return $PGE_2$ synthesis to 50% of that obtained as compared to the uninhibited control.

Representative results for the inhibition of $PGE_2$ production and edema inhibition may be seen in Table V. For comparison purposes, the Table also contains data for the conventional NSAID indomethacin and for the compound a-(1-p-chlorobenzyl-2-methyl-5-methoxy-3-indolyl) propionic acid (also known as MK-555). This latter compound is disclosed in British Patent Specification 957,990 (May 13, 1964) as having anti-inflammatory activity.

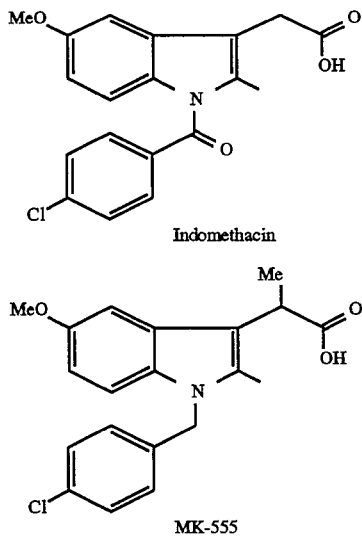

Indomethacin

MK-555

TABLE V

| Example | Cox-1 $IC_{50}(nM)$ | Cox-2 $IC_{50}(nM)$ | $ED_{30}(mg/kg)$ |
|---|---|---|---|
| 25 | >25,000 | 9 | >3.0 |
| 24 | >50,000 | 6 | ~3.0 |
| 4 | >10,000 | 6 | 1.2 |
| 2 | >100,000 | 16 | 0.54 |
| 34 | >10,000 | 5 | 0.51 |
| 8 | >10,000 | 32 | 0.6 |
| MK-555 | 10,000 | 10 | 3.0 |
| Indomethacin | 10 | 10 | 0.9 |

The following abbreviations have the indicated meanings:
Ac=acetyl
Bn=benzyl
DMAP=4-(dimethylamino)pyridine
DMF=N,N-dimethylformamide
DMSO=dimethyl sulfoxide
$Et_3N$=triethylamine
HMPA=hexamethylphosphoric triamide
KHMDS=potassium hexamethyldisilazane
LDA=lithium diisopropylamide
LiHMDS=lithium hexamethyldisilazane
Ms=methanesulfonyl=mesyl
MsO=methanesulfonate=mesylate
NSAID=non-steroidal anti-inflammatory drug
PCC=pyridinium chlorochromate
Ph=phenyl
r.t.=room temperature
rac.=racemic
THF=tetrahydrofuran
TLC=thin layer chromatography
Alkyl group abbreviations
Me=methyl
Et=ethyl Substituted benzyl, substituted phenyl and substituted pyridyl means that the aromatic ring carries 1 or 2 substituents selected from halo, methoxy, methylthio, trifluoromethyl, methyl or ethyl.

Halo includes F, Cl, Br, and I. The invention will now be illustrated by the following non-limiting examples in which, unless stated otherwise: all operations were carried out at room or ambient temperature, that is, at a temperature in the range 18°–25° C.; evaporation of solvent was carried out using a rotary evaporator under reduced pressure (600–4000 pascals: 4.5–30 mm Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (d) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.; chemical symbols have their usual meanings; the following abbreviations have also been used b.p. (boiling point), m.p. (melting point), L (liter(s)), mL (milliliters), g (gram(s)), mg (milligrams(s)), mol (moles), mmol (millimoles).

EXAMPLE 1

3-[1-(1-(4-Bromobenzyl)-5-methoxy-2-methyl-1H-indol-3-yl)-cyclopropyl]propanoic acid Step 1: (1-Formylcyclopropane)acetonitrile To a room temperature suspension of PCC (32.3 g, 150 mmol) and celite (35 g) in 200 mL $CH_2Cl_2$ was added (1-hydroxymethylcyclopropane)acetonitrile (Eur. Pat. 604, 114, Example 1, Step 7, Case 18907, 11.1 g, 100 mmol) in 20 mL $CH_2Cl_2$ over 15 min. The mixture was stirred 4 h, then filtered through a 1:1 mixture of celite and silica gel, washing with 50% ether/$CH_2Cl_2$. The filtrate was concentrated in vacuo, then dissolved in $CH2Cl_2$ and dried over $MgSO_4$, filtered and evaporated to give 10.6 g of the title compound.

$^1$H NMR (CD$_3$COCD$_3$) δ 8.65 (1H, s), 2.75 (2H, s), 1.2–1.5 (4H, m).

Step 2: [1-(2-Oxoethyl)cyclopropyl]acetonitrile

To a −5° C. suspension of (methoxymethyl) triphenylphosphonium chloride (28.3 g, 82.5 mmol) in 160 mL THF was added potassium t-butoxide (1.75M solution in THF, 46 mL, 81 mmol). The deep orange mixture was stirred 15 min, then transferred dropwise via cannula into a −5° C. solution of the aldehyde from Step 1 (6.0 g, 55 mmol) in 115 mL THF. After stirring 2 h at 0° C., the reaction mixture was partitioned between 1M HCl and ethyl acetate. The organic layer was washed with brine, dried over MgSO$_4$, filtered and evaporated. The residue was filtered through a plug of silica gel with 20% ethyl acetate/hexanes to provide the intermediate enol ether. This material was dissolved in 110 mL of methanol and treated with 30 mL of 4N HCl and refluxed overnight. The cooled reaction mixture was partitioned between water and ethyl acetate. The organic layer was washed with brine, dried over MgSO$_4$, filtered and evaporated. Purification by flash chromatography (15% ethyl acetate/hexanes) provided 3.0 g of the title compound.

$^1$H NMR (CD$_3$COCD$_3$) δ9.8 (1H, s), 2.65 (2H, s), 2.55 (2H, d), 0.7–0.5 (4H, m).

Step 3: [1-(2-Hydroxypropyl)cyclopropyl]acetonitrile

To a −5° C. solution of the aldehyde from Step 2 (3.00 g, 24.4 mmol) in 65 mL of THF was added methyl magnesium chloride (3.0M solution in THF, 9.5 mL, 29 mmol) and the reaction was stirred 2 h at 0° C. The reaction was quenched with 1M HCl and extracted with ethyl acetate. The organic extracts were washed with saturated NaHCO$_3$ and brine and dried over MgSO$_4$. Purification by flash chromatography (30% ethyl acetate/hexanes) provided 2.46 g of the title product.

$^1$H NMR (CD$_3$COCD$_3$) δ4.0–3.75 (1H, m), 3.6 (1H, d), 2.85–2.40 (2H, m), 1.25–1.75 (2H, m), 1.10 (3H, d), 0.6–0.4 (4H, m).

Step 4: [1-(2-Oxopropyl)cyclopropyl]acetonitrile

To a −78° C. solution of oxalyl chloride (0.70 mL, 8.0 mmol) in 40 mL of CH$_2$Cl$_2$ was added DMSO (0.62 mL, 8.7 mmol) and the resulting solution was stirred for 10 min. A solution of the alcohol from Step 3 (2.46 g, 17.7 mmol) in 5 mL CH$_2$Cl$_2$ was then added, and the mixture stirred 1 h at −78° C. Triethylamine (4.2 mL, 30 mmol) was then added, and the solution was allowed to warm to room temperature and stirred overnight. The reaction mixture was then partitioned between 1M HCl and CH$_2$Cl$_2$, and the organic layer was washed with saturated NaHCO$_3$ and brine, dried over MgSO$_4$ and evaporated. Purification of the residue by flash chromatography (25% ethyl acetate/hexanes) provided 927 mg of the title compound.

$^1$H NMR (CD$_3$COCD$_3$) δ2.7–2.5 (4H, m), 2.1 (3H, s), 0.6–0.4 (4H, m).

Step 5: N-(p-Bromobenzyl)-N-(4-methoxyphenyl)hydrazine hydrochloride

A mixture of 4-methoxyphenylhydrazine hydrochloride (459 g, 2.63 mol), 4-bromobenzyl bromide (715 g, 2.86 mol) and milled potassium carbonate (771 g, 5.58 mol) was suspended in 2 L DMF at 0° C. with overhead stirring. The ice bath was removed and the mixture was stirred for 4 h, then diluted with 15 L of ice water. The mixture was stirred vigorously for 1 h, then the aqueous layer was decanted from the gummy solid. The solid was washed with 2×4 L of water, then was dissolved in 2.5 L toluene and dried over Na$_2$SO$_4$. The mixture was filtered, and the filtrate was cooled in an ice bath and treated with a stream of HCl gas for 1 h with vigourous stirring. The precipitate was filtered and washed with 3×0.5 L of cold toluene and dried under a stream of nitrogen to give 682 g of the title compound.

$^1$H NMR (CD$_3$SOCD$_3$) δ10.5 (2H, br, s), 7.50 (2H, m), 7.23 (4H, m), 6.90 (2H, m), 4.52 (2H, s), 3.68 (3H, s).

Step 6: [1-(1-(p-Bromobenzyl)-5-methoxy-2-methyl-1H-indol-3-yl)-cyclopropyl]acetonitrile To a 0° C. mixture of the ketone from Step 4 (920 mg, 6.71 mmol) and the hydrazine from Step 5 (2.15 g, 7.0 mmol) in 35 mL toluene was added acetic acid (0.97 mL, 17 mmol). The mixture was warmed to room temperature and stirred 1 h, then concentrated to dryness. The residue was dissolved in toluene and heptane and concentrated again and the process repeated until there was no more acetic acid remaining. The residue was then dissolved in 30 mL dioxane and treated with HCl (4M solution in dioxane, 4 mL, 16 mmol). The mixture was heated to 60° C. for 1.5 h, then cooled and partitioned between water and ethyl acetate. The organic phase was washed with saturated NaHCO$_3$ and brine, dried over MgSO$_4$ and evaporated. Purification by flash chromatography (15% ethyl acetate/hexanes) provided 2.32 g of the title compound.

$^1$H NMR (CD$_3$COCD$_3$) δ7.50–6.65 (7H, m), 5.35 (2H, s), 3.8 (3H, s), 2.75 (2H, s), 2.45 (3H, s), 1.1–0.85 (4H, m).

Step 7: Methyl [1-(1-(p-bromobenzyl)-5-methoxy-2-methyl-1H-indol-3-yl)cyclopropyl]acetate To a −5° C. suspension of the nitrile from Step 6 (1.59 g, 3.88 mmol) in 15 mL methanol was added HCl gas to give a saturated solution. The mixture was then heated to reflux overnight, cooled and poured into ice water. The mixture was adjusted to pH 10 with 2.0N NaOH, and then extracted with ethyl acetate. The organic extracts were washed with saturated NaHCO$_3$ and brine, dried over MgSO$_4$ and evaporated. Purification by flash chromatography (15% ethyl acetate/hexanes) provided 1.63 g of the title compound.

$^1$H NMR (CD$_3$COCD$_3$) δ6.65–7.50 (7H, m), 5.30 (2H, s), 3.85 (3H, s), 3.45 (3H, s), 2.50 (2H, s), 2.30 (2H, s), 0.85–1.1 (4H, m).

Step 8: 2-[1-(1-(4-Bromobenzyl)-5-methoxy-2-methyl-1H-indol-3-yl) cyclopropyl]ethanol To a −78° C. solution of ester from Step 7 (442 mg, 1 mmol) in 5 mL THF was added DIBAH (1.5M in toluene, 2 mL, 3 mmol), and the mixture was stirred for 2 hours with slow warming to 0° C. The reaction mixture was partitioned between 1N HCl and ethyl acetate. The organic layer was washed with brine, dried over MgSO$_4$ and evaporated. The residue was filtered through a plug of silica gel to give 319 mg of the title compound which was used without further purification.

Step 9: 2-[1-(1-(4-Bromobenzyl)-5-methoxy-2-methyl-1H-indol-3-yl)cyclopropyl]ethyl bromide Bromine (136 mg, 0.85 mmol) was added to a −78° C. solution of triphenylphosphine (244 mg, 0.93 mmol) in 4 mL CH$_2$Cl$_2$, and the mixture was stirred 0.5 h at 0° C. and 5 min at r.t. before recooling to −5° C. The alcohol from Step 8 (319 mg, 0.77 mmol) was then slowly added as a 1 mL CH$_2$Cl$_2$ solution and the mixture was stirred 2 h at 0° C. The reaction mixture was partitioned between CH$_2$Cl$_2$ and saturated NaHCO$_3$. The organic layer was dried over MgSO$_4$, concentrated and the residue purified by flash chromatography (10% ethyl acetate in hexane) to give 166 mg of the title compound.

$^1$H NMR (CD$_3$COCD$_3$) δ7.45(2H,d) 7.2 (1H, d), 7.18 (1H, d), 6.7 (1H, dd), 5.35 (2H, s), 3.8 (3H, s), 3.45 (2H, t), 2.42 (3H, s), 2.11 (2H, t), 0.92 (2H, m), 0.75 (2H, m).

Step 10: 3-[1-(1-(4-Bromobenzyl)-5-methoxy-2-methyl-1H-indol-3-yl)cyclopropyl]propionitrile To a r.t. solution of bromide from Step 9 (166 mg, 0.35 mmol) in 4 mL DMF was added NaH$_2$PO$_4$·H$_2$O (138 mg, 1 mmol) followed by NaCN (49 mg, 1 mmol) and the resulting mixture was warmed to 75° C. for 2 h. After diluting with excess H$_2$O, the mixture was extracted with Et$_2$O. The organic layer was washed with brine, dried over MgSO$_4$ and evaporated to provide 144 mg of the title compound.

$^1$H NMR (CD$_3$COCD$_3$) δ7.42 (2H,d), 7.22 (1H, d), 7.17 (1H, d), 6.93 (2H, d), 6.7 (1H, dd), 5.33 (2H, s), 3.8 (3H, s), 2.42 (3H, s), 2.4 (2H, t), 1.9 (2H, t), 0.97 (2H, m), 0.8 (2H, m).

Step 11: Methyl-3-[1-(1-(4-Bromobenzyl)-5-methoxy-2-methyl-1H-indol-3-yl)cyclopropyl]propionate.

To a −5° C. solution of the nitrile from Step 10 (144 mg, 0.34 mmol mmol) in 10 mL MeOH was added dry HCl gas to give a saturated solution. The mixture was then heated to reflux overnight, cooled and poured into ice water. The mixture was adjusted to pH 9 with 2N NaOH and then extracted with ethyl acetate. The organic extracts were washed with brine, dried over MgSO$_4$ and evaporated to give 150 mg of the title compound.

$^1$H NMR (CD$_3$COCD$_3$) δ7.42 (2H,d), 7.15 (2H, m), 6.91 (2H, d), 6.7 (1H, dd), 5.32 (2H, s), 3.81 (3H, s), 3.5 (3H, s), 2.4 (3H, s), 2.33 (2H, m), 1.85 (2H, t), 0.85 (2H, m), 0.72 (2H, m).

Step 12: 3-[1-(1-(4-Bromobenzyl)-5-methoxy-2-methyl-1H-indol-3-yl) cyclopropyl]propionic acid.

To a solution of ester from Step 11 (150 mg, 0.33 mmol) in 5 mL MeOH was added 2N NaOH (0.5 mL, 1 mmol). The reaction mixture was heated to reflux for 3 h then cooled and partitioned between 1N HCl and ethyl acetate. The organic layer was washed with brine, dried over Na$_2$SO$_4$ and evaporated. The residue was filtered through a plug of silicic acid and the solid obtained was swished in (1: 1 ) Et$_2$O-hexane. Collection of the solid provided 110 mg of the title compound.

$^1$H NMR (CH$_3$COCH$_3$) δ7.43 (2H,d), 7.15 (2H, m), 6.92 (2H, d), 6.69 (1H, dd), 5.33 (2H, s), 3.8 (3H, s), 2.4 (3H, s), 2.32 (2H, t), 1.84 (2H, t), 0.85 (2H, m), 0.72 (2H, m).

EXAMPLE 2

[4-(1-(4-Bromobenzyl) -5-methoxy-2-methyl-1 H-indol-3-yl) -3-(ethane-1,2-diyl)]butanoic acid, sodium salt Step 1: [1-(3-Oxobut-1-en-1-yl)cyclopropyl]acetonitrile A mixture of the aldehyde from Example 1, Step 2 (8.12 g, 75 mmol) and 1-triphenylphosphoranylidene-2-propanone (26.4 g, 83 mmol) in 250 mL THF was heated to reflux overnight. The reaction mixture was partitioned between 1N HCl and ethyl acetate, and the organic layer was washed with brine, dried over MgSO$_4$ and evaporated. Et$_2$O was added to the residue, the phosphine oxide was filtered off and the solvent removed in vacuo. Purification through a plug of silica gel provided 10.3 g of the title compound.

$^1$H NMR (CD$_3$COCD$_3$) δ6.5 (1H, d), 6.15 (1H, d), 2.82 (2H, s), 2.19 (3H, s), 1.12 (4H, m).

Step 2: [1-(3-Oxobutan-1-yl)cyclopropyl]acetonitrile

A solution of the olefin from Step 1 (4.08 g, 26.8 mmol) in 85 mL ethyl acetate was treated with 30 psi hydrogen over 5% palladium on carbon (300 rag) in a Parr shaker for 1.5 h. The mixture was filtered through celite and evaporated to give 4.1 g of the title compound.

$^1$H NMR (CDCL3) δ2.57 (2H, t), 2.36 (3H, s), 2.18 (3H, s), 1.72 (2H, t), 0.53 (4H, m).

Step 3: [4-(1-(4-Bromobenzyl)-5-methoxy-2-methyl-1H-indol-3-yl]-3-(ethane-1,2-diyl)lbutanenitrile Acetic acid (3.03 mL, 53 mmol) was added to a 0° C. solution of the ketone from Step 2 (3.23 g, 21.3 mmol) and the hydrazine from Example 2, Step 5 (6.45 g, 21 mmol) in 100 mL toluene. The reaction mixture was stirred at r.t. for 1 h and then evaporated to dryness. The residue was dissolved in 100 mL dioxane, cooled to 0° C. and 4M HCl/dioxane (12.5 mL, 50 mmol) was added. The resulting mixture was stirred 1 h at r.t. followed by 1.5 h at 50° C. The cooled reaction mixture was partitioned between saturated NaHCO$_3$ and ethyl acetate. The organic layer was washed with brine, dried over MgSO$_4$ and evaporated. Purification by flash chromatography (20% ethyl acetate in hexane) provided 8.8 g of the title compound.

$^1$H NMR (CD$_3$COCD$_3$) δ7.42 (2H, d), 7.18 (1H, d), 7.1 (1H, d), 6.9 (2H, d), 6.7 (1H, dd), 5.38 (2H, s), 3.8 (3H, s), 2.97 (2H, s), 2.45 (2H, s), 2.32 (3H, s), 2.32 (3H, s), 0.6–0.5 (4H, m).

Step 4: Methyl [4-(1-(4-bromobenzyl)-5-methoxy-2-methyl-1H-indol-3-yl)-3-(ethane-1,2-diyl)]butanoate Dry HCl gas was added to 200 mL of MeOH at 0° C. to give a saturated solution. To this was added the nitrile from Step 3 (8.8 g, 20.8 mmol) dissolved in 50 mL MeOH and the resulting mixture stirred at r.t. for 16 h, then heated at reflux for 4 h. The reaction mixture was poured into ice water and extracted with ethyl acetate. The organic extracts were washed with saturated NaHCO$_3$ and brine, dried over MgSO$_4$ and evaporated. Purification by flash chromatography (15% ethyl acetate in hexane) provided 6.75 g of the title compound.

$^1$H NMR (CD$_3$COCD$_3$) δ7.44 (2H, d), 7.14 (1H, d), 7.1 (1H, d), 6.9 (2H, d), 6.69 (1H, dd), 5.37 (2H, s), 3.8 (3H, s), 3.6 (3H, s), 2.92 (2H, s), 2.28 (5H, s), 0.5–0.35 (4H, m).

Step 5: [4-(1-(4-Bromobenzyl)-5-methhoxy-2-methyl-1H-indol-3-yl)-3-(ethane-1,2-diyl)lbutanoic acid To the methyl ester from Step 4 (6.7 g, 14.7 mmol) in 75 mL MeOH was added 10 mL THF and 20 mL of 2N NaOH, and the mixture was stirred at r.t. for 2 days. The reaction mixture was concentrated in vacuo and the residue partitioned between 1N HCl and ethyl acetate. The organic layer was washed with brine, dried over Na$_2$SO$_4$ and evaporated. The solid residue was swished in Et$_2$-hexane (1:1) to give 4.5 g of the title compound.

$^1$H NMR (CD$_3$COCD$_3$) δ10.5 (1H, br), 7.42 (2H, d), 7.13 (3H, m), 6.9 (2H, d), 6.68 (1H, dd), 5.36 (2H, s), 3.8 (3H, s), 2.98 (2H, s), 2.28 (3H, s), 2.27 (2H, s), 0.5–0.37 (4H, m).

Step 6: [4-(1-(4-Bromobenzyl)-5-methoxy-2-methyl-1H-indol-3-yl)-3-(ethane-1,2-diyl)]butanoic acid, sodium salt The acid from Step 5 was treated with 1N NaOH (1.0 equivalent) and freeze dried to give the title compound.

EXAMPLE 3

4-(1-(4-Bromobenzyl)-5-methoxy-2-methyl-1H-indol-3-yl)-2-methylbutanoic acid

Step 1: Ethyl 4-(1-(4-bromobenzyl)-5-methoxy-2-methyl-1H-indol-3-yl)butanoate

A mixture of methyl 6-oxoheptanoate (3.1 g, 19.5 mmol), acetic acid (100 mL) and hydrazine from Example 1, Step 5 (5.0 g, 16.3 mmol) was heated at 100° C. overnight. The acetic acid was removed in vacuo and the residue was added to a 0° C. mixture of EtOH (150 mL) and acetyl chloride (5 mL). The resulting mixture was refluxed for 1 h, then most of the solvent was removed by distillation and further concentrated in vacuo. The residue was partitioned between ethyl acetate and saturated NaHCO$_3$, the organic layer washed with water, brine and dried over MgSO$_4$. Purification by flash chromatography (30% ethyl acetate in hexane) provided 4.68 g of the title compound.

$^1$H NMR (CDCl$_3$) δ7.35 (2H, d), 7.02 (1H, d), 7.0 (1H, s), 6.78 (2H, d), 6.72 (1H, dd), 5.18 (2H, s), 4.1 (2H, q), 3.84 (3H, s), 2.73 (2H, t), 2.31 (2H, t), 2.22 (3H, s), 1.93 (2H, m), 1.21 (3H, t).

Step 2: Ethyl 4-(1-(4-bromobenzyl)-5-methoxy-2-methyl-1H-indol-3-yl)-2-methylbutanoate n-BuLi (1.6M in hexane, 6.4 mL, 10.3 mmol) was added slowly to 2,2,6,6-tetramethylpiperidine at −10° C. and the slurry was stirred 30 min, then cooled to −78° C. and diluted with 25 mL degassed THF. This solution was transferred via cannula into a 50 mL (degassed) THF solution of ester from Step 1 (4.15 g, 9.3 mmol) at −78° C. After stirring 1 h, HMPA (1.6 mL, 9.3 mmol) was added and 30 min later CH$_3$I (5.8 mL, 93 mmol) was added. The reaction mixture was stirred 12 h at −78° C., then quenched with saturated NH$_4$Cl and extracted with Et$_2$O and ethyl acetate. The organic phase was washed with aqueous Na$_2$S$_2$O$_5$, water, brine and dried over MgSO$_4$. Purification by flash chromatography (15% ethyl acetate in hexane) provided 2.5 g of the title compound.

$^1$H NMR (CDCl$_3$) δ7.35 (2H, d), 7.0 (2H, m), 6.78 (2H, d), 6.73 (1H, dd), 5.17 (2H, s), 4.11 (2H, q), 3.85 (3H, s), 2.7 (2H, t), 2.48 (1H, m), 2.22 (3H, s), 2.0 (1H, m), 1.7 (1H, m), 1.25 (3H, t), 1.2 (3H, d).

Step 3: 4-(1-(4-Bromobenzyl)-5-methoxy-2-methyl-1H-indol-3-yl)-2-methylbutanoic acid The ester from Step 2 was hydrolysed as described in Example 1, Step 12 to give the title compound.

$^1$H NMR (CD$_3$COCD$_3$) δ7.42 (2H, d), 7.15 (1H, d), 7.08 (1H, d), 6.9 (2H, d), 6.68 (1H, dd), 5.33 (2H, s), 3.8 (3H, s), 2.78 (2H, t), 2.5 (1H, m), 2.31 (3H, s), 2.0 (1H, m), 1.7 (1H, m), 1.2 (3H, d).

EXAMPLE 4

4-(1-(4-Bromobenzyl)-5-methoxy-2-methyl-1H-indol-3-yl)butanoic acid

The ester from Example 3, Step 1 was hydrolysed as described in Example 1, Step 12 to give the title compound.

$^1$H NMR (CD$_3$COCD$_3$) d 7.42 (2H, d), 7.32 (1H, s), 7.12 (1H, d), 6.9 (2H, d), 6.86 (1H, d), 5.36 (2H, s), 2.8 (2H, t), 2.33 (2H, t), 2.3 (3H, s), 1.9 (2H, m).

EXAMPLE 5

4-(1-(4-Bromobenzyl)-5-methoxy-2-methyl-1H-indol-3-yl)-2,2-dimethylbutanoic acid, sodium salt Step 1: Ethyl 4-(1-(4-bromobenzyl)-5-methoxy-2-methyl-1H-indol-3-yl)-2,2-dimethylbutanoate The ester from Example 3, Step 2 was treated as described in Example 3, Step 2 to give the title compound.

$^1$H NMR (CDCl$_3$) δ7.35 (2H, d), 7.0 (2H, m), 6.8 (2H, d), 6.73 (1H, dd), 5.17 (2H, s), 4.12 (2H, q), 3.85 (3H, s), 2.61 (2H, m), 2.22 (3H, s), 1.8 (2H, m), 1.27 (6H, s).

Step 2: 4-(1-(4-Bromobenzyl)-5-methoxy-2-methyl-1H-indol-3-yl)-2,2-dimethylbutanoic acid The ester from Step 1 was hydrolysed as described for Example 1, Step 12 to give the title compound.

$^1$H NMR (CD$_3$COCD$_3$) δ7.42 (2H, d), 7.13 (1H, d), 7.08 (1H, d), 6.91 (2H, d), 6.69 (1H, dd), 5.35 (2H, s), 3.8 (3H, s), 2.7 (2H, m), 2.3 (3H, s), 1.8 (2H, m), 1.3 (6H, s).

Step 3: 4-(1-(4-Bromobenzyl)-5-methoxy-2-methyl-1H-indol-3-yl)-2,2-dimethylbutanoic acid, sodium salt Using the method of Example 2, Step 6, the title compound was obtained.

EXAMPLE 6

4-(1-(4-Bromobenzyl)-5-methoxy-2-methyl-1 H-indol-3-yl) -2-hydroxy-2-methylbutanoic acid Step 1: Ethyl 4-(1-(4-bromobenzyl)-5-methoxy-2-methyl-1H-indol-3-yl )-2-hydroxy-2-methylbutanoate n-BuLi (1.6M in hexane, 1.5 mL, 2.4 mmol) was slowly added to 2,2,6,6-tetramethylpiperidine at 0° C. and the slurry was stirred 10 min, then cooled to −78° C. and diluted with 6 mL (oxygenated) THF. The ester from Example 3, Step 2 (880 mg, 1.92 mmol) dissolved in 3 mL THF (O$_2$) was added and the resulting mixture was stirred 1 h at −78° C. and 1 h at −45° C. HMPA (668 μL, 3.8 mmol) was added and the mixture was stirred another 2 h at −30° C., then warmed to 0° C. The reaction was quenched with aq. NaHSO$_3$ and then partitioned between saturated NH$_4$Cl and ethyl acetate; the organic layer was washed with water, brine and dried over MgSO$_4$. Purification by flash chromatography (40% ethyl acetate in hexane) provided 230 mg of the title compound.

$^1$H NMR (CDCl$_3$) δ7.35 (2H, d), 7.0 (2H, m), 6.80 (2H, d), 6.73 (1H, dd), 5.15 (2H, s), 4.12 (1H, m), 3.95 (1H, m), 3.85 (3H, s), 3.32 (1H, br), 2.87 (1H, m), 2.6 (1H, m), 2.22 (3H, s), 2.18 (1H, m), 1.9 (1H, m), 1.42 (3H, s), 1.2 (3H, t).

Step 2: 4-(1-(4-Bromobenzyl)-5-methoxy-2-methyl-1H-indol-3-yl)-2-hydroxy-2-methylbutanoic acid Using the method of Example 1, Step 12, the ester from Step 1 (220 mg, 0.46 mmol) was hydrolysed to give 145 mg of the title compound.

$^1$H NMR (CD$_3$COCD$_3$) δ7.46 (2H, d), 7.17 (1H, d), 7.04 (1H, s), 6.93 (2H, d), 6.7 (1H, d), 5.34 (2H, s), 4.3 (1H, br), 3.8 (3H, s), 2.93 (1H, m), 2.61 (1H, m), 2.3 (3H, s), 2.1 (1H, dr), 1.88 (1H, dr), 1.47 (3H, s).

EXAMPLES 7 AND 8

(3S) and (3R) 4-(1-(4-Bromobenzyl)-5-methoxy-2-methyl-1H-indol-3-yl)-3-methylbutanoic acid Step 1: Methyl (5-methoxy-2-methyl-1H-indol-3-yl)acetate A suspension of 4-methoxyphenyl hydrazine hydrochloride (50 g, 0.286M) and methyl 4-oxo-pentanoate (40 mL, 0.315M) in HOAc (500 mL) was stirred for 16 h at reflux. The solvent was removed under vacuum, and the brown residue was partitioned between EtOAc and saturated NaHCO$_3$ solution. The organic layer was washed with H$_2$O and brine, and was then dried (MgSO$_4$) and filtered. Following removal of the solvent, the crude product was purified by flash chromatography (1:20 EtOAc/toluene), to give 48 g of the title compound as a pale brown syrup.

$^1$H NMR (CD$_3$COCD$_3$) δ7.14–7.20 (1H, m), 6.98–7.01 (1H, m), 6.65–6.71 (1H, m), 3.79 (3H, s), 3.66 (2H, s), 3.62 (3H, s), 2.39 (3H, s).

Step 2: Methyl (1-(4-bromobenzyl)-5-methoxy-2-methyl-1H-indol-3-yl)acetate

To a solution of ester from Step 1 (13.8 g, 59 mmol) in THF (300 mL) and DMPU (40 mL) at −78° C. was added KHMDS solution (0.64M/toluene, 95 mL, 60 mmol). The reaction mixture was warmed to 0° C. and was then recooled to −78° C., at which point a solution of 4-bromobenzyl bromide (17.0 g, 68 mmol) in THF (80 mL) was added via double-tipped needle. The reaction was allowed to warm to r.t., and was then poured into 1M HCl (500 mL). The product was extracted with Et$_2$O and the organic phase was washed with H$_2$O and brine. After drying (MgSO$_4$), filtration, and removal of solvent, the crude product was purified by flash chromatography (1:20 EtOAc/toluene). The resulting prodeuct was recrystallized from CH2Cl$_2$/hexane to give 11.4 g of the title compound.

¹H NMR (CD₃COCD₃) δ7.42–7.48 (2H, m), 7.15–7.21 (1H, m), 7.04–7.07 (1H, m), 6.90–6.96 (2H, m), 6.66–6.73 (1H, m), 5.37 (2H, s), 3.81 (3H, s), 3.70 (2H, s), 3.62 (3H, s), 2.30 (3H, s).

Step 3: (1-(4-Bromobenzyl)-5-methoxy-2-methyl-1H-indol-3-yl) acetaldehyde

To a solution of ester from Step 2 (16.0 g, 39.8 mmol) in CH₂Cl₂ (320 mL) at –100° C. was added slowly a solution of DIBAH (1.5M/toluene, 32 mL, 47.7 mmol). The reaction was then stirred for 1_h at –78° C., before being quenched by the addition of MeOH (3 mL), followed by 25% w/v tartaric acid (100 mL). After stirring overnight at r.t., the product was extracted with CH2Cl₂. The organic layer was dried (MgSO₄), filtered, and evaporated to give a pale green syrup. This was stirred vigorously with 1:4 Et₂O/hexane to give 13 g of the title compound as an off-white solid.

¹H NMR (CD₃COCD₃) δ9.609.63 (1H, m), 7.45–7.50 (2H, m), 7.21–7.25 (1H, m), 7.04–7.06 (1H, m), 6.95–7.00 (2H, m), 6.72–6.77 (1H, m), 5.41 (2H, s), 3.77–3.82 (5H, m), 2.35 (3H, s).

Step 4: Ethyl 4-(1-(4-bromobenzyl)-5-methoxy-2-methyl-1H-indol-3-yl)-2(E)-butenoate To a solution of aldehyde from Step 3 (4.3 g, 11.5 mmol) in toluene (75 mL) was added ethyl (triphenylphosphoranylidene)acetate (6.0 g, 17.3 mmol). The mixture was stirred at 80° C. overnight, and was then filtered through a plug of silica gel. Concentration of the filtrate gave a yellow residue which was purified by flash chromatography (1:9 EtOAc/toluene) to give 4.7 g of an off-white solid.

¹H NMR (CD₃COCD₃) δ7.44–7.48 (2H, m), 7.19–7.23 (1H, m), 7.07–7.12 (1H, m), 7.03–7.07 (1H, m), 6.92–6.98 (2H, m), 6.71–6.76 (1H, m), 5.75–5.81 (1H, m), 5.39 (2H, s), 4.06–4.14 (2H, m), 3.80 (3H, s), 3.65–3.69 (2H, m), 2.31 (3H, s), 1.18–1.23 (3H, m).

Step 5: Ethyl 4-(1-(4-bromobenzyl)-5-methoxy-2-methyl-1H-indol-3-yl)-3-methylbutanoate To a suspension of CuI (7.2 g, 38 mmol) in dry Et₂O (10 mL) at 0° C. was added slowly a solution of MeLi (1.4M/Et₂O, 54 mL, 76 mmol). The pale beige solution was cooled to –78° C. and TMSCl (4.8 mL, 38 mmol) was added. To the resulting mixture was added, via double-tipped needle, a solution of a,b-unsaturated ester from Step 4 (4.2 g, 9.5 mmol) in Et₂O/THF (5 mL/2 mL). The reaction mixture was allowed to warm slowly to r.t. overnight, and was then quenched with saturated NH₄Cl. Following EtOAc/H₂O work-up, the crude material was purified by flash chromatograpohy (1:20 EtOAc/hexane followed by 1:10 EtOAc/hexane) to give 4.0 g of the title compound as a white solid.

¹H NMR (CD₃COCD₃) δ7.43–7.48 (2H, m), 7.15–7.19 (1H, m), 7.09–7.12 (1H, m), 6.90–6.95 (2H, m), 6.68–6.73 (1H, m), 5.37 (2H, s), 4.04–4.10 (2H, m), 3.81 (3H, s), 2.73–2.81 (1H, m), 2.47–2.54 (1H, m), 2.31 (3H, s), 2.29–2.40 1H, m), 2.19–2.27 (1H, m), 1.17–1.24 (3H, m), 0.95–1.00 (3H, m).

Step 6: 4-(1-(4-Bromobenzyl)-5-methoxy-2-methyl-1H-indol-3-yl)-3-methylbutanoic acid To a solution of ester from Step 5 (3.5 g, 7.6 mmol) in MeOH/THF (50 mL/35 mL) was added 1M NaOH (22.9 mL, 22.9 mmol). After heating at reflux for 2 h, the mixture was concentrated under vacuum and the residue was partitioned between EtOAc/H₂O containing HOAc (3 mL). The organic layer was washed with H₂O, brine, and was then dried (MgSO₄), filtered, and evaporated. The resulting solid was stirred vigorously with 1:10 EtOAc/hexane for 2 h to give, after filtration, 2.81 g of white solid.

¹H NMR (CD₃COCD₃) δ7.43–7.48 (2H, m), 7.12–7.18 (2H, m), 6.90–6.95 (2H, m), 6.68–6.72 (1H, m), 5.38 (2H, s), 3.80 (3H, s), 2.78–2.85 (1H, m), 2.57–2.63 (1H, m), 2.33–2.41 (1H, m), 2.31 (1H, m), 2.20–2.26 (1H, m), 0.97–1.01 (3H, m).

Step 7: (4R)-N-[4-(1-(4-Bromobenzyl)-5-methoxy-2-methyl-1H-indol-3-yl)-3-methylbutanoyl]-4-isopropyl-2-oxazolidinone To a solution of acid from Step 6 (1.0 g, 2.3 mmol) in THF (20 mL) at 0° C. was added KHMDS (0.64M/toluene, 4.0 mL, 2.6 mmol) followed by pivaloyl chloride (0.31 mL, 2.6 mmol). After 30 rain at 0° C., the solution was cooled to –78° C., and a cloudy solution of (R)-4-isopropyl oxazolidinone (0.35 g, 2.7 mmol) and BuLi (1.6M/hexane, 1.7 mL, 2.7 mmol) in THF (20 mL) was added via double-tipped needle. After 10 min at –78° C., the reaction was warmed to 0° C. for 1 h, at which point it was quenched by the addition of saturated NH₄Cl solution. Following EtOAc/H₂O work-up, the two diastereomers were obtained by flash chromatography (1:5 EtOAc/hexane). isomer A=0.55 g, isomer B =0.52 g.

Isomer A

¹H NMR (CD₃COCD₃) δ7.43–7.47 (2H, m), 7.13–7.17 (2H, m), 6.92–6.97 (2H, m), 6.66–6.71 (1H, m), 5.37 (2H, s), 4.30–4.38 (1H, m), 4.25–4.30 (2H, m), 3.82 (3H, s), 3.00–3.07 (1H, m), 2.75–2.84 (2H, m), 2.60–2.67 (1H, m), 2.39–2.49 (1H, m), 2.33 (3H, s), 2.27–2.86 (1H, m), 0.99–1.03 (3H, m), 0.89–0.94 (3H, m), 0.84–0.89 (3H, m).

Isomer B

¹H NMR (CD₃COCD₃) δ7.43–7.47 (2H, m), 7.13–7.17 (2H, m), 6.92–6.97 (2H, m), 6.66–6.71 (1H, m), 5.37 (2H, s), 4.28–4.37 (2H, m), 3.82 (3H, s), 3.13–3.21 (1H, m), 2.81–2.88 (1H, m), 2.57–2.71 (2H, m), 2.41–2.51 (1H, m), 2.33 (3H, s), 2.26–2.35 (1H, m), 0.94–0.98 (3H, m), 0.90–0.94 (3H, m), 0.82–0.85 (3H, m).

Step 8: (3S) 4-(1-(4-Bromobenzyl)-5-methoxy-2-methyl-1H-indol-3-yl)-3-methylbutanoic acid To the oxazolidinone from Step 7, isomer A (295 mg, 0.54 mmol) in THF (10 mL) at –10° C. was added 30% H₂O₂ (0.5 mL) followed by 1M aqueous LiOH (3 mL). The mixture was stirred at 0° C. for 45 min, and was then cooled to –10° C. to be quenched by careful addition of 1M aqueous Na₂S₂O₅ (10 mL). The mixture was acidified (6M HCl, 1 mL) and the product was extracted with EtOAc. The organic layer was washed with H₂O and brine, and was then dried (MgSO₄), and filtered. After removal of the solvent, the crude product was purified by flash chromatography (1:5 EtOAc/hexane followed by 1:2 EtOAc/hexane). The resulting off-white solid was stirred vigorously with 1:10 EtOAc/hexane for 2 h to give, after filtration, 188 mg of the title compound. $[\alpha]_D=+4.6°$ (c=1, acetone)

(3R) 4-(1-(4-Bromobenzyl)-5-methoxy-2-methyl-1H-indol-3-yl)-3-methylbutanoic acid In the same manner as for isomer A, the (R,R) diatereomer (isomer B) from Step 7 (0.64 g, 1.18 mmol), was cleaved to give 0.25 g of the acid. $[\alpha]_D=-7.1°$ (c=1, acetone).

¹H NMR (CD₃COCD₃) δ7.43–7.48 (2H, m), 7.13–7.19 (2H, m), 6.90–6.95 (2H, m), 6.67–6.72 (1H, m), 5.38 (2H, s), 3.80 (3H, s), 2.78–2.85 (1H, m), 2.56–2.64 (1H, m), 2.32 (3H, s), 2.28–2.42 (2H, m), 2.19–2.26 (1H, m), 0.96–1.01 (3H, m).

EXAMPLE 9

[5-Methoxy-2-methyl-1-(4-methylthiobenzyl)indol-3-yl]-3-methylbutanoic acid

Step 1: Methyl (5-methoxy-2-methyl-1-(4-methylthiobenzyl)indol-3-yl]acetate

To the indole of Example 7, Step 1, (1.00 g, 4.29 mmol) in DMF (15.0 mL) at 0° C. were added NaH 60% in oil (188 mg, 4.72 mmol) and a solution of 4-chloromethylthioanisole (810 mg, 4.7 mmol) in DMF (5.0 mL). After a period of 5 min at r.t., the reaction was quenched by the addition of 25% aqueous solution of NH₄OAc. The reaction was extracted with EtOAc, dried over Na₂SO₄, evaporated in vacuo and purified by flash chromatography (20% EtOAc in hexane) to provide the title compound (770 mg).

¹H NMR (CD₃COCD₃) δ7.20 (3H, m), 7.05 (1H, d), 6.95 (2H, d), 6.70 (1H, dd), 5.40 (2H, s), 3.80 (3H, s), 3.70 (2H, s), 3.60 (3H, s), 2.45 (3H, s), 2.30 (3H, s).

Step 2: 4-[1-(4-Bromobenzyl)-5-methoxy-2-methyl-1-(4-methylthiobenzyl)-3-yl]acetaldehyde To the ester of Step 1 (770 mg, 1.73 mmol), dissolved in CH₂Cl₂ (20.0 mL) at −100° C. was added a solution of DIBAH (1.6 mL, 2.2 mmol) in toluene. After a period of 2 h at −78° C., an excess of MeOH was added followed by a 1M solution of tartaric acid. The resulting mixture was extracted with EtOAc, dried over Na₂SO₄, evaporated in vacuo and purified by flash chromatography (25% EtOAc in hexane) to provide the desired aldehyde (400 mg).

¹H NMR (CD₃COCD₃) δ9.60 (1H, t), 7.25 (1H, d), 7.15 (2H, d), 7.05 (1H, d), 6.95 (2H, d), 6.70 (1H, dd), 5.40 (2H, s), 3.82 (3H, s), 3.80 (2H, d), 2.50 (2H, s), 2.30 (3H, s).

Step 3: Ethyl 4-[5-methoxy-2-methyl-1-(4-methylthiobenzyl)indol-3-yl]-2-butenoate To the aldehyde of Step 2 (440 mg, 1.02 mmol) in toluene (15.0 mL) was added (carbethoxymethylene)triphenylphosphorane (711 mg, 2.04 mmol). After a period of 1 h at 100° C., the reaction was poured in 25% aqueous solution of NH₄OAc, extracted with EtOAc, purified by flash chromatography (25% EtOAc in hexane) to give the title product (376 mg).

¹H NMR (CD₃COCD₃) a 7.10 to 7.30 (5H, m), 7.05 (1H, m), 6.95 (2H, d), 6.70 (1H, dd), 5.8 (1H, d), 5.40 (2H, s), 4.10 (2H, q), 3.80 (3H, s), 3.70 (2H, m), 2.45 (3H, s), 2.30 (3H, s), 1.20 (3H, t).

Step 4: Ethyl 4-[5-methhoxy-2-methyl-1-(4-methhylthiobenzyl)indol-3-yl]-3-methylbutanoate To a suspension of CuI (875 mg, 4.59 mmol) in ether (36.0 mL) at 0° C. was added a 1.4M solution of MeLi in ether (6.56 mL, 9.18 mmol). To the resulting mixture at −78° C. were added TMSCl (579 mL, 4.54 mmol) and a Et₂O/THF solution (60 mL/12.0 mL) of the olefin (376 mg) of Step 3. After a period of 2 h at r.t., the reaction was quenched by the addition of 25% aqueous solution of NH₄OAc, extracted with EtOAc, dried over Na₂SO₄, evaporated in vacuo and purified by flash chromatography (25 % EtOAc in hexane) to afford the title compound (230 mg).

¹H NMR (CD₃COCD₃) δ7.15 (3H, 2d), 7.10 (1H, d), 6.90 (2H, d), 6.65 (1H, dd), 5.40 (2H, s), 3.80 (3H, s), 2.80 (1H, m), 2.60 (1H, m), 2.25 (3H, s), 2.20 to 2.30 (3H, m), 1.20 (3H, t), 0.90 (3H, d).

Step 5: 4-[5-Methoxy-2-methyl-1-(4-methylthiobenzyl)indol-3-yl]-3-methylbutanoic acid The ester from Step 4 was hydrolysed as described in Example 7, Step 6, to give the desired acid.

¹H NMR (CD₃COCD₃) δ7.15 (5H, m), 6.90 (2H, d), 6.70 (1H, d), 5.40 (2H, s), 2.80 (1H, m), 2.60 (1H, m), 2.45 (3H, s), 2.30 (3H, s), 2.25 to 2.40 (2H, m), 2.20 (1H, m), 0.95 (3H, d).

EXAMPLE 10 trans-2-[(1-(4-Bromobenzyl)-5-methoxy-2-methyl-1H-indol-3-yl)methyl]cyclopropanecarboxylic acid Step 1: Ethyl trans-2[(1-(4-bromobenzyl)-5-methoxy-2-methyl-1H-indol-3-yl)methyl]cyclopropanecarboxylate To the olefinic ester from Example 7, Step 4 (200 mg, 0.45 mmol) in 5 mL Et₂O was added a catalytic amount of palladium acetate and excess diazomethane/Et₂O solution.

The mixture was stirred 5 min at 0° C. and then evaporated. The title compound was purified by flash chromatography (15% EtOAc in hexanes) (40 mg).

Step 2: trans-2-[(2-(4-Bromobenzyl)-5-methoxy-2-methyl-1H-indol-3-yl)methyl]cyclopropanecarboxylic acid The ester from Step 1 (40 mg, 0.09 mmol), was dissolved in THF (1 mL)—MeOH (1 mL) and 1N NaOH (1 mL) was added. The reaction mixture was stirred at room temperature for 18 h, and then EtOAc and dilute HCl were added. The organic phase was separated, dried over Na₂SO₄, filtered and evaporated. The residue was purified by flash chromatography over silicic acid (20% EtOAc in hexanes) to give the title compound (35 mg).

¹H NMR (CD₃COCD₃) δ7.45 (2H, d), 7.20 (2H, d), 7.10 (1H, d), 6.92 (2H, d), 6.70 (1H, dd), 5.40 (2H, s), 3.80 (3H, s), 2.90 (2H, m), 1.60 (1H, m), 1.50 (1H, m), 1.05 (1H, m), 0.90 (1H, m).

EXAMPLE 11

(2R,3S)-[(4-Bromobenzyl)-5-methoxy-2-methyl-1H-indol-3-yl]-2,3-dimethylbutanoic acid Step 1: N-[4-(1-(4-Bromobenzyl)-5-methoxy-2-methyl-1H-indol-3-yl)-2(R),3(S)-dimethylbutanoyl]-4(R)-isopropyl-2-oxazolidinone To the imide of Example 7, Step 7, isomer A (200 mg, 0.369 mmol) dissolved in THF (2.0 mL) at −78° C. was added a solution of KHMDS (0.5 mL) in toluene (1.10 mL, 0,660 mmol). The temperature was then increased slowly to −40° C. To the mixture recooled at −78° C. was added MeI (100 mL). The temperature was allowed to warm slowly to −40° and the reaction was quenched by the addition of 25% aqueous solution of NH₄OAc. The mixture was extracted with EtOAc, dried over Na₂SO₄, evaporated in vacuo and purified by flash chromatography (20% EtOAc in hexane) to afford the title product (100 mg).

¹H NMR (CD₃COCD₃) δ7.45 (2H, dd), 7.15 (1H, d), 7.10 (1H, d), 6.90 (2H, d), 6.65 (1H, dd), 5.30 (2H, s), 4.35 (1H, m), 4.25 (2H, m), 3.85 (1H, quintet), 3.80 (3H, s), 2.80 (1H, dd), 2.50 (1H, m), 2.35 (1H, m), 2.30 (3H, s), 1.20 (3H, d), 0.80 to 0.90 (9H, 3d).

Step 2: (2R,3S)-[1-(4-Bromobenzyl)-5-methoxy-2-methyl-1H-indol-3-yl]-2,3-dimethylbutanoic acid To the imide of Step 1 (130 mg, 0234 mmol) dissolved in THF (4.29 mL) at −10° C. were added H₂O₂ 30% (2.14 mL) and a 1M solution of LiOH (1.3 mL). The resulting mixture was stirred at +5° C. for 8 h and excess of aqueous sodium metabisulfite was added at −10° C. A saturated aqueous solution of NH₄Cl was then added, the mixture extracted with EtOAC, dried over Na₂SO₄, evaporated in vacuo and purified by flash chromatography over silic acid (20% EtOAc in hexane) to afford the title product 73 mg).

¹H NMR (CD₃COCD₃) δ7.40 (2H, d), 7.20 (2H, d), 7.10 (1H, d), 6.90 (2H, d), 6.70 (1H, dd), 5.40 (2H, s), 3.78 (3H, s), 2.90 (1H, dd), 2.38 to 2.60 (2H, m), 2.30 (3H, s), 2.25 (1H, m), 1.20 (3H, d), 0.85 (3H, d).

EXAMPLE 12

(2R,3R)-[1-(4-Bromobenzyl)-5-methoxy-2-methyl-1H-indol-3-yl]-2,3dimethylbutanoic acid.

Step 1: N-[4-(1-(4-Bromobenzyl)-5-methoxy-2-methyl-1H-indol-3-yl)-2(R),3(R)-dimethylbutanoyl]-4(R)-isopropyl-2-oxazolidinone As described for Example 11, Step 1, but starting with isomer B of Example 7, Step 7, 250 mg, provide 150 mg of the title compound.

¹H NMR (CD₃COCD₃) δ7.50 (2H, d), 7.15 (1H, d), 7.00 (1H, dd), 6.90 (1H, d), 6.70 (1H, dd), 5.40 (2H, s), 4.25 (1H, m), 4.15 (1H, d), 3.75 (1H, m), 3.75 (3H, s), 2.95 (1H, dd), 2.40 (1H, m), 2.30 (1H, m), 2.25 (3H, s), 0.70 to 0.95 (9H, 3s).

Step 2: (2R,3R)-[1-(4-Bromobenzyl)-5-methoxy-2-methyl-1H-indol-3-yl]-2,3-dimethylbutanoic acid As described for Example 11, Step 2, the imide from Step 1 (200 mg) provided the title compound (100 mg).

¹H NMR (CD₃COCD₃) δ7.45 (2H, d), 7.20 (1H, d), 7.10 (1H, d), 6.90 (2H, d), 6.60 (1H, dd), 5.40 (2H, s), 3.75 (3H, s), 2.90 (1H, dd), 2.50 (2H m), 2.30 (3H, s), 2.20 (1H, m), 1.25 (3H, d), 0.90 (3H, d).

EXAMPLE 13

(2S,3R)-[1-(4-Bromobenzyl)-5-methoxy-2-methyl-1H-indol-3-yl]-2,3-dimethylbutanoic acid Step 1: N-[4-(1-(4-Bromobenzyl)-5-methoxy-2-methyl-1H-indol-3-yl)-2(S),3(R)-dimethylbutanoyl]-4(S)-isopropyl-2-oxazolidinone As described for Example 11, Step 1, but starting with the enantiomer of isomer A from Example 7, Step 7 250 mg provided 130 mg of the title compound.

¹H NMR (CD₃COCD₃) δ7.45 (2H, d), 7.13 (1H, d), 7.10 (1H, d), 6.95 (2H, d), 6.55 (1H, dd), 5.35 (2H, s), 4.35 (1H, m), 4.25 (2H, m), 3.85 (1H, quintet), 3.80 (3H, s), 2.75 (1H, dd), 2.50 (1H, m), 2.30 (1H, m), 2.25 (3H, s), 1.15 (3H, d), 0.75 to 0.90 (9H, 3d).

Step 2: (2R,3R)-[1-(4-Bromobenzyl)-5-methhoxy-2-methyl-1H-indol-3-yl]-2,3-dimethylbutanoic acid As described for Example 11, Step 2, the imide from Step 1 (130 mg) provided the title compound (90 mg).

¹H NMR (CD₃COCD₃) δ7.40 (2H, d), 7.15 (1H, d), 7.05 (1H, d), 6.90 (2H, d), 6.7 (1H, dd), 5.30 (2H, s), 3.70 (3H, s), 2.85 (2H, dd), 2.45 (2H, m), 2.30 (3H, s), 2.20 (1H, m), 1.20 (3H, d), 0.95 (3H, d).

EXAMPLE 14

(2S,3S)-[1-(4-Bromobenzyl)-5-methoxy-2-methyl-1H-indol-3-yl]-2,3-dimethylbutanoic acid Step 1: N-[4-(1-(4-Bromobenzyl)-5-methoxy-2-methyl-1H-indol-3-yl)-2(S),3(S)-dimethylbutanoyl]-4(S)-isopropyl-2-oxazolidinone As described for Example 11, Step 1, but starting with the enantiomer of isomer B, Example 7, Step 7 250 mg provided 140 mg of the title compound.

¹H NMR (CD₃COCD₃) δ7.45 (2H, d), 7.20 (1H, d), 7.05 (1H, d), 6.95 (2H, d), 6.65 (1H, dd), 5.20 (2H, s), 4.25 (2H, m), 4.10 (1H, d), 3.81 (1H, m), 3.80 (3H, s), 3.00 (1H, dd), 2.45 (1H, m), 2.30 (1H, m), 2.30 (3H, s), 1.30 (3H, d), 0.80 to 1.00 (9H, 3d).

Step 2: (2S,3S)-[1-(4-Bromobenzyl)-5-methoxy-2-methyl-1H-indol-3-yl]-2,3-dimethylbutanoic acid As described for Example 11, Step 2, the imide from Step 1 (130 mg) provided (80 mg) the title compound.

¹H NMR (CD₃COCD₃) δ7.45 (2H, d), 7.15 (1H, d), 7.10 (1H, d), 6.90 (2H, d), 6.70 (1H, dd), 5.35 (2H, s), 3.75 (3H, s), 2.90 (1H, dd), 2.50 (2H, m), 2.20 (1H, m), 1.20 (3H, d), 0.90 (3H, d)

EXAMPLE 15

4-(1-(4-Bromobenzyl)-5-methoxy-2-methyl-1H-indol-3-yl)-2-methylpentanoic acid

Step 1: Ethyl 2-(1-(4-bromobenzyl)-5-methoxy-2-methyl-1H-indol-3-yl)acetate

To the ethyl ester from Example 7, Step 1 (2.00 g, 8.10 mmol) dissolved in THF (40.0 mL) was added at −78° C. a 0.5M solution of KHMDS (16.0 mL, 8.10 mmol) in toluene and HMPA (200 μL). After a period of 10 min, 4-bromobenzyl bromide was added to the resulting mixture. The reaction mixture was brought to room temperature, quenched by the addition of 25% aqueous NH₄OAc solution, extracted with EtOAc, dried over Na₂SO₄ and evaporated in vacuo. The title product was purified by flash chromotography (15% to 20% EtOAc in hexane) (1.5 g).

¹H NMR (CD₃COCD₃) 7.45 (2H, d), 7.20 (1H, d), 7.10 (1H, d), 6.95 (2H, d), 6.65 (1H, dd), 5.40 (2H, s), 4.05 (2H, q), 3.75 (3H, s), 3.60 (2H, s), 2.30 (3H, s), 1.20 (3H, t).

Step 2: Ethyl 2-(1-1(4-bromobenzyl)-5-methoxy-2-methyl-1H-indol-3-yl)propanoate

To the ester (1.0 g, 2.40 mmol) of step 1 dissolved in THF (14.0 mL) at −78° C. was added DMPU (1.3 mL) and a 0.5M KHMDS solution in toluene (5.3 mL, 2.64 mmol). After a period of 0.5 h at −78° C., was added an excess of MeI (200 μL). The resulting mixture was stirred at room temperature for 0.5 h, quenched by the addition of a 25% aqueous NH₄OAc solution, extracted with EtOAc, dried over Na₂SO₄ and evaporated in vacuo. The desired alkylated product was obtained after purification by flash chromatography (20% EtOAc in hexane) (600 mg).

¹H NMR (CD₃COCD₃) δ7.50 (2H, d), 7.20 (1H, d), 7.15 (1H, d), 6.90 (2H, d), 6.70 (1H, dd), 5.40 (2H, s), 4.05 (3H, m), 3.80 (3H, s), 2.30 (3H, s), 1.50 (3H, d), 1.15 (3H, t).

Step 3: Methyl 4-(1-(4-bromobenzyl)-5-methoxy-2-methyl-1H-indol-3-yl)-2-pentenoate To the ester (600 mg, 1.34 mmol) of Step 2 dissolved in CH₂Cl₂ (6.9 mL) at −100° C. was added a 1.5M DIBAH solution (1.20 mL, 1.81 mmol). After a period of 1 h at −78° C., the reaction was quenched by the addition of an excess of MeOH followed by tartaric acid solution. The mixture was stirred for 1 h and extracted with EtOAc. After the usual procedure the corresponding aldehyde was purified by flash chromatography (20% EtOAc in hexane) (500 mg).

To this aldehyde (1.0 g, 2.54 mmol) in toluene was added the methyl (triphenylphosphoranylidene) acetate (1.80 g, 5.17 mmol). The resulting mixture was heated at 80° C. for 2 h and passed through a pad of silica gel (70% EtOAc in hexane) to provide the title compound (1.00 g).

¹H NMR (CD₃COCD₃) δ7.50 (2H, d), 7.30 (1H, dd), 7.20 (1H, d), 7.05 (1H, d), 6.90 (2H, d), 6.70 (1H, dd), 5.90 (1H, dd), 5.40 (2H, s), 4.00 (1H, m), 3.80 (3H, s), 3.70 (3H, s), 2.30 (3H, s), 1.50 (3H, d).

Step 4: Methyl 4-(1-(4-bromobenzyl)-5-methoxy-2-methyl-1H-indol-3-yl)pentanoate

To the ester (520 mg, 1.17 mmol) of Step 3 dissolved in a THF/MeOH mixture (4.0 mL/20.0 mL) was added an excess of Mg and a few drops of 1,2-dibromoethane. The reduction was initated by heating at reflux. After standing for a few hours at room temperature, the reaction mixture was quenched by the addition of a 25% aqueous NH₄OAc solution, extracted with EtOAc, dried over MgSO₄ and evaporated in vacuo. The desired reduced product was purified by flash chromatography (25% EtOAc in hexane) to provide 170 mg of an oil.

¹H NMR (CD₃COCD₃) δ7.45 (2H, d), 7.20 (1H, d), 7.15 (1H, d), 6.90 (2H, d), 6.70 (1H, dd), 5.40 (2H, s), 3.80 (3H, s), 3.50 (3H, s), 3.10 (1H, m), 2.30 (3H, s), 2.10–2.20 (4H, m), 1.40 (3H, d).

Step 5: 4-(1-(4-Bromobenzyl)-5-methoxy-2-methyl-1H-indol-3-yl)pentanoic acid

The ester of Step 4 (170 mg) was hydrolysed as described in Example 7, Step 6.

$^1$H NMR (CD$_3$COCD$_3$) δ7.40 (2H, d), 7.20 (1H, d), 7.10 (1H, d), 7.00 (2H, d), 6.75 (1H, dd), 5.30 (2H, s), 3.85 (3H, s), 3.10 (1H, m), 2.30 (3H, s), 2.10–2.20 (4H, m), 1.40 (3H, d).

Step 6: N-[4-(1-(4-Bromobenzyl)-5-methoxy-2-methyl-1H-indol-3-yl)]pentanoyl-2-oxazolidinone To the acid (160 mg, 0.372 mmol) of Step 5 dissolved in THF (3.0 mL) at 0° C. was added a 0.5M KHMDS/toluene solution (820 mL, 0.410 mmol) followed by pivaloyl chloride (51 μL, 0.41 mmol). In a separate flask, a lithium salt solution of 2-oxazolidinone was prepared by the addition at −78° C. of n BuLi (1.6M, 268 μL, 0.431 mmol) to a THF solution (3.0 mL) of 2-oxazolidinone (40 mg, 0.43 mmol). This solution was cannulated to the previous mixture at −78° C. After a period of 1 h at 0° C., the reaction was quenched by the additon of 25% aqueous NH$_4$OAc solution, extracted with EtOAc, dried over MgSO$_4$ and evaporated in vacuo. The title product was purified by flash chromatography (30% to 50% EtOAc in hexane) (120 mg).

$^1$H NMR (CD$_3$COCD$_3$) δ7.50 (2H, d), 7.15 (2H, m), 6.90 (2H, d), 6.70 (1H, dd), 5.40 (2H, s), 4.30 (2H, m), 3.90 (2H, m), 3.75 (3H, s), 2.70–3.20 (3H, m), 2.30 (3H, s), 2.05–2.20 (2H, m), 1.50 (3H, d).

Step 7: Methyl 4-(1-(4-bromobenzyl)-5-methoxy-2-methyl-1H-indol-3-yl)-2-methylpentanoate To the imide of Step 6 (120 mg, 0.240 mmol) dissolved in THF (1.2 mL) at −78° C. was added a 0.5M KHMDS/toluene solution (722 mL). The reaction mixture was brought to −40° C. then recooled at −78° C. and an excess of MeI (100 mL) was added. After a few minutes at −40° C., the reaction was quenched with a 25% aqueous NH$_4$OAc solution, extracted with EtOAc, dried over MgSO$_4$, filtered and evaporated in vacuo. The title compound was purified by flash chromatography to afford 120 mg of material as a mixture of diastereoisomers. The auxiliary was removed as described for Example 11, Step 2. The isomers were partially resolved by purification over silica gel (10% EtOAc in hexane) at the methyl ester level. For the less polar isomer:

$^1$H NMR (CD$_3$COCD$_3$) δ7.50 (2H, d), 7.15 (1H, d), 7.10 (1H, d), 6.90 (2H, d), 6.65 (1H, dd), 5.40 (2H, s), 3.85 (3H, s), 3.50 (3H, s), 3.10 (1H, m), 2.30 (3H, s), 2.05–2.20 (3H, m), 1.40 (3H, d), 1.00 (3H, d).

Step 8: 4-(1-(4-Bromobenzyl)-5-methoxy-2-methyl-1H-indol-3-yl)-2-methylpentanoic acid The ester of Step 7 was hydrolysed as described in Example 7, Step 6 to give the title compound.

$^1$H NMR (CD$_3$COCD$_3$) δ7.45 (2H, d), 7.20 (1H, d), 7.10 (1H, d), 6.90 (2H, d), 6.70 (1H, dd), 5.40 (2H, s), 3.80 (3H, s), 3.50 (3H, s), 2.30 (3H, s), 2.05–2.20 (3H, m), 1.40 (3H, d), 1.00 (3H, d).

EXAMPLE 16

4-(1-(4-Bromobenzyl)-5-methoxy-2-methyl-1H-indol-3-yl)-4-oxobutanoic acid

Step 1: Methyl 4-(5-methoxy-2-methyl-1H-indol-3-yl)-4-oxobutanoate

To a solution of ethylmagnesium bromide in ether (3.0M; 7.1 mL; aldrich) was added a solution of 5-methoxy-2-methylindole (3.29 g) in ether (18 mL) at r.t. After 20 min, addition of a solution of zinc chloride in ether (1M; 20.4 mL; aldrich) resulted in the formation of a thick yellow solid. The suspension was stirred mechanically for 30 min before the rapid addition of a solution of 3-carbomethoxypropionyl chloride (2.6 mL) in ether (10 mL). The resulting mixture was vigorously stirred at r.t. for 3 h before the addition of saturated aqueous NH$_4$Cl and dichloromethane. The two phases were separated and the organic phase was washed successively with saturated aqueous NaHCO$_3$ and brine, dried (MgSO$_4$) and evaporated. Trituration of the residue in ether afforded the title compound as a pink solid.

$^1$H NMR (CDCl$_3$) δ8.45 (1H, br), 7.55 (1H, s), 7.20 (1H, d), 6.80 (1H, d), 3.85 (3H, s), 3.70 (3H, s), 3.25 (2H, t), 2.80 (2H, t), 2.70 (3H, s).

Step 2: Methyl 4-(1-(4-bromobenzyl)-5-methoxy-2-methyl-1H-indol-3-yl)-4-oxobutanoate Following the procedure described in Example 7, Step 2 but using the indole from Step 1 as substrate the title product was obtained as a white solid.

$^1$H NMR (CDCl$_3$) δ7.60 (1H, s), 7.40 (2H, d), 7.10 (1H, d), 6.80 (3H, m), 5.25 (2H, s), 3.85 (3H, s), 3.70 (3H, s), 3.30 (2H, t), 2.80 (2H, t), 265 (3H, s).

Step 3: 4-(1-(4-Bromobenzyl)-5-methoxy-2-methyl-1H-indol-3-yl)-4-oxobutanoic acid Following the procedure described in Example 7, Step 6, the ester from Step 2 was hydrolysed to give the title compound as a white solid; m.p. 215°–217° C.

$^1$H NMR (CDCl$_3$) δ7.50 (1H, s), 7.40 (2H, d), 7.10 (1H, d), 6.80 (3H, m), 5.30 (2H, s), 3.90 (3H, s), 3.35 (2H, t), 2.85 (2H, t), 2.70 (3H, s).

EXAMPLE 17 cis-2-[(1-(4-Bromobenzyl)-5-methoxy-2-methyl-1H-indol-3-yl)methyl]cyclopropanecarboxylic acid Step 1: Methyl 2-[(1-(4-bromobenzyl)-5-methoxy-2-methyl-1H-indol-3-yl)-2(Z)-butenoate To a −78° C. slurry of bis(2,2,2-trifluoroethyl) methoxycarbonylmethyl)phosphonate (500 mg, 1.55 mmol) and 18-crown-6 (1.9 g, 7.3 mmol) in 16 mL THF was added KHMDS (0.5M in toluene, 3.1 mL, 1.54 mmol) and the resulting mixture was stirred 30 minutes. The aldehyde from Example 7, Step 3 (545 mg, 1.46 mmol) dissolved in 3 mL THF and cooled to −78° C. was then added to the phosphonate via cannula and the resulting mixture was stirred for 1 h at −78° C., then quenched with saturated NH$_4$Cl. After extraction with ether, the organic layers were washed with brine, dried over MgSO$_4$ and concentrated. Purification by flash chromatography (20% ethyl acetate in hexane) provide 480 mg of the title compound.

$^1$H NMR (CDCl$_3$) δ7.36 (2H, d), 7.02 (2H, m), 6.75 (3H, m), 6.3 (1H, dt), 5.8 (1H, dr), 5.18 (2H, s), 4.1 (2H, d), 3.82 (3H, s), 3.77 (3H, s), 2.25 (3H, s).

Step 2: Methyl cis-2-[(1-(4-Bromobenzyl)-5-methoxy-2-methyl-1H-indol-3-yl)methyl]cyclopropanecarboxylate The olefinic ester from Step 2 (435 mg, 1.02 mmol) in 2 mL CH$_2$Cl$_2$ was treated with excess diazomethane/Et$_2$O solution and palladium acetate (5 mg) at −5° C. for 10 min. Evaporation to dryness and purification by flash chromatography (20% to 25% ethyl acetate in hexane) provided 145 mg of the title compound.

$^1$H NMR (CDCl$_3$) δ7.37 (2H, d), 7.07 (1H, d), 7.02 (1H, d), 6.75 (3H, m), 5.19 (2H, s), 3.85 (3H, s), 3.18 (3H, s), 2.93 (2H, d), 2.24 (3H, s), 1.74 (1H, m), 1.6 (1H, m), 1.15 (1H, m), 1.08 (1H, m).

Step 3: cis-2-[(1-(4-Bromobenzyl)-5-methoxy-2-methyl-1H-indol-3-yl)methyl]cyclopropanecarboxylic acid To the ester from Step 2 (145 mg, 0.33 mmol) in 3 mL THF and 3 mL MeOH was added 2N NaOH (1 mL, 2 mmol) and the reaction mixture was stirred at r.t. for 16 h. Excess 0.5N citric acid was added and the mixture was extracted with ethyl acetate. The organic layer was washed with brine, dried over MgSO$_4$ and evaporated. Purification by flash chromatogrpahy on silicic acid (20% to 40% ethyl acetate in hexane) provided 99 mg of the title compound.

$^1$H NMR (CDCl$_3$) δ7.34 (2H, d), 7.08 (1H, d), 7.02 (1H, d), 6.75 (3H, m), 5.18 (2H, s), 3.85 (3H, s), 2.99 (2H, d), 2.25 (3H, s), 1.8–1.65 (2H, m), 1.25–1.1 (2H, m).

EXAMPLE 18

(R)-(–)-4-(1-(4-Bromobenzyl)-5-methoxy-2-methyl-1H-indol-3-yl) -3-methylbutanoic acid Step 1: (R)-Methyl 5-formyl-3-methylpentanoate Ozone generated by a Welsbach Ozonator was passed, at –78° C., into a solution of R(+) methyl citronellate (JACS 1968, 90, 3525; 3.0 g) in MeOH (30 mL) for 1.5 h. There was added more MeOH (60 mL) and triphenylphosphine (5.13 g, 1.2 eq.) and the mixture was stirred at room temperature for 45 min. The methanol was evaporated off, the residue was diluted with Et$_2$O (100 mL) and the insoluble phosphine oxide filtered. The filtrate material was chromatographed on silica gel, eluting with a 1:3 mixture of ethyl acetate and hexane, to afford the compound as a colorless oil (1.25 g).

$^1$H NMR (CDCl$_3$) δ9.75 (1H, s), 3.65 (3H, s), 2.44 (2H, m), 2.30 (1H, dd), 2.15 (1H, m), 1.96 (1H, m), 1.67 (1H, m), 1.54 (1H, m), 0.94 (3H, d).

Step 2: Methyl 6-(R,S)-hydroxy-3(R)-methylheptanoate

To a solution of aldehyde from Step 1 (1.03 g, 6.5 mmol) in THF (20 mL) at –70° C. was added 1.4M methyl magnesium bromide in THF-toluene 1:3 (4.66 mL, 6.52 mmol). The mixture was stirred at –70° C. for 45 minutes, quenched with aqueous saturated NH$_4$Cl and allowed to warm up to room temperature. It was diluted with ether, and the organic phase was washed twice with brine, dried over MgSO$_4$ and evaporated down. The residue was chromatographed on silica gel, eluting with a 1:2 mixtue of ethyl acetate and hexane, to afford the desired compound (293 mg) as a colorless oil.

$^1$H NMR (CDCl$_3$) δ3.77 (1H, m), 3.64 (3H, s), 2.30 (1H, dd), 2.13 (1H, m), 1.93 (1H, m), 1.42 (4H, m), 1.18 (3H, d), 0.92 (3H, d). OH pattern not observed.

Step 3: (R)-Methyl 3-methyl-6-oxoheptanoate

To a solution of alcohol from Step 2 (293 mg) in CH$_2$Cl$_2$ (12 mL) was added a mixture of pyridinium chlorochromate (542 mg, 1.5 eq) and celite (542 mg). The suspension was stirred at r.t. overnight, and allowed to settle. The supernatant was collected and evaporated down to a residue which was chromatographed on silica gel, eluting with a 1:2 mixtue of EtOAc and hexane, to afford the desired ketone as a colorless liquid (189 mg).

$^1$H NMR (CDCl$_3$) δ3.64 (3H, s), 2.43 (2H, m), 2.29 (1H, dd), 2.13 (1H, m), 2.12 (3H, s), 1.92 (1H, m), 1.61 (1H, m), 1.45 (1H, m), 0.92 (3H, s).

Step 4: (R)-Methyl 4-(1-(4-bromobenzyl)-5-methoxy-2-methyl-1H-indol-3-yl)-3-methylbutanoate A mixture of ketone from Step 3 (92 mg, 0.3 mmol), N-(4-bromobenzyl)-N-(4-methoxyphenyl))hydrazine (52 mg, 0.3 mmol) from Example 1, Step 5, acetic acid (36 mg, 0.6 mmol) and toluene (3 mL) was stirred at room temperature for 1.5 h. The solvent was evaporated and replaced by ethanol (3 mL). Then acetyl chloride (110 mg, 5 eq) was added and the mixture was heated at 60° C. for 45 min. After evaporation of the ethanol, the mixture was chromatographed on silica gel, eluting with a 1:3 mixture of EtOAc and hexane, to afford the product as an oil which solidified (80 mg).

$^1$H NMR (CDCl$_3$) δ7.36 (2H, d), 7.00 (2H, m), 6.77 (2H, d), 6.74 (1H, t), 5.19 (2H, s), 3.83 (3H, s), 3.62 (3H, s), 2.70 (1H, m), 2.56 (1H, m), 2.34 (2H, m), 2.22 (3H, s), 2.18 (1H, m), 0.96 (3H, d).

Step 5: (R)-(–)-4-(1-(4-Bromobenzyl)-5-methoxy-2-methyl-1H-indol-3-yl)-3-methylbutanoic acid To a solution of ester from Step 4 (75 mg) in THF (1.5 mL) and methanol (1.5 mL) there was added 1N aq. NaOH (1 mL) and the mixture was refluxed for 1 h. The mixture was concentrated until solids appeared, diluted with water and acidified with 1N aq. HCl (2 mL). The mixture was extracted twice with ether, the extracts washed twice with water, dried and evaporated to a solid residue which was triturated with hexane and filtered, affording the title compound as a cream colored solid (61 mg). [α]$_D$=–4.4° (c=1, acetone)

EXAMPLE 19

2-[(5-Bromo-1-(4-bromobenzyl)-2-methyl-1H-indol-3-yl)methyl]benzoic acid

Step 1: Methyl 2-[(5-bromo-1-(4-bromobenzyl)-2-methyl-1H-indol-3-yl)methyl]benzoate To a room temperature solution of N-(4-bromobenzyl)-N-(4-bromophenyl)hydrazine (335 mg, 0.941 mmol) and methyl 2-(3-oxobutyl)benzoate (202 mg, 0.98 mmol) in 6 mL dioxane was added 1.5 mL of 4N HCl solution in dioxane. Heated to 70° C. for 16 h, then concentrated, the residue was partitioned between EtOAc and water, then washed with 1M HCl and brine. Dried over sodium sulfate, filtered and concentrated. Purification by flash chromatography (40% CH2Cl$_2$/Hexanes) provided 195 mg of the title compound.

$^1$H NMR (CD$_3$COCD$_3$) δ7.82 (1H, dd), 7.50 (2H, m), 7.45 (1H, d), 7.37 (1H, m), 7.29 (2H, m), 7.15 (2H, m), 6.95 (2H, m), 5.47 (2H, s), 4.46 (2H, s), 3.85 (3H, s), 2.32 (3H, s).

Step 2: 2-[(5-Bromo-1-(4-bromobenzyl)-2-methyl-1H-indol-3yl)methyllbenzoic acid

To a mixture of ester from Step 1 (195 mg, 0.37 mmol) in 25 mL EtOH and 8 mL H$_2$O was added 1 mL of 8N KOH and the mixture was refluxed for 45 min. Cooled to room temperature and concentrated. The residue was partitioned between EtOAc and 1M HCl, then washed with brine and dried over sodium sulfate, filtered and concentrated. Crystalization from CH2Cl$_2$-Hexanes provided 180 mg of the title compound.

$^1$H NMR (CD$_3$COCD$_3$) δ7.93 (1H, dd), 7.48 (3H, m), 7.39 (1H, m), 7.30 (2H, m), 7.14 (2H, m), 6.94 (2H, m), 5.45 (2H, s), 4.50 (2H, s), 2.34 (3H, s).

EXAMPLE 20

[2-(1-(4-Bromobenzyl)-5-methoxy-2-methyl-1H-indol-3-yl) phenyl]acetic acid, sodium salt Step 1: 2-(1-(4-Bromobenzyl)-5-methoxy-2-methyl-1 H-indol-3-yl) benzoic acid A solution of the hydrazine from Example 1, Step 5, (675 mg, 2.2 mmol), 2-(2-oxopropyl)benzoic acid (425 mg, 2.4 mmol) and acetic acid (314 μL, 5.5 mmol) in toluene was warmed to 65° C. for 1 h after what the mixture was evaporated and acetic acid was removed with the help of heptane in vacuo. To a portion of the residue (100 mg) in dioxane (1 mL) was added 4M HCl in dioxane (2 mL) and the mixture was heated to 65° C. for 1 h. It was then cooled to 25° C. and poured on a mixture of ice water and ethyl acetate. The organic layer was washed with brine and dried with MgSO$_4$. Removal of the solvents yielded a residue which was purified by flash chromatography. The remaining portion of the intermediate was processed identically and combined to give the product (357 mg). Anal. Calcd. for C$_{24}$H$_{20}$BrNO$_3$: C, 64.01; H, 4.48; N, 3.11. Found: C, 63.92; H, 4.51; N, 3.04.

Step 2: [2-(1-(4-Bromobenzyl)-5-methoxy-2-methyl-1H-indol-3-yl) phenyl]methanol

A solution of the acid from Step 1 (300 mg, 0.66 mmol) and BH$_3$ Σ SMe$_2$ (0.1 mL, 1 mmol) in THF (3 mL) was gently refluxed for 2 h. The cooled mixture was poured over icy dilute HCl and ethyl acetate. The organic layer was washed with brine and dried with MgSO$_4$. Removal of the solvents yielded essentially pure product (285 mg).

$^1$H NMR (CD$_3$COCD$_3$) δ7.7–7.8 (1H, dd), 7.2–7.5 (6H, m), 7.0 (2H, d), 6.6–6.8 (2H, m), 5.45 (2H, s), 4.4–4.6 (2H, m), 3.7 (3H, s), 2.8–2.9 (1H, br), 2.2 (3H, s).

Step 3: [2-(1-(4-Bromobenzyl)-5-methoxy-2-methyl-1H-indol-3-yl)]phenyl]bromomethane To a 0° C. solution of Ph$_3$P (209 mg, 0.8 mmol) in CH2Cl$_2$ (4 mL) was added Br$_2$ (38 µL, 0.73 mmol) and the mixture was slowly warmed up to 25° C. and stirred for 15 min. It was cooled to 0° C. and a solution of the alcohol from Step 2 (285 mg, 0.66 mmol) in CH$_2$Cl$_3$ (2 mL) was added dropwise. After 1 h at 0° C. and 0.25 h at 25° C., the mixture was poured into cold dilute NaHCO$_3$ and CH$_2$Cl$_2$. The organic layer was washed with brine and dried with MgSO$_4$. Removal of the solvent left a residue which was purified on SiO$_2$ to yield the product (284 mg).

$^1$H NMR (CD$_3$COCD$_3$) δ7.6–7.7 (1H, m), 7.4–7.5 (4H, m), 7.3–7.4 (2H, d), 6.9–7.0 (2H, m), 6.7–6.8 (1H, dd), 6.65 (1H, d), 5.5 (2H, AB), 4.55 (2H, s), 3.7 (3H, s), 2.2 (3H, s).

Step 4: Methyl [2-(1-(4-bromobenzyl)-5-methoxy-2-methyl-1H-indol-3-yl)phenyl]acetate A solution of the bromide from Step 3 (280 mg, 0.56 mmol), NaH$_2$PO$_4$.H$_2$O (235 mg, 1.7 mmol) and KCN (110 mg, 1.7 mmol) in DMF (6 mL) was warmed to 75° C. for 4 h. It was cooled and poured over ice water and Et$_2$O. The organic layer was washed with brine, dried with MgSO$_4$ and the solvent removed to yield a residue (239 mg) which was essentially pure and was used as such.

The residue was dissolved in MeOH (10 mL) and cooled to 0° C. The solution was saturated with HCl(g) and then warmed up to reflux and kept 4 h at this temperature. It was cooled and poured over ice water and ethyl acetate. Solid NaHCO$_3$ was carefully added until the pH was 8. The organic layer was washed with brine, dried with MgSO$_4$ and the solvent removed to yield an essentialy pure product (238 mg).

$^1$H NMR (CD$_3$COCD$_3$) δ7.2–7.5 (7H, m), 6.9–7.0 (2H, d), 6.65–6.75 (1H, dd), 6.6 (1H, d), 5.5 (2H, AB), 4.55 (2H, s), 3.7 (3H, s), 2.25 (3H, s).

Step 5: [2-(1-(4-Bromobenzyl)-5-methoxy-2-methyl-1H-indol-3-yl)phenyl]acetic acid, sodium salt A solution of the ester of Step 4 (238 mg) and 2N NaOH (500 µL, 1 mmol) in MeOH (5 mL) was heated to reflux for 4 h. It was cooled and poured over icy dilute HCl and ethyl acetate. The organic layer was washed with brine, dried with MgSO$_4$ and the solvents were removed to yield a residue which was purified by chromatography over SiO$_2$. The acid (159 mg) was treated with 2N NaOH (170 µL) and the mixture freeze dried to yield the product as a dihydrate. Anal. Cald. for C$_{25}$H$_{21}$BrNO$_5$Na.2H$_2$O: C, 57.93; H, 4.86; N, 2.70. Found: C, 57.84; H, 4.69; N, 2.71.

EXAMPLE 21

2-[(1-(4-Bromobenzyl)-5-methoxy-2-methyl-1H-indol-3-yl)methyl]benzoic acid

Step 1: Methyl 2-[(5-methoxy-2-methyl-1H-indol-3-yl) methyl]benzoate

A mixture of 2-methyl-5-methoxy indole (1.01 g, 6.2 mmol), methyl 2-(bromomethyl)benzoate (1.60 g, 6.9 mmol) and silver (I) oxide (1.59 g, 6.9 mmol) in dioxane (8 mL) was heated to 50° C. for 20 h. The mixture was cooled, diluted with EtOAc and filtered thorugh celite. The filtrate was concentrated and the resulting residue was chromatographed to give 406 mg of the title compound.

Step 2: Methyl 2-[(1-(4-bromobenzyl)-5-methoxy-2-methyl-1H-indol-3-yl)methyl]benzoate To the product of Step 1 (210 mg, 0.68 mmol) in dry DMF (5 mL) at 0° C. was added NaH (30 mg, 0.74 mmol, 60% in oil) followed by 4-bromobenzyl bromide (174 mg, 0.7 mmol). The mixture was stirred at r.t. for 0.5 h. NH$_4$Cl solution was added. The mixture was extracted with EtOAc. Chromatography of the concentrated organic extract gave 272 mg of the title compound.

Step 3: 2-[(1-(4-Bromobenzyl)-5-methoxy-2-methyl-1H-indol-3-yl)methyl]benzoic acid To a solution of the product of Step 2 (300 mg, 0.62 mmol) in THF (2 mL) and MeOH (4 mL) was added NaOH (3N, 0.62 mL). The mixture was refluxed for 2.5 h and then cooled to r.t. Acidification with 1N HCl followed by extraction with EtOAc gave 148 mg of the title compound after evaporation of solvent. Anal. calcd. for C$_{25}$H$_{22}$NO$_3$Br H$_2$O: C, 63.43, H, 4.90; N, 2.96; found: C, 63.77; H, 4.89; N, 3.12.

$^1$H NMR (CD$_3$COCD$_3$) δ7.92 (1H, dd), 7.46 (2H, d), 7.37 (1H, m), 7.27 (1H, m), 7.19 (2H, m), 6.94 (2H, d), 6.87 (1H, d), 6.66 (1H, dd), 5.41 (2H, s), 4.51 (2H, s), 3.67 (3H, s), 2.29 (3H, s).

EXAMPLE 22

[3-(4-Bromobenzyl)-5-methoxy-2-methyl-1H-indol-3-yl]benzoic acid, sodium salt

Step 1: 3-Bromophenylacetone

Trimethylaluminium in toluene (30 mL, 2M) was added to a −78° C. solution of m-bromobenzyl cyanide (3.92 g, 20 mmol) in toluene (20 mL) and the mixture was slowly warmed up and refluxed for 12 h. After being cooled to 0° C., the solution was carefully added to crushed ice and made acidic with 6N HCl. Ethyl acetate was added and the mixture was vigorously stirred for 1 h. The organic layer was washed with NaHCO$_3$, brine and dried with MgSO$_4$. Removal of the solvent left an oil (4.53 g) which was used as such in the next step.

$^1$H NMR (CD$_3$COCD$_3$) δ7.4–7.5 (2H, m), 7.1–7.3 (2H, m), 3.8 (2H, s),2.15(3H, s).

Step 2: 3-(5-methoxy-2-methyl-1H-indol-3-yl) bromobenzene

The ketone from Step 1 (1.065 g, 5 mmol) and 4-methoxyphenylhydrazine hydrochloride (870 mg, 5 mmol) in toluene (20 is mL) were gently warmed up to 60° C. After 1 h, 4M HCl/dioxane (2 mL) was added and the mixture was heated at 60° C. for 1 h. It was then cooled, poured over ice water and ethyl acetate. The organic layer was separated, washed with dilute NaHCO$_3$. Removal of the solvents left a residue which was purified by chromatography over SiO$_2$ to afford the product (433 mg).

$^1$H NMR (CD$_3$COCD$_3$) δ10.1 (1H, br), 7.7–7.0 (6H, m), 6.7–6.8 (1H, dd), 3.75 (3H, s), 2.5 (3H, s).

Step 3: Methyl 3-(5-methoxy-2-methyl-1H-indol-3-yl) benzoate

To a –78° C. solution of the bromide (539 mg, 1.7 mmol) from Step 2 in THF (10 mL) was added dropwise n-BuLi (1.4M, 2.67 mL). After 15 min the mixture was poured over crushed CO$_2$ and allowed to warm up to room temperature. Dilute HCl (25 mL) was added and the product was extracted in ethyl acetate. The organic layer was washed with brine, dried with MgSO$_4$ and the solvents removed to leave a residue which was treated with a slight excess of diazomethane in ether. Removal of the solvent yielded the product (351 mg).

$^1$H NMR (CD$_3$COCD$_3$) δ10.1 (1H, br), 8.2 (1H, m), 7.5–8.0 (3H, m), 7.3 (1H, d), 7.1 (1H, d), 6.7–6.8 (1H, dd), 3.9 (3H, s), 3.7 (3H, s), (3H, s).

Step 4: Methyl 3-[1-(4-bromobenzyl)-5-methoxy-2-methyl-1H-indol-3-yl]benzoate

To a 0° C. mixture of the indole from Step 3 (285 mg, 0.96 mmol) and 4-bromobenzyl bromide (310 mg, 1.05 mmol) in DMF (5 mL) was added NaH (44 mg, 1.1 mmol). The mixture was warmed up to r.t. and stirred for 1.5 h after which time it was poured on a mixture of ice water and Et$_2$O. The organic layer was washed with brine, dried with MgSO$_4$ and the solvent removed to yield a residue which was used as such in the next step.

$^1$H NMR (CD$_3$COCD$_3$) δ8.15 (1H, b), 7.9–8.0 (1H, m), 7.7–7.8 (1H, m), 7.4–7.65 (5H, m), 7.3 (1H, d), 7.1 (1H, d), 6.8 (1H, dd), 5.5 (2H, 3.9 (3H, s), 3.75 (3H, s), 2.45 (3H, s).

Step 5: 3-[1-(4-Bromobenzyl)-5-methoxy-2-methyl-1H-indol-3-yl]benzoic acid

A mixture of the ester from Step 4 (445 mg, 0.96 mmol) and 2N NaOH (1.5 mL, 3 mmol) in ethanol (10 mL) was heated to reflux for 2 h then it was cooled and kept at 25° C. for 16 h. Ethanol was removed and the residue dissolved in water (20 mL). 1N HCl (5 mL) was added dropwise and under vigorous stirring; the solid was filtered and dried. A swish in Et$_2$O/hexane mixture yielded the pure product (350 mg) Anal. calcd. for C$_{24}$H$_{20}$BrNO$_3$: C, 64.01; H, 4.48; N, 3.11. Found: C, 63.56; H, 4.35; N, 3.12.

Step 6: 3-[1-(4-Bromobenzyl)-5-methoxy-2-methyl-1H-indol-3-yl]benzoic acid, sodium salt Using the procedure described in Example 2, Step 6 the title compound was obtained.

Examples 23 to 64 were prepared analogously to the examples listed above and according to Methods A to K.

EXAMPLE 23

4-[1-(4-Bromobenzyl)-2,5-dimethyl-1H-indol-3-yl] butanoic acid $^1$H NMR (CD$_3$COCD$_3$) δ7.45 (2H, d), 7.33 (1H, s), 7.12 (1H, d), 6.91 (2H, d), 6.87 (1H, d), 5.37 (2H, s), 2.8 (2H, t), 2.39 (3H, s), 2.32 (2H, t), 2.30 (3H, s), 1.9 (2H, m).

EXAMPLE 24

4-[5-Bromo-1-(4-bromobenzyl)-2-methyl-1H-indol-3-yl]butanoic acid $^1$H NMR (CD$_3$COCD$_3$) δ7.73 (1H, s), 7.48 (2H, d), 7.37 (1H, d), 7.15 (1H, d), 6.94 (2H, d), 5.42 (2H, s), 2.81 (2H, t), 2.35 (2H, t), 2.35 (3H, s), 1.9 (2H, m).

EXAMPLE 25

4-[1-(4-Chlorobenzyl)-5-methoxy-2-methyl-1H-indol-3-yl]-3-(ethane-1,2-diyl)butanoic acid $^1$H NMR (CD$_3$COCD$_3$) δ10.5 (1H, br), 7.30 (2H, d), 7.15 (1H, d), 7.13 (1H, s), 6.94 (2H, d), 6.68 (1H, d), 5.38 (2H, s), 3.80 (3H, 2), 3.0 (2H, s), 2.3 (3H, s), 2.29 (2H, s), 0.5–0.35 (4H, m).

EXAMPLE 26

4-[1-(4-Bromobenzyl)-5-chloro-2-methyl-1H-indol-3-yl]butanoic acid $^1$H NMR (CD$_3$COCD$_3$) δ7.58 (1H,s), 7.48 (2H, d), 7.30 (1H, d), 7.03 (1H, d), 6.94 (2H, d), 5.42 (2H, s), 2.81 (2H, t), 2.35 (2H, t), 2.35 (3H, s), 1.9 (2H, m).

EXAMPLE 27

4-[5-Bromo-1-(4-chlorobenzyl)-2-methyl-1H-indol-3-yl]butanoic acid $^1$H NMR (CDCl$_3$) δ7.64 (1H, s), 7.20 (2H, d), 7.14 (1H, d), 6.98 (1H, d), 6.70 (2H, d), 5.19 (2H, s), 2.76 (2H, t), 2.37 (2H, t), 2.25 (3H, s), 1.95 (2H, m).

EXAMPLE 28

4-[5-Chloro-1-(4-chlorobenzyl)-2-methyl-1H-indol-3-yl]butanoic acid $^1$H NMR (CDCl$_3$) δ7.48 (1H, s), 7.20 (2H, d), 7.02 (2H, s), 6.80 (2H, d), 5.20 (2H, s), 2.74 (2H, t), 2.37 (2H, t), 2.22 (3H, s), 1.93 (2H, m).

EXAMPLE 29

4-[1-(4-Bromo-2-fluorobenzyl)-5-chloro-2-methyl-1H-indol-3-yl]butanoic acid $^1$H NMR (CDCl$_3$) δ7.48 (1H, s), 7.26 (1H, d), 7.05 (1H, d), 7.02 (2H, s), 6.21 (1H, t), 5.21 (2H, s), 2.76 (2H, t) 2.36 (2H, t), 2.25 (3H, s), 1.95 (2H, m).

EXAMPLE 30

4-[1-(4-Bromo-2-fluorobenzyl)-5-chloro-2-methyl-1H-indol-3-yl]-2-methylbutanoic acid $^1$H NMR (CDCl$_3$) δ9.0 (1H, br), 7.48 (1H, s) 7.26 (1H, d), 7.05 (1H, d), 7.02 (2H, s), 6.21 (1H, t), 5.21 (2H, s), 2.74 (2H, t), 2.5 (1H, m), 2.25 (3H, s), 2.2 (1H, m), 1.72 (1H, m), 1.27 (3H, d).

EXAMPLE 31

4-[5-Methoxy-2-methyl-1-(4-methylthiobenzyl)-1H-indol-3-yl]-3-(ethane-1,2-diyl)butanoic acid $^1$H NMR (CD$_3$COCD$_3$) δ10.5 (1H, br), 7.14 (4H, m), 6.89 (2H, d), 6.66 (1H, dd), 5.32 (2H, s), 3.80 (3H, s), 3.0 (2H, s), 2.42 (3H, s), 2.31 (3H, s), 2.29 (2H, s), 0.5–0.35 (4H, m).

EXAMPLE 32

4-[5-Bromo-1-(4-bromobenzyl)-2-methyl-1H-indol-3-yl]-3-(ethane-1,2-diyl)butanoic acid $^1$H NMR (CD$_3$COCD$_3$) δ10.5 (1H, br), 7.76 (1H, s), 7.46 (2H, d), 7.27 (1H, d), 7.14 (1H, d), 6.90 (2H, d), 5.42 (2H, s), 3.01 (2H, s), 2.33 (3H, s), s), 2.29 (2H, s), 0.41 (4H, s).

EXAMPLE 33 trans 2-(4-[1-(4-Bromobenzyl)-5-chloro-2-methyl-1H-indol-3-yl]methyl) cyclopropanecarboxylic acid $^1$H NMR (CD$_3$COCD$_3$) δ7.6 (1H, d), 7.47 (2H, d), 7.30 (1H, d), 7.03 (1H, dd), 6.91 (2H, d), 5.42 (2H, s), 2.88 (2H, d), 2.37 (3H, s), 1.62 (1H, m), 1.51 (1H, m), 1.06 (1H, m), 0.89 (1H, m).

EXAMPLE 34

4-[1-(4-Bromobenzyl)-5-chloro-2-methyl-1 H-indol-3-yl]-3-methyl-butanoic acid $^1$H NMR (CD$_3$COCD$_3$) δ7.6 (1H, d), 7.46 (2H, d), 7.30 (1H, d), 7.02 (1H, dd), 6.91 (2H, d), 5.41 (2H, s), 2.8 (1H, dd), 2.6 (1H, dd), 2.35–2.2 (3H, m), 0.98 (3H, d).

EXAMPLE 35

4-[1-(4-Bromobenzyl)-5-chloro-2-methyl-1H-indol-3-yl]-2-methyl-butanoic acid $^1$H NMR (CD$_3$COCD$_3$) δ7.55 (1H, d), 7.46 (2H, d), 7.30 (1H, d), 7.01 (1H, dd), 6.91 (2H, d), 5.41 (2H, s), 2.81 (2H, t), 2.51 (1H, m), 2.33 (3H, s), 1.97 (1H, m), 1.7 (1H, m), 1.21 (3H, d).

EXAMPLE 36

4-[1-(4-Bromobenzyl) -5-chloro-2-methyl-1H-indol-3-yl]-2,3-dimethyl-butanoic acid Exact mass (FAB) for C$_{22}$H$_{24}$NO$_2$BrCl (MH$^+$) calculated: 448.06789; found: 448.06777.

EXAMPLE 37

4-(1-Benzyl-5-chloro-2-methyl-1H-indol-3-yl) pentanoic acid

Exact mass (FAB) for C$_{21}$H$_{23}$NO$_2$Cl (MH$^+$) calculated: 356.14173; found: 356.14175.

EXAMPLE 38

4-[1-(4-Bromobenzyl)-5-chloro-2-methyl-1H-indol-3-yl]pentanoic acid

Exact mass (FAB) for C$_{21}$H$_{22}$NO$_2$ClBr calculated: 434.05224; found:434.05205.

EXAMPLE 39

4-[1-(4-Bromobenzyl)-5-methoxy-2-methyl-1H-indol-3-yl]-3-methyl-butanoic acid $^1$H NMR (CD$_3$COCD$_3$) δ7.45 (2H, d), 7.15 (2H, m), 6.91 (2H, d), 6.70 (1H, dd), 5.38 (2H, s), 3.80 (3H, s), 2.8 (1H, dd), 2.6 (1H, dd), 2.38 (1H, m), 2.31 (3H, s), 2.22 (1H, dd), 0.99 (3H, d).

EXAMPLE 40

4-[5-Methoxy-2-methyl-1-(4-methanesulfoxylbenzyl)-1H-indol-3-yl]-3-(ethane-1,2-diyl)butanoic acid $^1$H NMR (CD$_3$COCD$_3$) δ7.58 (2H, d), 7.2–7.05 (4H, m), 6.79 (1H, dd), 5.46 (2H, s), 3.80 (3H, s), 3.0 (2H, s), 2.64 (3H, s), 2.31 (3H, s), 2.28 (2H, s), 0.5–0.35 (4H, m).

EXAMPLE 41

4-[1-(4-Bromobenzyl)-5-methoxy-2-methyl-1H-indol-3-yl]pentanoic acid

Exact mass (FAB) for C$_{21}$H$_{22}$NO$_2$ClBr calculated: 430.10178; found:430.10174.

EXAMPLE 42

4-[1-(4-Bromobenzyl)-5-methoxy-2-methyl-1H-indol-3-yl]-2,3-dimethylbutanoic acid, sodium salt $^1$H NMR (CD$_3$COCD$_3$) δ7.41 (2H, d), 7.22 (1H, dd), 7.10 (1H, d), 6.86 (2H, d), 6.62 (1H, dd), 5.31 (2H, s), 3.80 (3H, s), 3.0–2.8 (2H, m), 2.3–2.1 (3H, m), 2.25 (3H, s), 1.15–1.05 (3H, 2d), 0.85–0.75 (3H, 2d).

EXAMPLE 43

3(S), 4-[1-(4-Bromobenzyl)-5-chloro-2-methyl-1H-indol-3-yl]-3-methylbutanoic acid, sodium salt Exact mass (FAB) for C$_{21}$H$_{21}$NO$_2$BrClNa (MH$^+$Na) calculated: 456.03419; found: 456.03435.

EXAMPLE 44

3(R), 4-[1-(4-Bromobenzyl)-5-chloro-2-methyl-1H-indol-3-yl]-3-methylbutanoic acid, sodium salt Exact mass (FAB) for C$_{21}$H$_{21}$NO$_2$BrClNa (MH$^+$Na) calculated: 456.03419; found:456.03435. For methyl ester: [α]$_D$=–12.0° (c=0.3, CD$_3$COCD$_3$)

EXAMPLE 45

4-[1-(4-Bromobenzyl)-5-methoxy-2-methyl-1H-indol-3-yl]-3-(ethane-1,2-diyl)-2-methylbutanoic acid $^1$H NMR (CD$_3$COCD$_3$) δ7.43 (2H, d), 7.16 (1H, d), 7.04 (1H, d), 6.86 (2H, d), 6.68 (1H, dd), 5.36 (2H, s), 3.80 (3H, s), 3.03 (2H, s), 2.26 (3H, s), 2.19 (1H, q), 1.32 (3H, d), 0.45–0.15 (4H, m).

EXAMPLE 46

4-[1-(4-Bromobenzyl)-5-methoxy-2-methyl-1H-indol-3-yl]-3-ethylbutanoic acid $^1$H NMR (CD$_3$COCD$_3$) δ7.45 (2H, d), 7.17 (1H, d), 7.15 (1H, s), 6.91 (2H, d), 6.70 (1H, d), 5.37 (2H, s), 3.80 (3H, s), 2.72 (2H, t), 2.4–2.2 (2H, m), 2.31 (3H, s),2.18 (1H, m), 1.5–1.35 (2H, m), 0.96 (3H, t).

EXAMPLE 47

4-[1-(4-Bromobenzyl)-5-methoxy-2-methyl-1H-indol-3-yl]-3-methylpentanoic acid, sodium salt Mass (CI): 466(MH$^+$+Na), 443(MH$^+$)

EXAMPLE 48

4-[1-(4-Bromobenzyl)-5-methoxy-2-methyl-1H-indol-3-yl]-3,3-dimethylbutanoic acid, sodium salt Mass (CI): 444,446(MH$^+$), 426,428(MH$^+$–H$_2$O), 366, 342,344.

EXAMPLE 49

4-[1-(4-Bromobenzyl)-5-methyl-5-trifluoromethyl-1H-indol-3-yl]butanoic acid $^1$H NMR (CD$_3$COCD$_3$) δ7.95 (1H, s), 7.5 (3H, m), 7.34 (1H, d), 6.97 (2H, d), 5.51 (2H, s), 2.89 (2H, t), 2.39 (3H, s), 2.37 (2H, t), 1.92 (2H, m).

EXAMPLE 50

2(R) 4-[1-(4-Bromobenzyl)-5-chloro-2-methyl-1H-indol-3-yl]-2-methylbutanoic acid $^1$H NMR (CD$_3$COCD$_3$) δ7.54 (1H, d), 7.44 (2H, d), 7.29 (1H, d), 7.00 (1H, dd), 6.91 (2H, d),5.41 (2H, s),2.78 (2H, 0.2.5 (1H, m), 2.31 (3H, s), 1.95 (1H, m), 1.7 (1H, m), 1.20 (3H, d).

EXAMPLE 51

2(S),4-[1-(4-Bromobenzyl)-5-chloro-2-methyl-1H-indol-3-yl]-2-methylbutanoic acid, sodium salt Exact mass (FAB) for C$_{21}$H$_{21}$NO$_2$ClBrNa calculated: 456.03419; found: 456.03435.

EXAMPLE 52

4-[1-(4-Bromobenzyl)-5-methoxy-2-methyl-1H-indol-3-yl]-2-benzylbutanoic acid $^1$H NMR (CD$_3$COCD$_3$) δ7.43 (2H, d), 7.20 (5H, m), 7.16 (1H, d), 7.00 (1H, d), 6.90 (2H, d), 6.67 (1H, dd), 5.33 (2H, s), 3.75 (3H, s), 3.00 (1H, m), 2.9–2.7 (4H, m), 2.22 (3H, s), 2.0–1.75 (2H, m).

EXAMPLE 53

4-[5-Chloro-1-(4-iodobenzyl)-2-methyl-1H-indol-3-yl]butanoic acid $^1$H NMR (CDCl$_3$) δ7.56 (2H, d), 7.46 (1H, s), 7.0 (2H, s), 6.61 (2H, d), 5.18 (2H, s), 2.74 (2H, t), 2.36 (2H, t), 2.22 (3H, s), 1.92 (2H, m).

EXAMPLE 54

4-[1-(4-Bromobenzyl) -5-methoxy-2-methyl-1H-indol-3-yl]-2-ethylbutanoic acid $^1$H NMR (CD$_3$COCD$_3$) δ7.44 (2H, d), 7.16 (1H, d), 7.09 (1H, d), 6.92 (2H, d), 6.70 (1H, dd), 5.35 (2H, s), 3.80 (3H, s), 2.76 (2H, m), 2.34 (1H, m), 2.30 (3H, s), 1.95 (1H, m), 1.75 (1H, m), 1.7–1.5 (2H, m), 0.91 (3H, t).

EXAMPLE 55

4-[5-Bromo-1-(4-bromobenzyl)-2-methyl-1H-indol-3-yl]-3,3-dimethylbutanoic acid

Mass (CI): 492,494 (MH$^+$), 476, 450.

EXAMPLE 56

4-[1-(4-Bromobenzyl)-5-chloro-2-methyl-1 H-indol-3-yl]-3,3-dimethylbutanoic acid Anal. calcd. for C$_{22}$H$_{23}$NO$_2$ClBr: C, 59.08; H, 5.18; N, 3.13. Found: C, 58.73; H, 5.15; N, 3.25.

EXAMPLE 57

2(R),3(R) 4-[1-(4-Bromobenzyl)-5-chloro-2-methyl-1H-indol-3-yl]-2,3-dimethylbutanoic acid $^1$H NMR (CD$_3$COCD$_3$) δ7.57 (1H, d), 7.45 (2H, d), 7.29 (1H, d), 7.00 (1H, dd), 6.91 (2H, d), 5.41 (2H, s), 2.9 (1H, dd), 2.5 (2H, m), 2.32 (3H, s), 2.18 (1H, m), 1.22 (3H, d), 0.88 (3H, d).

EXAMPLE 58

2(S),3(R) 4-[1-(4-Bromobenzyl)-5-chloro-2-methyl-1H-indol-3-yl]-2,3-dimethylbutanoic acid $^1$H NMR (CD$_3$COCD$_3$) δ7.57 (1H, d), 7.45 (2H, d), 7.29 (1H, d), 7.01 (1H, dd), 6.90 (2H, d), 5.41 (2H, s), 2.85 (1H, m), 2.53 (1H, dd), 2.42 (1H, m), 2.32 (3H, s), 2.21 (1H, m), 1.18 (3H, d), 0.84 (3H, d).

EXAMPLE 59

3(R) 4-[1-(4-Iodobenzyl)-5-methoxy-2-methyl-1H-indol-3-yl]-3-methylbutanoic acid $^1$H NMR (CD$_3$COCD$_3$) δ7.62 (2H, d), 7.13 (1H, d), 7.11 (1H, d), 6.75 (2H, d), 6.65 (1H, dd), 5.36 (2H, s), 3.80 (3H, s), 2.8 (1H, dd), 2.6 (1H, dd), 2.4–2.15 (2H, m), 2.31 (3H, s), 0.98 (3H, d).

EXAMPLE 60

4-[1-(4-Bromobenzyl)-5-chloro-2-methyl-1H-indol-3-yl]-3-(ethane-1,2-diyl)butanoic acid $^1$H NMR (CD$_3$COCD$_3$) δ7.61 (1H, s), 7.48 (2H, d), 7.30 (1H, d), 7.03 (1H, d), 6.91 (2H, d), 5.42 (2H, s), 3.02 (2H, s), 2.33 (3H, s), 2.29 (2H, s), 0.42 (4H, s).

EXAMPLE 61

3(R) 4-[1-(4-Ethylthiobenzyl)-5-methoxy-2-methyl-1H-indol-3-yl]-3-methylbutanoic acid Mass (CI): 411 (MH$^+$), 324, 151.

EXAMPLE 62

Methyl 4-[1-(4-bromobenzyl)-5-methoxy-2-methyl-1H-indol-3-yl]butanoate $^1$H NMR (CD$_3$COCD$_3$) δ7.46 (2H, d), 7.17 (1H, d), 7.09 (1H, s), 6.92 (2H, d), 6.70 (1H, d), 5.35 (2H, s), 3.81 (3H, s), 3.60 (3H, s), 2.78 (2H,t), 2.34 (2H, t), 2.30 (3H, s), 1.91 (2H, m).

EXAMPLE 63

2-{[1-(4-Bromobenzyl)-5-methoxy-2-methyl-1H-indol-3-yl]acyl}benzoic acid

Mass (CI): 478 (MH$^+$).

EXAMPLE 64

5-[1-(4-Bromobenzyl)-5-methoxy-2-methyl-1H-indol-3-yl]-2-methylbenzoic acid $^1$H NMR (CD$_3$COCD$_3$) δ8.11 (1H, d), 7.60 (1H, dd), 7.50 (2H, d), 7.42 (1H, d), 7.29 (1H, d), 7.12, (1H, d), 7.04 (2H, d), 6.79 (1H, dd), 5.49 (2H, s), 3.78 (3H, s), 2.65 (3H, s), 2.44 (3H, s)

Examples 65 to 89 may be prepared analogously to the examples and Methods A to K listed above.

EXAMPLE 90

4-[1-(4-Bromobenzyl)-5-methoxy-2-methyl-1H-indol-3-yl]-3-methylbutanamide

To the acid of Example 7, Step 6, (600 mg, 1.39 mmol) in benzene (10.0 mL) was added at 0° C. DMF (50 mL) and oxalyl chloride. After a period of 30 min at 0° /C., THF (10.0 mL) was added to the resulting mixture and ammonia gas was bubbled until saturation. The mixture was stirred for 4 h at r.t. The reaction was poured over water, extracted with EtOAc, dried over Na$_2$SO$_4$, evaporated in vacuo and filtered over silica gel (50% EtOAc in THF) to provide the desired amide (530 mg).

¹H NMR (CD₃COCD₃) δ7.45 (2H, d), 7.17 (1H, d), 7.15 (1H, d), 6.90 (2H, d), 6.72 (1H, br), 6.70 (1H, rid), 6.10 (1H, br), 5.40 (2H, s), 3.75 (3H, s), 2.30 (3H, s), 2.10 to 2.50 (5H, m), 0.90 (3H, d).

EXAMPLE 91

4-(1-(4-Bromobenzyl)-5-methoxy-2-methyl-1H-indol-3-yl)-N-(2-pyridyl)butanamide

To the acid of Example 4, (400 mg, 0.96 mmol) in 30 mL CH₂Cl₂ at 0° C. was added a few drops of DMF followed by oxalyl chloride (100 μL, 1.15 mmol, dropwise). The reaction was stirred 15 min at 0° C., and then 2-amino pyridine (306 mg, 3.26 mmol) was added. The reaction mixture was stirred overnight at r.t., poured into water and extracted with ethyl acetate. The organic layer was washed with brine, dried over MgSO₄ and evaporated in vacuo. Purification by flash chromatography (20%, ethyl acetate in hexane) provided 101 mg of the title compound as a yellow solid.

¹H NMR (CDCl₃) δ8.36 (1H, d), 8.02 (1H, d), 7.85 (1H, t), 7.36 (2H, d), 7.11 (1H, t), 6.97 (2H, m), 6.79 (2H, d), 6.70 (1H, d), 5.16 (2H, s), 3.83 (3H, s), 2.8 (2H, t), 2.51 (2H, t), 2.25 (3H, s), 2.07 (2H, t).

EXAMPLE 92

[4-(1-(4-Bromobenzyl)-5-methoxy-2-methyl-1H-indol-3-yl)-3-(ethane-1,2-diyl)]butanoyl methanesulfonamide A mixture of acid from Example 2, Step 5, (201 mg, 0.44 mmol) and carbonyldiimidazole (99 mg, 0.61 mmol) was dissolved in 5 mL of CH₂C₂ and stirred 40 min at room temperature. Methanesulfonamide (72 mg, 0.76mmol) and DMAP (170 mg, 1.39 mmol) were then added, and the solution was stirred 28 h at room temperature. The mixture was partitioned between CH₂C₂ and 1M HCl, washed with brine, filtered through cotton and evaporated. Purification by flash chromatography on silicic acid (35% EtOAc/Hexane), provided 56 mg of the title compound.

¹H NMR (CD₃COCD₃) a 7.45 (2H, m), 7.15 (2H, m), 6.90 (2H, m), 6.69 (1H, m), 5.37 (2H, s), 3.80 (3H, s), 3.24 (3H, s), 2.98 (2H, s), 2.40 (2H, s), 2.30 (3H, s), 0.49 (4H, m).

Examples 93 to 107 were prepared analogously to the examples 90 to 92 listed above and according to Method L.

EXAMPLE 93

3(R) 4-[1-(4-Bromobenzyl)-5-methoxy-2-methyl-1H-indol-3-yl]-3-methylbutanamide

Mass (CI): 428,430 (MH⁺), 342,344, 169,170

EXAMPLE 94

3(R) 4-[1-(4-Bromobenzyl)-5-methoxy-2-methyl-1H-indol-3-yl]-N,N-dimethyl-3-methylbutanamide Anal. calc'd for C₂₄H₂₉N₂O₂Br.½H₂O: C, 61.8; H, 6.48; N, 6.01. Found: C, 61.3; H, 6.3; N, 5.88.

EXAMPLE 95

4-[1-(4-Bromobenzyl)-5-methoxy-2-methyl-1H-indol-3-yl]-N(2-hydroxyethyl)-3-methylbutanamide Anal. calc'd for C₂₄H₂₉N₂O₃Br: C, 60.89; H, 6.17; N, 5.92. Found: C, 60.73; H, 6.12; N, 5.81.

EXAMPLE 96

3(R) 4-[1-(4-Bromobenzyl)-5-methoxy-2-methyl-1H-indol-3-yl]-N-(3-dimethylaminopropyl)3-methylbutanamide Anal. calc'd for C₂₇H₃₇N₃O₂ClBr.H₂O: C, 57.00; H, 6.91; N, 7.39. Found: C, 56.57; H, 6.83; N, 7.42.

EXAMPLE 97

3-[1-(4-Bromobenzyl)-5-methoxy-2-methyl-1H-indol-3-yl]-N-(2-hydroxyethyl)benzamide ¹H NMR (CD₃COCD₃) δ8.03 (1H, br), 7.85 (2H, m), 7.66 (1H, d ), 7.59 (1H, d), 7.50 (2H, d), 7.30 (1H, d), 7.10 (1H, d), 7.03 (2H, d), 6.79 (1H, dd), 5.49 (2H, s), 3.95 (1H, t), 3.77 (3H, s), 3.70 (2H, t), 3.52 (2H, m), 2.43 (3H, s).

EXAMPLE 98

3-[1-(4-Bromobenzyl)-5-methoxy-2-methyl-1H-indol-3-yl]-N,N-bis(2-hydroxyethyl)benzamide ¹H NMR (CD₃COCD₃) δ7.06–7.35 (6H, m), 7.28 (1H, d), 7.12 (1H, d), 7.01 (2H, d), 6.76 (1H, dd), 5.48 (2H, s), 3.78 (3H, s), 3.8–3.5 (8H, m), 2.8 (2H, br), 2.44 (3H, s).

EXAMPLE 99

3-[1-(4-Bromobenzyl) -5-methoxy-2-methyl-1H-indol-3-yl]benzamide

Anal. calc'd for C₂₉H₂₁N₂O₂Br: C, 64.15; H, 4.71; N, 6.23. Found: C, 64.05; H, 4.83; N, 5.98.

EXAMPLE 100

4-[1-(4-Bromobenzyl)-5-methoxy-2-methyl-1H-indol-3-yl]-N-(4-pyridyl)butanamide

Anal. calc'd for C₂₆H₂₆N₃O₂Br: C, 65.53; H, 5.34; N, 8.55. Found: C, 62.70; H, 5.33; N, 8.52.

EXAMPLE 101

4-[1-(4-Bromobenzyl)-5-methoxy-2-methyl-1H-indol-3-yl]-N-[2-(N-pyrrolidinyl)ethyl]-3-methylbutanamide Anal. calc'd for C₂₈H₃₆N₃O₂Br: C, 63.87; H, 6.89; N, 7.98. Found: C, 63.56; H, 6.84; N, 7.81.

EXAMPLE 102

4-[1-(4-Bromobenzyl)-5-methoxy-2-methyl-1H-indol-3-yl]-N-(3-pyridyl)butanamide

Anal. calc'd for C₂₆H₂₆N₃O₂Br: C, 63.53; H, 5.34; N, 8.55. Found: C, 63.30; H, 5.36; N, 8.51.

EXAMPLE 103

4-[1-(4-Bromobenzyl)-5-methoxy-2-methyl-1H-indol-3-yl]butanamide

Mass (CI): 414, 416 (MH⁺), 342, 344, 307, 169, 171, 154

EXAMPLE 104

4-[1-(4-Bromobenzyl)-5-methoxy-2-methyl-1H-indol-3-yl]-methylbutanamide

Mass (C.I.): 428, 430 (MH⁺), 355,357, 342, 344, 307, 169, 171,154

EXAMPLE 105

N-{3-[1-(4-Bromobenzyl)-5-methoxy-2-methyl-1H-indol-3-yl]benzoyl}methanesulfonamide Mass (C.I.): 527, 529 (MH⁺), 124

EXAMPLE 106

N-{2-[1-(4-Bromobenzyl)-5-methoxy-2-methyl-1H-indol-3-yl]methyl}benzoyl)methanesulfonamide m.p.: 167° C. (dec.)

Examples 107 to 115 may be prepared analogously to the examples listed above and according to method L.

EXAMPLE 116

(4-(1-(4-Bromobenzyl)-5-methoxy-2-methyl-1H-indol-3-yl)-3-methylbutanoyl)-4-methylpiperazine To a solution of the acid from Example 7, Step 6 (300 mg) in DMF (4 mL) was added triethylamine (0.13 mL), diethyl cyanophosphonate (0.13 mL) and 1-methylpiperazine (0.08 mL) at r.t. After 4 h the reaction mixture was diluted with EtOAc and the organic phase was washed with HCl 1M, 5% aqueous $NaHCO_3$ and brine, dried ($MgSO_4$) and evaporated. Flash chromatography of the residue (silica gel; $CH_2Cl_2$/MeOH, 95:5) afforded the title compound as a white solid.

$^1$H NMR ($CDCl_3$) $\delta$7.35 (2H, d), 7.0 (2H, m), 6.7 (3H, m), 5.2 (2H, s), 3.85 (3H, s), 3.65 (2H, m), 3.3 (2H, br,), 2.7 (1H, dd), 2.6 (1H, dd), 2.2–2.5 (6H, m), 2.30 (3H, s), 2.25 (3H, s), 2.15 (1H, d r), 1.0 (3H, d).

EXAMPLE 117

N-{4-[1-(4-Bromobenzyl)-5-methoxy-2-methyl-1H-indol-3-yl]-3-(ethane-1,2-diyl)butanoyl}imidazole Anal. calc'd for $C_{24}H_{27}N_2O_4BrS$: C, 55.49; H, 5.24; N, 5.39. Found : C, 55.53; H, 5.30; N, 5.38.

EXAMPLE 118

3(R) N[4-(1-(4-Bromobenzyl)-5-methoxy-2-methyl-1H-indol-3-yl)-3-methylbutanoyl]morpholine Mass (C.I.): 499,501 ($MH^+$), 498,500 ($M^+$), 412,414,369, 371, 342,344.

EXAMPLE 119

N-[4-(1-(4-Bromobenzyl)-5-methoxy-2-methyl-1H-indol-3-yl)-3(S)-methylbutanoyl]-4(R)-isopropyl-2-oxazolidinone Isomer A of Example 7, Step 7.

EXAMPLE 120

N-[4-(1-(4-Bromobenzyl) -5-methoxy-2-methyl-1H-indol-3-yl)-3 (R)-methylbutanoyl]-4(R)-isopropyl-2-oxazolidinone Isomer B of Example 7, Step 7.

EXAMPLE 121

N-[4-(1-(4-Bromobenzyl)-5-methoxy-2-methyl-1H-indol-3-yl) pentanoyl]-2-oxalidinone Compound from Example 15, Step 6.

EXAMPLE 122

N-[4-(1-(4-Bromobenzyl)-5-methoxy-2-methyl-1H-indol-3-yl)-2-methylpentanoyl]-2-oxalidinone Compound from Example 15, Step 7.

Examples 123 to 125 may be prepared as described for the examples listed above and according to method L.

EXAMPLE 126

4-[1-(4-Bromobenzyl)-5-methoxy-2-methyl-1H-indol-3-yl]-3-methylbutanethioamide

To the amide (530 mg, 1.30 mmol) of Example 90 in 1,4-dioxane (10.0 mL) was added the Lawesson reagent (310 mg, 0.767 mmol). After refluxing for 2 min, the solvent was evaporated in vacuo and the title product was purified by flash chromatography (30% EtOAc in hexane).

$^1$H NMR ($CD_3COCD_3$) $\delta$8.60 (2H, br), 7.45 (2H, d), 7.18 (1H, d), 7.15 (1H, d), 6.90 (2H, d), 6.70 (1H, dd), 3.80 (3H, s), 2.50 to 2.90 (5H, m), 2.30 (3H, s), 0.95 (3H, d).

EXAMPLE 127

N-Methyl-4-[1-(4-bromobenzyl)-5-methoxy-2-methyl-1H-indol-3-yl]-3-methylbutanethioamide Mass (CI): 458,459,460,461,369,371,342,344, 169,171.

EXAMPLE 128

4-[1-(4-Bromobenzyl)-5-chloro-2-methyl-1H-indol-3-yl]-3-methylbutanethioamide $^1$H NMR ($CD_3COCD_3$) $\delta$8.6 (2H, br), 7.63 (1H, d), 7.46 (2H, d), 7.30 (1H, d), 7.02 (1H, dd), 6.91 (2H, d), 5.44 (2H, s), 2.9 (1H, m), 2.7(1H, m), 2.55 (3H, m), 2.36 (3H, s), 0.95 (4H, d).

EXAMPLE 129

4-[1-(4-Bromobenzyl)-5-methoxy-2-methyl-1H-indol-3-yl]butanethioamide

Mass (CI): 429,430,431,432,355,357,342,344 306,169, 171,154

EXAMPLE 126

4-[1-(4-Bromobenzyl)-5-methoxy-2-methyl-1H-indol-3-yl]-N-methylbutanethioamide

Mass (CI): 444, 445, 446, 447, 355, 357, 342, 344, 169, 171, 154

EXAMPLE 131

3(R) 4-[1-(4-Bromobenzyl)-5-methoxy-2-methyl-1H-indol-3-yl]-3-methylbutanethioamide Mass (CI): 444, 445, 446, 447, 369, 371, 342, 344, 201, 169, 171, 116

Examples 132 to 136 may be prepared as described for the examples listed above and according to method M.

What is claimed is:

1. A compound of formula I

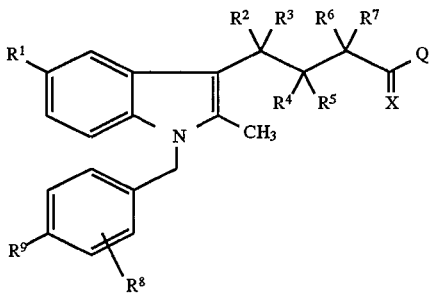

or a pharmaceutically acceptable salt thereof, wherein:

Q is
- (a) —OR or
- (b) —$NR^{11}R^{12}$;

X is
- (a) —O or
- (b) —S;

R is
- (a) —H or
- (b) —$C_{1-4}$ alkyl or mono, di or tri-substituted —$C_{1-4}$ alkyl, where the substituent is selected from F, Cl, Br and I;

$R^1$ is
- (a) —$OCH_3$ or $OCH_2CH_3$,
- (b) —$OCH_2F$,
- (c) —$OCHF_2$,
- (d) —$OCF_3$,
- (e) —$CF_3$,
- (f) —F, Cl, Br or I
- (g) methyl or ethyl;

$R^2$, $R^3$, $R^4$, $R^5$, $R^6$ and $R^7$ are each independently
- (a) —H,
- (b) —F or Cl,
- (c) —$C_{1-5}$ alkyl or haloalkyl,
- (d) —$C_{3-6}$ cycloalkyl,
- (e) —$CF_3$, $CF_2H$ or $CFH_2$,
- (f) —OH, $OR^{10}$, $SR^{10}$, $S(O)R^{10}$ or $S(O)_2R^{10}$,
- (g) nonsubstituted, mono- or di-substituted benzyl, wherein the substituent is selected from
  - (1) $CF_3$,
  - (2) CN,
  - (3) F, Cl, Br or I,
  - (4) $C_{1-6}$ alkyl,
  - (5) $OR^{10}$, $SR^{10}$, $S(O)R^{10}$ or $S(O)_2R^{10}$,
- (h) phenyl or mono- or di-substituted phenyl, wherein the substituent is selected from
  - (1) CF3,
  - (2) CN,
  - (3) F, Cl, Br, I,
  - (4) $C_{1-6}$ alkyl,
  - (5) $OR^{10}$, $SR^{10}$, $S(O)R^{10}$ or $S(O)_2R^{10}$, or $R^2$ together with $R^3$ form an oxo group;
or $R^4$ together with $R^5$ form an oxo group;
or $R^6$ together with $R^7$ form an oxo group;
or $R^2$ and $R^3$ are joined so that together with the carbon atom to which they are attached there is formed a saturated monocyclic ring of 3, 4, 5, 6 or 7 members, optionally one hetero atom which is oxygen;
or $R^3$ and $R^4$ are joined so that together with the carbon atoms to which they are attached there is formed a saturated or aromatic monocyclic ring of 3, 4, 5, 6 or 7 members;
or $R^3$ and $R^6$ are joined so that together with the carbon atoms to which they are attached there is formed a saturated or aromatic monocyclic ring of 3, 4, 5, 6 or 7 members;
or $R^4$ and $R^5$ are joined so that together with the carbon atom to which they are attached there is formed a saturated monocyclic ring of 3, 4, 5, 6 or 7 members, optionally containing one hetero atom which is oxygen;
or $R^4$ and $R^6$ are joined so that together with the carbon atoms to which they are attached there is formed a saturated or aromatic monocyclic ring of 3, 4, 5, 6 or members;
or $R^6$ and $R^7$ are joined so that together with the carbon atom to which they are attached there is formed a saturated monocyclic ring of 3, 4, 5, 6 or 7 members, optionally containing an oxygen atom;

$R^8$ is
- (a) hydrogen or
- (b) F, Cl or Br, $R^9$ is
- (a) Br, Cl or I,
- (b) SMe, S(O)Me, SEt, $SCF_2H$ or $SCF_3$;

$R^{10}$ is methyl, ethyl or, benzyl optionally mono- or di-substituted, wherein the substituent is selected from
- (1) $CF_3$,
- (2) CN,
- (3) F, Cl, Br, I, and
- (4) $C_{1-6}$ alkyl;

$R^{11}$ and $R^{12}$ are each independently
- (a) —H,
- (b) —$C_{1-4}$ alkyl,
- (c) —$C_{3-6}$ cycloalkyl,
- (d) —OR,
- (e) —$C(O)R^{13}$,
- (f) —$S(O)_2R^{14}$,
- (g) mono-substituted $C_{2-4}$ alkyl wherein the substituent is selected from
  - (1) hydroxy,
  - (2) amino,
  - (3) methylamino, and
  - (4) dimethylamino,
- (h) phenyl, benzyl or pyridyl optionally mono- or di-substituted, the substituents being selected from the group consisting of
  - (1) $CF_3$,
  - (2) CN,
  - (3) F, Cl, Br or I,
  - (4) $C_{1-6}$ alkyl;

$R^{13}$ is
- (a) —H,
- (b) —$C_{1-4}$ alkyl,
- (c) —$CF_3$,
- (d) phenyl or benzyl optionally mono- or di-substituted, the substituents being selected from the group consisting of
  - (1) $CF_3$,
  - (2) CN,
  - (3) F, Cl, Br or I,
  - (4) $C_{1-6}$ alkyl;

$R^{14}$ is
- (a) —$C_{1-4}$ alkyl,
- (b) —$CF_3$,
- (c) phenyl or benzyl optionally mono- or di-substituted, the substituents being selected from the group consisting of
  - (1) $CF_3$, (2) CN,
(3) F, Cl, Br or I,
(4) $C_{1-6}$ alkyl.

2. A compound according to claim 1 wherein

Q is
  (a) —OR or
  (b) —NR$^{11}$R$^{12}$;

X is
  (a) —O or
  (b) —S;

R is
  (a) —H or
  (b) —$C_{1-4}$ alkyl;

R$^1$ is
  (a) —OCH$_3$,
  (b) —OCF$_3$,
  (c) —CF$_3$,
  (d) Cl or Br,
  (e) methyl;

R$^2$, R$^3$, R$^4$, R$^5$, R$^6$ and R$^7$ are independently
  (a) —H,
  (b) —F or Cl,
  (c) —$C_{1-3}$ alkyl or haloalkyl,
  (d) —$C_{3-6}$ cycloalkyl,
  (e) —CF$_3$,
  (f) —OH,
  (g) nonsubstituted, mono- or di-substituted benzyl, wherein the substituent is selected from
    (1) F, Cl, Br or I,
    (2) $C_{1-3}$ alkyl,
or R$^2$ together with R$^3$ form an oxo group;
or R$^2$ and R$^3$ are joined so that together with the carbon atom to which they are attached there is formed a saturated monocyclic ring of 3, 4, 5, 6 or 7 members;
or R$^3$ and R$^4$ are joined so that together with the carbon atoms to which they are attached there is formed a saturated or aromatic monocyclic ring of 3, 4, 5, 6 or 7 members;
or R$^3$ and R$^6$ are joined so that together with the carbon atoms to which they are attached there is formed a saturated or aromatic monocyclic ring of 3, 4, 5, 6 or 7 members;
or R$^4$ and R$^5$ are joined so that together with the carbon atom to which they are attached there is formed a saturated monocyclic ring of 3, 4, 5, 6 or 7 members;
or R$^4$ and R$^6$ are joined so that together with the carbon atoms to which they are attached there is formed a saturated or aromatic monocyclic ring of 3, 4, 5, 6 or 7 members;
or R$^6$ and R$^7$ are joined so that together with the carbon atom to which they are attached there is formed a saturated monocyclic ring of 3, 4, 5, 6 or 7 members;

R$^8$ is
  (a) hydrogen or
  (b) F or Cl;

R$^9$ is
  (a) Br, Cl or I,
  (b) SMe, S(O)Me, SEt;

R$^{11}$ and R$^{12}$ are independently
  (a) —H,
  (b) —$C_{1-4}$ alkyl,
  (c) —OR,
  (d) —S(O)$_2$R$^{14}$,
  (e) mono-substituted $C_{2-4}$ alkyl wherein the substituent is selected from
    (1) hydroxy,
    (2) amino,
    (3) methylamino, and
    (4) dimethylamino,
  (f) phenyl, benzyl or pyridyl optionally mono- or di-substituted, the substituents being selected from the group consisting of
    (1) CF$_3$,
    (2) F, Cl, Br, or
    (3) $C_{1-3}$ alkyl;

R$^{14}$ is
  (a) —$C_{1-4}$ alkyl,
  (b) —CF$_3$,
  (c) phenyl optionally mono- or di-substituted, the substituents being selected from the group consisting of
    (1) CF$_3$,
    (2) F, Cl, Br or I,
    (3) $C_{1-3}$ alkyl.

3. A compound according to claim 2 wherein

Q is
  (a) —OR or
  (b) —NR$^{11}$R$^{12}$;

X is
  (a) —O or
  (b) —S;

R is
  (a) —H or
  (b) —$C_{1-4}$ alkyl;

R$^1$ is
  (a) —OCH$_3$,
  (b) —OCF$_3$,
  (c) —CF$_3$,
  (d) Cl or Br,
  (e) methyl;

R$^2$, R$^3$, R$^4$, R$^5$, R$^6$ and R$^7$ are independently
  (a) —H,
  (b) —F or Cl,
  (c) —$C_{1-3}$ alkyl or haloalkyl,
  (d) —$C_{3-6}$ cycloalkyl,
  (e) —CF$_3$,
  (f) —OH,
  (g) nonsubstituted, mono- or di-substituted benzyl, wherein the substituent is selected from
    (1) F, Cl, Br or I,
    (2) $C_{1-3}$ alkyl,
or R$^2$ together with R$^3$ form an oxo group;
or R$^2$ and R$^3$ are joined so that together with the carbon atom to which they are attached there is formed a saturated monocyclic ring of 3, 4, 5, 6 or 7 members;
or R$^3$ and R$^4$ are joined so that together with the carbon atoms to which they are attached there is formed a saturated or aromatic monocyclic ring of 3, 4, 5, 6 or 7 members;
or R$^3$ and R$^6$ are joined so that together with the carbon atoms to which they are attached there is formed a saturated or aromatic monocyclic ring of 3, 4, 5, 6 or 7 members;
or R$^4$ and R$^5$ are joined so that together with the carbon atom to which they are attached there is formed a saturated monocyclic ring of 3, 4, 5, 6 or 7 members;

R$^8$ is
  (a) hydrogen or
  (b) F or Cl;

R$^9$ is
  (a) Br, Cl or I, (b) SMe, S(O)Me, SEt;

$R^{11}$ and $R^{12}$ are independently
(a) —H,
(b) —$C_{1-4}$ alkyl,
(c) —OR,
(d) —S(O)$_2$R$^{14}$,
(e) mono-substituted $C_{2-4}$ alkyl wherein the substituent is selected from
  (1) hydroxy,
  (2) amino,
  (3) methylamino, and
  (4) dimethylamino,
(f) phenyl, benzyl or pyridyl optionally mono- or di-substituted, the substituents being selected from the group consisting of
  (1) CF$_3$,
  (2) F, Cl, Br, or
  (3) $C_{1-3}$ alkyl;

$R^{14}$ is
(a) —$C_{1-4}$ alkyl,
(b) —CF$_3$,
(c) phenyl optionally mono- or di-substituted, the substituents being selected from the group consisting of
  (1) CF$_3$,
  (2) F, Cl, Br or I,
  (3) $C_{1-3}$ alkyl.

4. A compound according to claim 3 wherein

Q is
(a) —OR or
(b) —NR$^{11}$R$^{12}$;

X is
(a) —O or
(b) —S;

R is
(a) —H or
(b) methyl;

$R^1$ is
(a) —OCH$_3$,
(b) —OCF$_3$,
(c) Cl or Br,
(d) methyl;

$R^2$, $R^3$, $R^4$, $R^5$, $R^6$ and $R^7$ are independently
(a) —H,
(b) —F,
(c) —$C_{1-3}$ alkyl or substituted —$C_{1-3}$ alkyl wherein the substituent is F or Cl,
(d) —CF$_3$,
(e) —OH, or $R^2$ together with $R^3$ form an oxo group;

or $R^2$ and $R^3$ are joined so that together with the carbon atom to which they are attached there is formed a saturated monocyclic ring of 4, 5 or 6 members;

or $R^3$ and $R^4$ are joined so that together with the carbon atoms to which they are attached there is formed a saturated or aromatic monocyclic ring of 4, 5 or 6 members;

or $R^3$ and $R^6$ are joined so that together with the carbon atoms to which they are attached there is formed a saturated or aromatic monocyclic ring of 4, 5 or 6 members;

or $R^4$ and $R^5$ are joined so that together with the carbon atom to which they are attached there is formed a saturated monocyclic ring of 4, 5 or 6 members;

$R^8$ is hydrogen;

$R^9$ is
(a) Br, Cl or I,
(b) SMe, S(O)Me;

$R^{11}$ and $R^{12}$ are independently
(a) —H,
(b) —methyl,
(c) —OR,
(d) —S(O)$_2$CH$_3$,
(e) mono-substituted $C_{2-4}$ alkyl wherein the substituent is selected from
  (1) hydroxy, and
  (2) amino,
(f) phenyl, benzyl or pyridyl optionally mono- or di-substituted, the substituents being selected from the group consisting of
  (1) CF$_3$,
  (2) F, Cl, Br, or
  (3) $C_{1-3}$ alkyl;

$R^{14}$ is
(a) methyl,
(b) —CF$_3$,
(c) phenyl optionally mono- or di-substituted, the substituents being selected from the group consisting of
  (1) CF$_3$,
  (2) F, Cl or Br,
  (3) methyl.

5. A compound according to claim 1 wherein

Q is
(a) —OR or
(b) —NR$^{11}$R$^{12}$;

X is
(a) —O or
(b) —S;

R is
(a) —H or
(b) methyl;

$R^1$ is
(a) —OCH$_3$,
(b) —OCF$_3$,
(c) Cl or Br,
(d) methyl;

$R^2$, $R^3$, $R^4$, $R^5$, $R^6$ and $R^7$ are independently
(a) —H,
(b) —F,
(c) —$C_{1-3}$ alkyl or substituted —$C_{1-3}$ alkyl wherein the substituent is F or Cl,
(d) —CF$_3$,
(e) —OH, or $R^2$ together with $R^3$ form an oxo group;

or $R^2$ and $R^3$ are joined so that together with the carbon atom to which they are attached there is formed a saturated monocyclic ring of 3, 4, 5, 6 or 7 members;

or $R^4$ and $R^5$ are joined so that together with the carbon atom to which they are attached there is formed a saturated monocyclic ring of 3, 4, 5, 6 or 7 members;

$R^8$ is hydrogen;

$R^9$ is
(a) Br, Cl or I,
(b) SMe, S(O)Me;

$R^{11}$ and $R^{12}$ are independently
(a) —H,
(b) —methyl,
(c) —OR,
(d) —S(O)$_2$CH$_3$,
(e) mono-substituted $C_{2-4}$ alkyl wherein the substituent is selected from (1) hydroxy, and
(2) amino,
(f) phenyl, benzyl or pyridyl optionally mono- or di-substituted, the substituents being selected from the group consisting of
(1) $CF_3$,
(2) F, Cl, Br, or
(3) $C_{1-3}$ alkyl;

$R^{14}$ is
(a) methyl,
(b) —$CF_3$,
(c) phenyl optionally mono- or di-substituted, the substituents being selected from the group consisting of
(1) $CF_3$,
(2) F, Cl or Br,
(3) methyl.

6. A compound according to claim 5 wherein
Q is
(a) —OR or
(b) —$NR^{22}R^{12}$;
X is
(a) —O or
(b) —S;
R is
(a) —H or
(b) methyl;
$R^1$ is
(a) —$OCH_3$,
(b) —$OCF_3$,
(c) Cl or Br,
(d) methyl;
$R^2$, $R^3$, $R^4$, $R^5$, $R^6$ and $R^7$ are independently
(a) —H,
(b) —F,
(c) —$C_{1-3}$ alkyl or substituted —$C_{1-3}$ alkyl wherein the substituent is F or Cl,
(d) —$CF_3$,
(e) —OH,
or $R^2$ together with $R^3$ form an oxo group;
$R^8$ is hydrogen;
$R^9$ is
(a) Br, Cl or I,
(b) SMe, S(O)Me;
$R^{11}$ and $R^{12}$ are independently
(a) —H,
(b) —methyl,
(c) —OR,
(d) —$S(O)_2CH_3$,
(e) mono-substituted $C_{2-4}$ alkyl wherein the substituent is selected from
(1) hydroxy, and
(2) amino,
(f) phenyl, benzyl or pyridyl optionally mono- or di-substituted, the substituents being selected from the group consisting of
(1) $CF_3$,
(2) F, Cl, Br, or
(3) $C_{1-3}$ alkyl;

$R^{14}$ is
(a) methyl,
(b) —$CF_3$,
(c) phenyl optionally mono- or di-substituted, the substituents being selected from the group consisting of
(1) $CF_3$,
(2) F, Cl or Br,
(3) methyl.

7. A compound according to claim 6 wherein
Q is
(a) —OR or
(b) —$NR^{11}R^{12}$;
X is
(a) —O or
(b) —S;
R is
(a) —H or
(b) methyl;
$R^1$ is
(a) —$OCH_3$,
(b) —$OCF_3$,
(c) Cl or Br,
(d) methyl;
$R^2$, $R^3$, $R^4$, $R^5$, $R^6$ and $R^7$ are independently
(a) —H,
(b) —F,
(c) —methyl or ethyl or substituted methyl or ethyl wherein the substituent is F or Cl,
or $R^2$ together with $R^3$ form an oxo group;
$R^8$ is hydrogen;
$R^9$ is
(a) Br, Cl or I,
(b) SMe, S(O)Me;
$R^{11}$ and $R^{12}$ are independently
(a) —H,
(b) —methyl,
(c) —OR,
(d) —$S(O)_2CH_3$,
(e) mono-substituted ethyl or propyl wherein the substituent is selected from
(1) hydroxy, and
(2) amino,
(f) phenyl, benzyl or pyridyl optionally mono- or di-substituted, the substituents being selected from the group consisting of
(1) $CF_3$,
(2) F, Cl, Br, or
(3) methyl;

$R^{14}$ is
(a) methyl,
(b) —$CF_3$,
(c) phenyl optionally mono- or di-substituted, the substituents being selected from the group consisting of
(1) $CF_3$,
(2) F, Cl or Br,
(3) methyl.

8. A compound selected from the group consisting of
(1) 3-[1-(1-(4-Bromobenzyl)-5-methoxy-2-methyl-1H-indol-3-yl)-cyclopropyl]propanoic acid,
(2) [4-(1-(4-Bromobenzyl)-5-methoxy-2-methyl-1H-indol-3-yl)-3-(ethane-1,2-diyl)]butanoic acid, sodium salt,
(3) 4-(1-(4-Bromobenzyl)-5-methoxy-2-methyl-1H-indol-3-yl)-2-methylbutanoic acid,
(4) 4-(1-(4-Bromobenzyl)-5-methoxy-2-methyl-1H-indol-3-yl)butanoic acid,
(5) 4-(1-(4-Bromobenzyl)-5-methoxy-2-methyl-1H-indol-3-yl)-2,2-dimethylbutanoic acid, sodium salt
(6) 4-(1-(4-Bromobenzyl)-5-methoxy-2-methyl-1H-indol-3-yl)-2-hydroxy-2-methylbutanoic acid,
(7) (3S) and (3R) 4-(1-(4-Bromobenzyl)-5-methoxy-2-methyl-1H-indol-3-yl)-3-methylbutanoic acid,
(8) [5-Methoxy-2-methyl-1-(4-methylthiobenzyl)indol-3-yl]-3-methylbutanoic acid, (9) trans-2-[(1-(4-Bromobenzyl)-5-methoxy-2-methyl-1H-indol-3-yl)methyl]cyclopropanecarboxylic acid,
(10) (2R,3S)-[(4-Bromobenzyl)-5-methoxy-2-methyl-1H-indol-3-yl]-2,3-dimethylbutanoic acid,
(11) (2R,3R)-[1-(4-Bromobenzyl)-5-methoxy-2-methyl-1H-indol-3-yl]-2,3-dimethylbutanoic acid,
(12) (2S,3R)-[1-(4-Bromobenzyl)-5-methoxy-2-methyl-1H-indol-3-yl]-2,3-dimethylbutanoic acid,
(13) (2S,3S)-[1-(4-Bromobenzyl)-5-methoxy-2-methyl-1H-indol-3-yl]-2,3-dimethylbutanoic acid,
(14) 4-(1-(4-Bromobenzyl)-5-methoxy-2-methyl-1H-indol-3-yl)-2-methylpentanoic acid,
(15) 4-(1-(4-Bromobenzyl)-5-methoxy-2-methyl-1H-indol-3-yl)-4-oxobutanoic acid,
(16) cis-2-[(1-(4-Bromobenzyl)-5-methoxy-2-methyl-1H-indol-3-yl)methyl]cyclopropanecarboxylic acid
(17) (R)-(−)-4-(1-(4-Bromobenzyl)-5-methoxy-2-methyl-1H-indol-3-yl)-3-methylbutanoic acid,
(18) 2-[(5-Bromo-1-(4-bromobenzyl)-2-methyl-1H-indol-3-yl)methyl]benzoic acid,
(19) [2-(1-(4-Bromobenzyl)-5-methoxyl-2-methyl-1H-indol-3-yl) phenyl]acetic acid, sodium salt,
(20) 2-[(1-(4-Bromobenzyl)-5-methoxy-2-methyl-1H-indol-3-yl)methyl]benzoic acid,
(21) [3-(4-Bromobenzyl)-5-methoxy-2-methyl-1H-indol-3-yl]benzoic acid, sodium salt,
(22) 4-[1-(4-Bromobenzyl)-2,5-dimethyl-1H-indol-3-yl] butanoic acid,
(23) 4-[5-Bromo-1-(4-bromobenzyl)-2-methyl-1H-indol-3-yl]butanoic acid,
(24) 4-[1-(4-Chlorobenzyl)-5-methoxy-2-methyl-1H-indol-3-yl]-3-(ethane-1,2-diyl)butanoic acid,
(25) 4-[1-(4-Bromobenzyl)-5-chloro-2-methyl-1H-indol-3-yl]butanoic acid,
(26) 4-[5-Bromo-1-(4-chlorobenzyl)-2-methyl-1H-indol-3-yl]butanoic acid,
(27) 4-[5-Chloro-1-(4-chlorobenzyl)-2-methyl-1H-indol-3-yl]butanoic acid,
(28) 4-[1-(4-Bromo-2-fluorobenzyl)-5-chloro-2-methyl-1H-indol-3-yl]butanoic acid,
(29) 4-[1-(4-Bromo-2-fluorobenzyl)-5-chloro-2-methyl-1H-indol-3-yl]-2-methylbutanoic acid,
(30) 4-[5-Methoxy-2-methyl-1-(4-methylthiobenzyl)-1H-indol-3-yl]-3-(ethane-1,2-diyl)butanoic acid,
(31) 4-[5-Bromo-1-(4-bromobenzyl)-2-methyl-1H-indol-3-yl]-3-(ethane-1,2-diyl)butanoic acid,
(32) trans 2-(4-[1-(4-Bromobenzyl)-5-chloro-2-methyl-1H-indol-3-yl]methyl) cyclopropanecarboxylic acid,
(33) 4-[1-(4-Bromobenzyl)-5-chloro-2-methyl-1H-indol-3-yl]-3-methyl-butanoic acid,
(34) 4-[1-(4-Bromobenzyl)-5-chloro-2-methyl-1H-indol-3-yl]-2-methyl-butanoic acid,
(35) 4-[1-(4-Bromobenzyl)-5-chloro-2-methyl-1H-indol-3-yl]-2,3-dimethyl-butanoic acid,
(36) 4-(1-Benzyl-5-chloro-2-methyl-1H-indol-3-yl) pentanoic acid,
(37) 4-[1-(4-Bromobenzyl)-5-chloro-2-methyl-1H-indol-3-yl]pentanoic acid,
(38) 4-[1-(4-Bromobenzyl)-5-methoxy-2-methyl-1H-indol-3-yl]-3-methyl-butanoic acid
(39) 4-[5-Methoxy-2-methyl-1-(4-methanesulfoxylbenzyl)-1H-indol-3-yl]-3-(ethane-1,2-diyl)butanoic acid,
(40) 4-[1-(4-Bromobenzyl)-5-methoxy-2-methyl-1H-indol-3-yl]pentanoic acid,
(41) 4-[1-(4-Bromobenzyl)-5-methoxy-2-methyl-1H-indol-3-yl]-2,3-dimethylbutanoic acid, sodium salt,
(42) 3(S), 4-[1-(4-Bromobenzyl)-5-chloro-2-methyl-1H-indol-3-yl]-3-methylbutanoic acid, sodium salt,
(43) 3(R), 4-[1-(4-Bromobenzyl)-5-chloro-2-methyl-1H-indol-3-yl]-3-methylbutanoic acid, sodium salt,
(44) 4-[1-(4-Bromobenzyl)-5-methoxy-2-methyl-1H-indol-3-yl]-3-(ethane-1,2-diyl)-2-methylbutanoic acid,
(45) 4-[1-(4-Bromobenzyl)-5-methoxy-2-methyl-1H-indol-3-yl]-3-ethylbutanoic acid,
(46) 4-[1-(4-Bromobenzyl)-5-methoxy-2-methyl-1H-indol-3-yl]-3-methylpentanoic acid, sodium salt,
(47) 4-[1-(4-Bromobenzyl)-5-methoxy-2-methyl-1H-indol-3-yl]-3,3-dimethylbutanoic acid, sodium salt,
(48) 4-[1-(4-Bromobenzyl)-5-methyl-5-trifluoromethyl-1H-indol-3-yl]butanoic acid,
(49) 2(R) 4-[1-(4-Bromobenzyl)-5-chloro-2-methyl-1H-indol-3-yl]-2-methylbutanoic acid,
(50) 2(S), 4-[1-(4-Bromobenzyl)-5-chloro-2-methyl-1H-indol-3-yl]-2-methylbutanoic acid, sodium salt,
(51) 4-[1-(4-Bromobenzyl)-5-methoxy-2-methyl-1H-indol-3-yl]-2-benzylbutanoic acid,
(52) 4-[5-Chloro-1-(4-iodobenzyl)-2-methyl-1H-indol-3-yl] butanoic acid,
(53) 4-[1-(4-Bromobenzyl)-5-methoxy-2-methyl-1H-indol-3-yl]-2-ethylbutanoic acid,
(54) 4-[5-Bromo-1-(4-bromobenzyl)-2-methyl-1H-indol-3-yl]-3,3-dimethylbutanoic acid,
(55) 4-[1-(4-Bromobenzyl)-5-chloro-2-methyl-1H-indol-3-yl]-3,3-dimethylbutanoic acid,
(56) 2(R), 3(R) 4-[1-(4-Bromobenzyl)-5-chloro-2-methyl-1H-indol-3-yl]-2,3-dimethylbutanoic acid,
(57) 2(S), 3(R) 4-[1-(4-Bromobenzyl)-5-chloro-2-methyl-1H-indol-3-yl]-2,3-dimethylbutanoic acid,
(58) 3(R) 4-[1-(4-Iodobenzyl)-5-methoxy-2-methyl-1H-indol-3-yl]-3-methylbutanoic acid,
(59) 4-[1-(4-Bromobenzyl)-5-chloro-2-methyl-1H-indol-3-yl]-3-(ethane-1,2-diyl)butanoic acid,
(60) 3(R) 4-[1-(4-Ethylthiobenzyl)-5-methoxy-2-methyl-1H-indol-3-yl]-3-methylbutanoic acid,
(61) Methyl 4-[1-(4-bromobenzyl)-5-methoxy-2-methyl-1H-indol-3-yl]butanoate,
(62) 2-{[1-(4-Bromobenzyl)-5-methoxy-2-methyl-1H-indol-3-yl]acyl}benzoic acid,
(63) 5-[1-(4-Bromobenzyl)-5-methoxy-2-methyl-1H-indol-3-yl]-2-methylbenzoic acid,
(64) 4-[1-(4-Bromobenzyl)-5-methoxy-2-methyl-1H-indol-3-yl]-3-methylbutanamide,
(65) 4-(1-(4-Bromobenzyl)-5-methoxy-2-methyl-1H-indol-3-yl)-N-(2-pyridyl)butanamide,
(66) [4-(1-(4-Bromobenzyl)-5-methoxy-2-methyl-1H-indol-3-yl)-3-(ethane-1,2-diyl)]butanoyl methanesulfonamide,
(67) 3(R) 4-[1-(4-Bromobenzyl)-5-methoxy-2-methyl-1H-indol-3-yl]-3-methylbutanamide,
(68) 3(R) 4-[1-(4-Bromobenzyl)-5-methoxy-2-methyl-1H-indol-3-yl]-N,N-dimethyl-3-methylbutanamide,
(69) 4-[1-(4-Bromobenzyl)-5-methoxy-2-methyl-1H-indol-3-yl]-N(2-hydroxyethyl)-3-methylbutanamide,
(70) 3(R) 4-[1-(4-Bromobenzyl)-5-methoxy-2-methyl-1H-indol-3-yl]-N-(3-dimethylaminopropyl)-3-ethylbutanamide,
(71) 3-[1-(4-Bromobenzyl)-5-methoxy-2-methyl-1H-indol-3-yl]-N-(2-hydroxyethyl)benzamide,
(72) 3-[1-(4-Bromobenzyl)-5-methoxy-2-methyl-1H-indol-3-yl]-N,N-bis(2-hydroxyethyl)benzamide,
(73) 3-[1-(4-Bromobenzyl)-5-methoxy-2-methyl-1H-indol-3-yl]benzamide,
(74) 4-[1-(4-Bromobenzyl)-5-methoxy-2-methyl-1H-indol-3-yl]-N-(4-pyridyl)butanamide,
(75) 4-[1-(4-Bromobenzyl)-5-methoxy-2-methyl-1H-indol-3-yl]-N-[2-(N-pyrrolidinyl) ethyl]-3-methylbutanamide,

(76) 4-[1-(4-Bromobenzyl)-5-methoxy-2-methyl-1H-indol-3-yl]-N-(3-pyridyl)butanamide,

(77) 4-[1-(4-Bromobenzyl)-5-methoxy-2-methyl-1H-indol-3-yl]butanamide,

(78) 4-[1-(4-Bromobenzyl)-5-methoxy-2-methyl-1H-indol-3-yl]-methylbutanamide,

(79) N-{3-[1-(4-Bromobenzyl)-5-methoxy-2-methyl-1H-indol-3-yl]benzoyl}methanesulfonamide,

(80) N-{2-[1-(4-Bromobenzyl)-5-methoxy-2-methyl-1H-indol-3-yl]methyl}benzoyl)methanesulfonamide,

(81) 4-[1-(4-Bromobenzyl)-5-methoxy-2-methyl-1H-indol-3-yl]-3-methylbutanethioamide,

(82) N-Methyl-4-[1-(4-bromobenzyl)-5-methoxy-2-methyl-1H-indol-3-yl]-3-methylbutanethioamide,

(83) 4-[1-(4-Bromobenzyl)-5-chloro-2-methyl-1H-indol-3-yl]-3-methylbutanethioamide,

(84) 4-[1-(4-Bromobenzyl)-5-methoxy-2-methyl-1H-indol-3-yl]butanethioamide,

(85) 4-[1-(4-Bromobenzyl)-5-methoxy-2-methyl-1H-indol-3-yl]-N-methylbutanethioamide,and

(86) 3(R) 4-[1-(4-Bromobenzyl)-5-methoxy-2-methyl-1H-indol-3-yl]-3-methylbutanethioamide, or a pharmaceutically acceptable salt thereof.

9. A method of treating an inflammatory disease susceptable to treatment with an non-steroid al anti-inflammatory agent comprising:

administration to a patient in need of such treatment of a non-toxic therapeutically effective amount of a compound according to claim 1 and a pharmaceutically acceptable carrier.

10. A method of treating cyclooxygenase mediated diseases advantageously treated by an active agent that selectively inhibits COX-2 in preference to COX-1 comprising:

administration to a patient in need of such treatment of a non-toxic therapeutically effective amount of a compound according to claim 1.

11. A compound selected from the group consisting of
(3S) 4-(1-(4-Bromobenzyl)-5-methoxy-2-methyl-1H-indol-3-yl)-3-methylbutanoic acid, and
(3R) 4-(1-(4-Bromobenzyl)-5-methoxy-2-methyl-1H-indol-3-yl)-3-methylbutanoic acid.

12. A pharmaceutical composition for treating an inflammatory disease susceptable to treatment with an non-steroid al anti-inflammatory agent comprising:

a non-toxic therapeutically effective amount of a compound according to claim 1 and a pharmaceutically acceptable carrier.

13. A pharmaceutical composition for treating cyclooxygenase mediated diseases advantageously treated by an active agent that selectively inhibits COX-2 in preference to COX-1 comprising:

a non-toxic therapeutically effective amount of a compound according to claim 1 and a pharmaceutically acceptable carrier.

* * * * *